(12) United States Patent
Ting et al.

(10) Patent No.: US 7,705,153 B2
(45) Date of Patent: Apr. 27, 2010

(54) BIPIPERDINE DERIVATIVES USEFUL AS CCR3 ANTAGONISTS

(75) Inventors: Pauline C. Ting, New Providence, NJ (US); Jianhua Cao, Edison, NJ (US); Youhao Dong, Edison, NJ (US); Eric J. Gilbert, Scotch Plains, NJ (US); Ying Huang, Berkeley Heights, NJ (US); Joseph M. Kelly, Parlin, NJ (US); Stuart McCombie, Caldwell, NJ (US); Neng-Yang Shih, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 928 days.

(21) Appl. No.: 11/049,460

(22) Filed: Feb. 2, 2005

(65) Prior Publication Data

US 2005/0182095 A1 Aug. 18, 2005

Related U.S. Application Data

(60) Provisional application No. 60/542,013, filed on Feb. 5, 2004.

(51) Int. Cl.
*A61K 31/4709* (2006.01)
*A61K 31/4725* (2006.01)
*C07D 215/14* (2006.01)

(52) U.S. Cl. ............... 546/168; 546/146; 514/307; 514/314

(58) Field of Classification Search ............... 514/307, 514/311, 318, 320, 314; 546/139, 148, 167, 546/146, 168

See application file for complete search history.

(56) References Cited

U.S. PATENT DOCUMENTS

| 5,883,096 | A | 3/1999 | Lowe et al. |
| 5,889,006 | A | 3/1999 | Lowe et al. |
| 5,952,349 | A | 9/1999 | Asberom et al. |
| 5,977,138 | A | 11/1999 | Wang et al. |
| 6,037,352 | A | 3/2000 | Lowe et al. |
| 6,387,930 | B1 | 5/2002 | Baroudy et al. |

FOREIGN PATENT DOCUMENTS

| WO | WO 9805292 | * | 2/1998 |
| WO | WO00/66558 | | 11/2000 |
| WO | WO 01/77101 | | 10/2001 |

OTHER PUBLICATIONS

Silverman, R.B. The Organic Chemistry of Drug Design and Drug Action 1992, Academic: New York, p. 19.*

Ting et. al. "The synthesis of substituted bipiperidine amide compounds as CCR3 ligands: Antagonists versus agonists" Bioorganic & Medicinal Chemistry Letters 2005 15, 3020-3023.*

D'Elios et. al. "Interfering with chemokines and chemokine receptors as potential new therapeutic strategies" Expert Opinion on Therapeutic Patents 2008, 18, 309-325.*

Dairaghi et al, *J. Biol. Chem.*, 272, 45 (1997) p. 28206-28209.

Ting, et al, The synthesis of substituted bipiperidine amide compounds . . . , Bioorganic & Medicinal Chemistry Letters 15 (2005), pp. 1375-1378.

* cited by examiner

*Primary Examiner*—Rita J Desai
*Assistant Examiner*—David K O'Dell
(74) *Attorney, Agent, or Firm*—Palaiyur S. Kalyanaraman; Serena Farquharson-Torres

(57) ABSTRACT

The use of CCR3 antagonists of the formula I

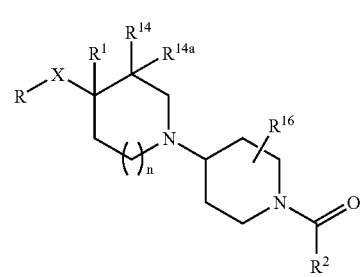

or a pharmaceutically acceptable salt thereof for the treatment of asthma is disclosed, as well as novel compounds of the formula II,

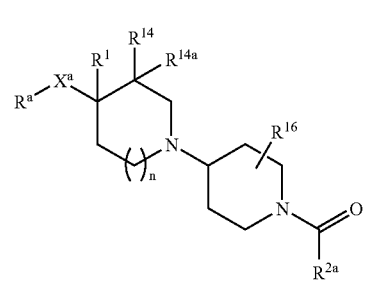

pharmaceutical compositions comprising them, and their use in the treatment of asthma, wherein R, $R^a$, X, $X^a$, $R^1$, $R^2$, $R^{2a}$, $R^{14}$, $R^{14a}$, $R^{16}$ and n are as defined in the specification.

19 Claims, No Drawings

BIPIPERDINE DERIVATIVES USEFUL AS CCR3 ANTAGONISTS

CROSS REFERENCE TO RELATED APPLICATION

This application claims the benefit of U.S. Provisional Application 60/542,013, filed Feb. 5, 2004.

BACKGROUND

The present invention relates to the use of piperidine derivatives as selective CCR3 antagonists for the treatment of asthma. The invention also relates to a genus of novel compounds useful as selective CCR3 antagonists, pharmaceutical compositions comprising the novel compounds, and methods of treatment using the novel compounds. Additional novel compounds having CCR3 antagonist activity are also claimed.

Piperidine derivatives useful as CCR3 antagonists are disclosed in WO 01/77101. Piperidine-derivative muscarinic antagonists useful in the treatment of cognitive disorders such as Alzheimer's disease are disclosed in U.S. Pat. Nos. 5,883,096; 6,037,352; 5,889,006; 5,952,349; and 5,977,138. Piperidine-derivative CCR5 antagonists useful in the treatment of HIV and inflammatory diseases such as rheumatoid arthtitis are disclosed in U.S. Pat. No. 6,387,930.

SUMMARY OF THE INVENTION

The present invention relates to the treatment of asthma comprising administering to a mammal in need of such treatment an effective amount of a CCR3 antagonist represented by the structural formula I:

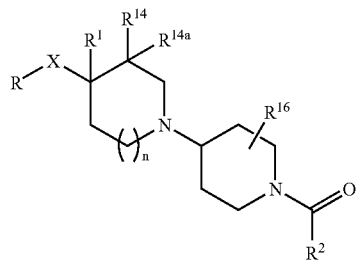

or a pharmaceutically acceptable salt thereof, wherein
n is 0 or 1;

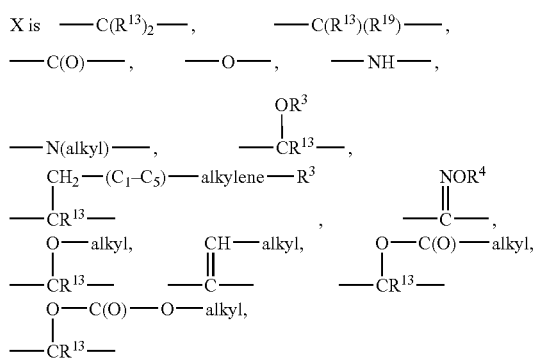

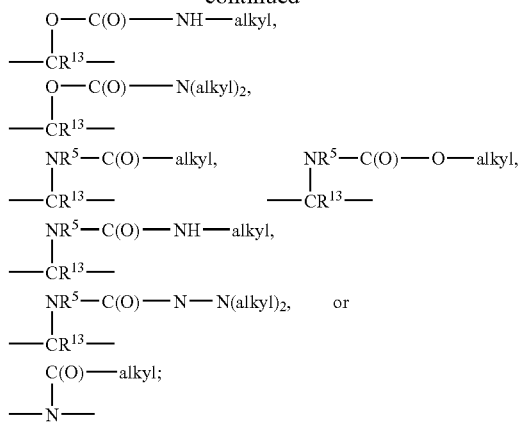

R is $R^6$-phenyl, $R^6$-pyridyl, $R^6$-thiophenyl or $R^6$-naphthyl;

$R^1$ is hydrogen, halogen, —OH, alkyl, hydroxyalkyl, alkoxy or alkoxyalkyl;

$R^2$ is $R^7$, $R^8$, $R^9$-substituted 6-membered heteroaryl; $R^7$, $R^8$, $R^9$-substituted 6-membered heteroaryl N-oxide; $R^{10}$, $R^{11}$-substituted 5-membered heteroaryl; $R^{12}$-naphthyl; fluorenyl; diphenylmethyl,

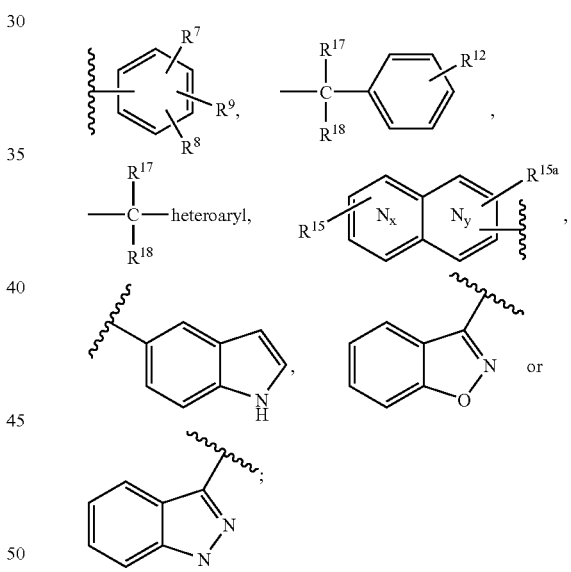

x is 0-2 and y is 0-2, provided that the sum of x and y is 1-4;

$R^3$ is $R^6$-phenyl, $R^6$-heteroaryl or $R^6$-naphthyl;

$R^4$ is hydrogen, alkyl, fluoroalkyl, cyclopropylmethyl, —$CH_2CH_2OH$, —$CH_2CH_2$—O-alkyl, —$CH_2C(O)$—O-alkyl, —$CH_2C(O)NH_2$, —$CH_2C(O)$—NH-alkyl or —$CH_2C(O)$—N(alkyl)$_2$;

$R^5$ and $R^{11}$ are independently selected from the group consisting of hydrogen and alkyl;

$R^6$ is 1 to 3 substituents independently selected from the group consisting of hydrogen, halogen, alkyl, alkoxy, —$CF_3$, $CF_3O$—, $CH_3C(O)$—, —CN, $CH_3SO_2$—, $CF_3SO_2$—, $R^{16}$-phenyl, $R^{16}$-benzyl, $CH_3C(=NOCH_3)$—, $CH_3C(=NOCH_2CH_3)$—,

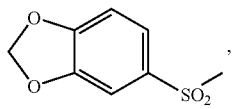

—NH$_2$, —NHCOCF$_3$, —NHCONH-alkyl, —NHCO-alkyl, —NHSO$_2$-alkyl, 5-membered heteroaryl and

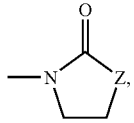

wherein Z is —O—, —NH— or —N(CH$_3$)—;

R$^7$ and R$^8$ are independently selected from the group consisting of alkyl, halogen, —NR$^{20}$R$^{21}$, —OH, —CF$_3$, —OCH$_3$, —O-acyl, and —OCF$_3$;

R$^9$ is R$^7$, hydrogen, phenyl, —NO$_2$, —CN, —CH$_2$F, —CHF$_2$, —CHO, —CH=NOR$^{20}$, pyridyl, pyridyl N-oxide, pyrimidinyl, pyrazinyl, —N(R$^{20}$)CONR$^{21}$R$^{22}$, —NHCONH (chloroalkyl), —NHCONH-cycloalkylalkyl, —NHCO-alkyl, —NHCOCF$_3$, —NHSO$_2$N(alkyl)$_2$, —NHSO$_2$-alkyl, —N(SO$_2$CF$_3$)$_2$, —NHCO$_2$-alkyl, cycloalkyl, —SR$^{23}$, —SOR$^{23}$, —SO$_2$R$^{23}$, —SO$_2$NH-alkyl, —OSO$_2$-alkyl, —OSO$_2$CF$_3$, hydroxyalkyl, —CON R$^{20}$R$^{21}$, —CON (CH$_2$CH$_2$—O—CH$_3$)$_2$, —OCONH-alkyl, —CO$_2$R$^{20}$, —Si (CH$_3$)$_3$ or —B(OC(CH$_3$)$_2$)$_2$;

R$^{10}$ is alkyl, —NH$_2$ or R$^{12}$-phenyl;

R$^{12}$ is 1 to 3 substituents independently selected from the group consisting of hydrogen, alkyl, —CF$_3$, —CO$_2$R$^{20}$, —CN, alkoxy and halogen;

R$^{13}$ and R$^{16}$ are independently selected from the group consisting of hydrogen and alkyl;

R$^{14}$ is alkyl, alkenyl, haloalkyl, hydroxy, hydroxyalkyl, —CN, —(CR$^{20}$R$^{21}$)$_q$—O-alkyl, —(CR$^{20}$R$^{21}$)$_q$—NR$^{20}$R$^{24}$, —(CR$^{20}$R$^{21}$)$_q$—N$_3$, —(CR$^{20}$R$^{21}$)$_q$—C(O)-alkyl, —(CR$^{20}$R$^{21}$)$_q$—C(O)-phenyl, —(CR$^{20}$R$^{21}$)$_q$—COOR$^{20}$, —(CR$^{20}$R$^{21}$)$_q$—C(O)NR$^{20}$R$^{24}$, —(CR$^{20}$R$^{21}$)$_q$—S(O)$_{0-2}$—R$^{23}$, —(CR$^{20}$R$^{21}$)$_q$—N(R$^{20}$)—C(O)NR$^{20}$R$^{24}$, —(CR$^{20}$R$^{21}$)$_q$—N(R$^{20}$)—C(O)OR$^{23}$ or —(CR$^{20}$R$^{21}$)$_q$—O—C(O)R$^{23}$;

R$^{14a}$ is hydrogen or alkyl;

or R$^{14}$ and R$^{14a}$ together form =O or =NOR$^{20}$;

or R$^{14}$ and R$^{14a}$, together with the ring carbon to which they are attached, form a spirocyclo ring of 3 to 6 carbon atoms;

q is 0, 1, 2 or 3;

R$^{15}$ and R$^{15a}$ are each 1 or 2 substituents independently selected from the group consisting of H, halogen, OH, alkyl, alkoxy, —CF$_3$, —OCF$_3$, —CN, —C(O)R$^{25}$, —COOR$^{25}$, —S(O)$_{0-2}$R$^{25}$, —S(O)$_{0-2}$CF$_3$, —NR$^{20}$R$^{24}$, phenyl and heterocycloalkyl; or two R$^{15}$ or two R$^{15a}$ substituents on adjacent ring carbon atoms, together with the carbons to which they are attached, form a fused 5-6 membered cycloalkyl ring;

R$^{17}$ and R$^{18}$ are independently selected from the group consisting of hydrogen and alkyl, or R$^{17}$ and R$^{18}$ together are a C$_2$-C$_5$ alkylene group and with the carbon to which they are attached form a cycloalkyl ring of 3 to 6 carbon atoms;

R$^{19}$ is R$^6$-phenyl, R$^6$-heteroaryl, R$^6$-naphthyl, cycloalkyl, cycloalkylalkyl or alkoxyalkyl;

R$^{20}$, R$^{21}$ and R$^{22}$ are independently selected from the group consisting of H and alkyl;

R$^{23}$ is alkyl or phenyl; and

R$^{24}$ is H, alkyl or R$^{12}$-phenyl.

Also claimed are novel CCR3 antagonist compounds represented by the structural formula II

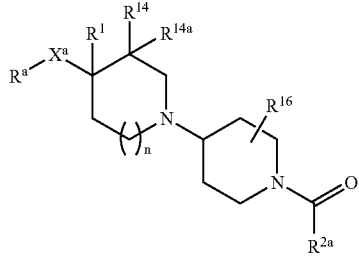

II or a pharmaceutically acceptable salt thereof, wherein
n is 0 or 1;

X$^a$ is —C(R$^{13}$)$_2$—, —C(O)— or —CR$^{13}$(OR$^{13}$)—;

R$^a$ is R$^{6a}$-phenyl, R$^{6a}$-pyridyl, R$^{6a}$-thiophenyl or R$^{6a}$-naphthyl;

R$^1$ is hydrogen, halogen, —OH, alkyl, hydroxyalkyl, alkoxy or alkoxyalkyl;

R$^{2a}$ is

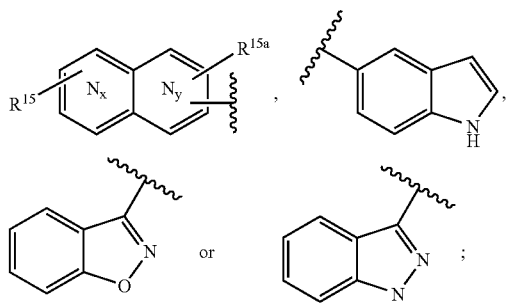

x is 0-2 and y is 0-2, provided that the sum of x and y is 1-4;

R$^{6a}$ is 1 to 3 substituents independently selected from the group consisting of hydrogen, halogen, —CF$_3$, CF$_3$O—, —CN, CF$_3$SO$_2$—, —NHCOCF$_3$, CH$_3$SO$_2$—, 5-membered heteroaryl and

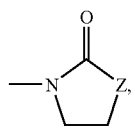

wherein Z is —O—, —NH— or —N(CH$_3$)—;

R$^{13}$ and R$^{16}$ are independently selected from the group consisting of hydrogen and alkyl;

R$^{14}$ is alkyl, alkenyl, haloalkyl, hydroxy, hydroxyalkyl, —CN, —(CR$^{20}$R$^{21}$)$_q$—O-alkyl, —(CR$^{20}$R$^{21}$)$_q$—NR$^{20}$R$^{24}$, —(CR$^{20}$R$^{21}$)$_q$—N$_3$, —(CR$^{20}$R$^{21}$)$_q$—C(O)-alkyl, —(CR$^{20}$R$^{21}$)$_q$—C(O)-phenyl, —(CR$^{20}$R$^{21}$)$_q$—COOR$^{20}$, —(CR²⁰R²¹)_q—C(O)NR²⁰R²⁴, —(CR²⁰R²¹)_q—S(O)_{0-2}—R²³, —(CR²⁰R²¹)_q—N(R²⁰)—C(O)NR²⁰R²⁴, —(CR²⁰R²¹)_q—N(R²⁰)—C(O)OR²³ or —(CR²⁰R²¹)_q—O—C(O)R²³;

R¹⁴ᵃ is hydrogen or alkyl;
or R¹⁴ and R¹⁴ᵃ together form =O or =NOR²⁰;

or R¹⁴ and R¹⁴ᵃ, together with the ring carbon to which they are attached, form a spirocyclo ring of 3 to 6 carbon atoms;
q is 0, 1, 2 or 3;
R¹⁵ and R¹⁵ᵃ are each 1 or 2 substituents independently selected from the group consisting of H, halogen, OH, alkyl, alkoxy, —CF₃, —OCF₃, —CN, —C(O)R²⁵, —COOR²⁵, —S(O)_{0-2}R²⁵, —S(O)_{0-2}CF₃, —NR²⁰R²⁴, phenyl and heterocycloalkyl; or two R¹⁵ or two R¹⁵ᵃ substituents on adjacent ring carbon atoms, together with the carbons to which they are attached, form a fused 5-6 membered cycloalkyl ring;

R²⁰ and R²¹ are independently selected from the group consisting of H and alkyl;

R²³ is alkyl or phenyl; and
R²⁴ is H, alkyl R¹²-phenyl; provided that when R¹⁴ is —(CR²⁰R²¹)_q—NR²⁰R²⁴ and R²⁴ is H, R²⁰ is alkyl.

Another aspect of the invention is the method of treating asthma comprising administering to a mammal in need of such treatment an effective amount of a compound of formula II.

Another aspect of the invention is a pharmaceutical composition for treatment of asthma comprising an effective amount of a CCR3 antagonist of formula II in combination with a pharmaceutically acceptable carrier.

Also claimed are the following novel compounds in the genus of formula I:

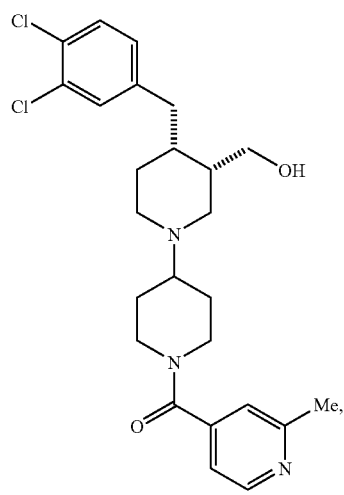

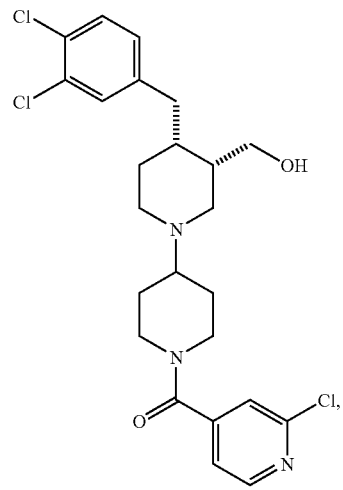

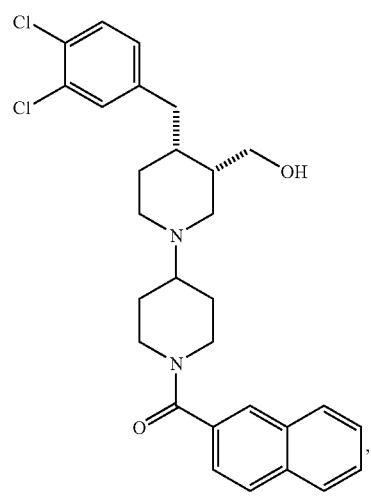

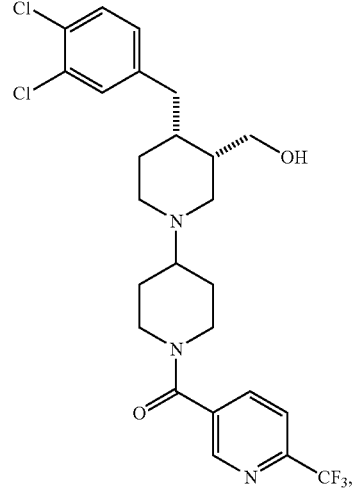

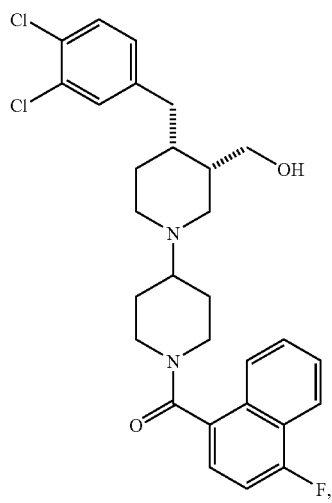
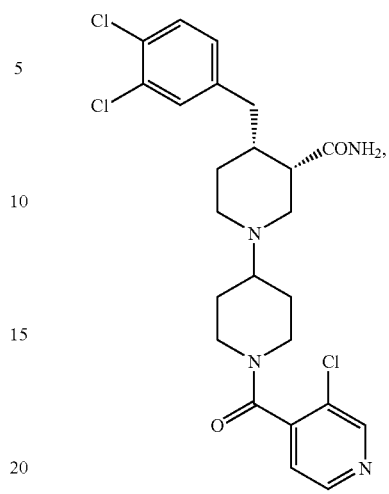
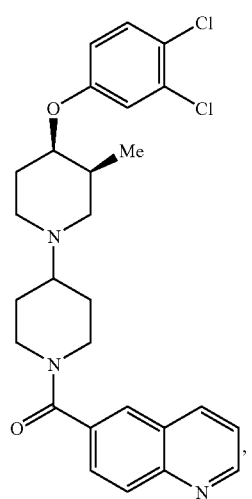
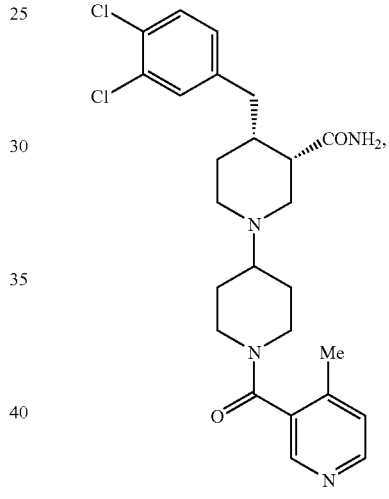
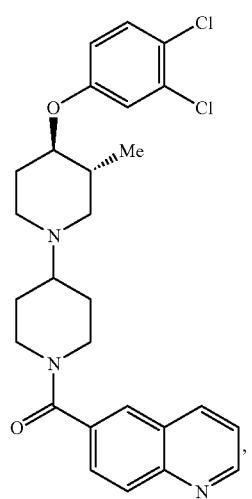
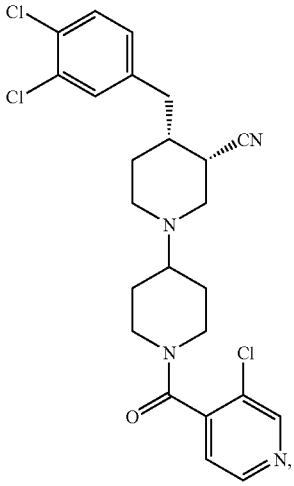

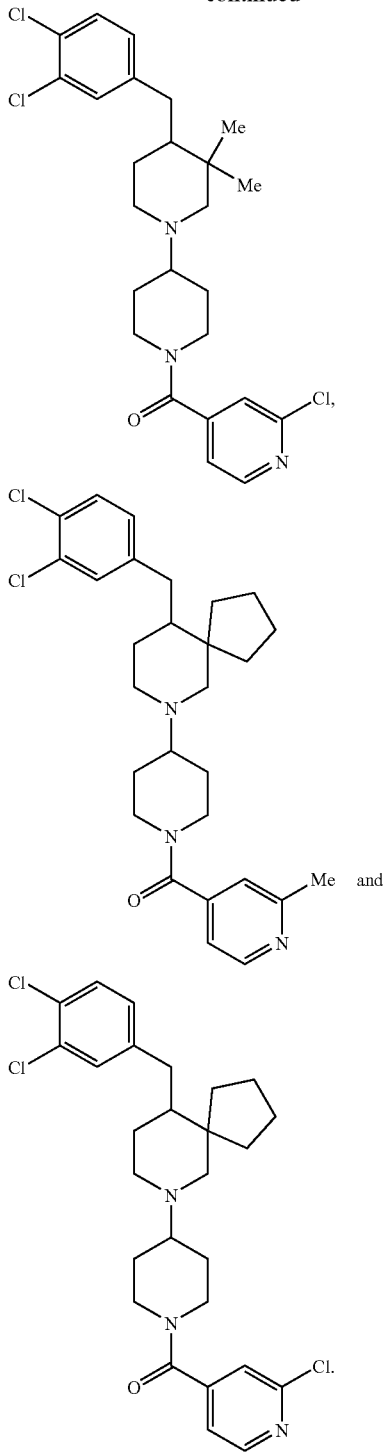

DETAILED DESCRIPTION OF THE INVENTION

Preferred are compounds of formula I wherein n is 1. Preferably, R is $R^6$-phenyl, especially wherein $R^6$ is one or two, preferably two halogen substituents. A preferred halogen substituent is chloro. Also preferred are compounds of formula I wherein $R^{16}$ is hydrogen. Also preferred are compounds of formula I wherein X is —C($R^{13}$)($R^{13}$)—, especially wherein $R^{13}$ is hydrogen. For compounds of formula I, $R^1$ is preferably hydrogen. $R^{14}$ is preferably alkyl, haloalkyl, hydroxy, hydroxyalkyl, alkoxy or alkoxyalkyl and $R^{14a}$ is preferably hydrogen.

In compounds of formula I, $R^2$ is preferably $R^7$, $R^8$, $R^9$-substituted 6-membered heteroaryl, $R^{12}$-naphthyl,

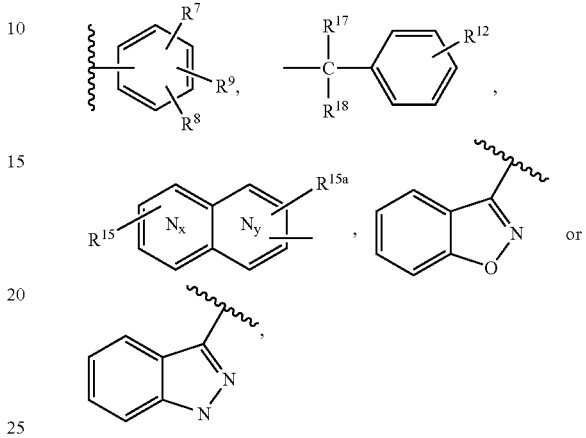

wherein $R^7$, $R^8$, $R^9$, $R^{12}$, $R^{17}$ and $R^{18}$ are as defined above and wherein the sum of x and y is 1 or 2, more preferably 1 (i.e., $R^2$ is optionally substituted quinolyl). $R^{15}$ and $R^{15a}$ are preferably single substituents, both of which are hydrogen, or $R^{15}$ and $R^{15a}$ are single substituents independently selected from the group consisting of hydrogen, halogen, methyl, methoxy and $CF_3$.

Preferred are compounds of formula II wherein n is 1. Preferred are compounds of formula II wherein $R^a$ is $R^{6a}$-phenyl, especially wherein $R^{6a}$ is one or two, preferably two halogen substituents. A preferred halogen substituent is chloro.

Also preferred are compounds of formula II wherein $R^{16}$ is hydrogen. Also preferred are compounds of formula II wherein $X^a$ is —C($R^{13}$)($R^{13}$)—, especially wherein each $R^{13}$ is hydrogen. For compounds of formula II, $R^1$ is preferably hydrogen.

In another embodiment of formula II, $R^{14}$ is preferably alkyl, haloalkyl, hydroxy, hydroxyalkyl, alkoxy or alkoxyalkyl and $R^{14a}$ is hydrogen.

In compounds of formula II, $R^{2a}$ is preferably

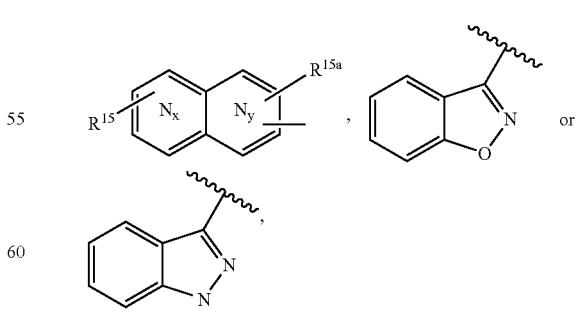

wherein the sum of x and y is 1 or 2, more preferably 1 (i.e., $R^{2a}$ is optionally substituted quinolyl). More preferred $R^{2a}$ substituents are selected from the group consisting of

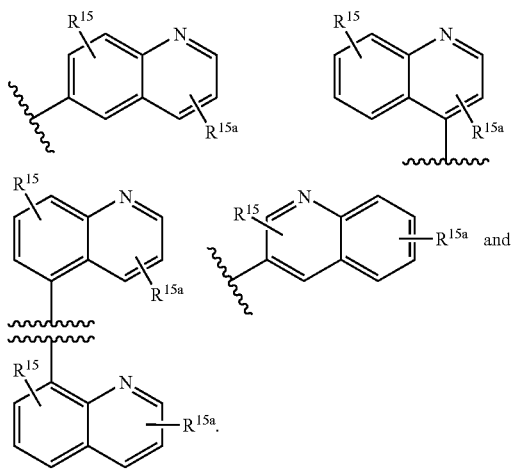

$R^{15}$ and $R^{15a}$ are preferably single substituents, both of which are hydrogen, or $R^{15}$ and $R^{15a}$ are single substituents independently selected from the group consisting of hydrogen, halogen, methyl, methoxy and $CF_3$.

For compounds of both formulas I and II, $R^{14}$ is preferably in the "cis" form relative to R—X or $R^a$—$X^a$, that is compounds of formulas I and II are preferably as shown in the following partial structures

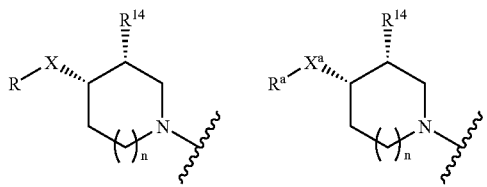

(wherein $R^{14}$ and $R^1$ are exemplified as hydrogen).

As used herein, the following terms are used as defined below unless otherwise indicated.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, t-butyl, n-pentyl, heptyl, nonyl, and decyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Halogen" or "halo" represents fluoro, chloro, bromo and iodo.

"Haloalkyl" means an alkyl as defined above wherein one or more hydrogen atoms on the alkyl is replaced by a halo group defined above. Chloroalkyl and fluoroalkyl refer to alkyl groups substituted by either chloro or fluoro groups, respectively, for example fluoroalkyl represents a straight or branched alkyl chain substituted by 1 to 5 fluoro atoms, which can be attached to the same or different carbon atoms, e.g., —$CH_2F$, —$CHF_2$, —$CF_3$, —$CH_2CF_3$ and —$CF_2CF_3$.

"Hydroxyalkyl" means a HO-alkyl-group in which alkyl is as previously defined. Non-limiting examples of suitable hydroxyalkyl groups include hydroxymethyl, 2-hydroxyethyl and 1-hydroxyethyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

Acyl means a radical of a carboxylic acid having the formula alkyl-C(O)—, aryl-C(O)—, aralkyl-C(O)—, cycloalkyl-C(O)—, cycloalkylalkyl-C(O)—, and heteroaryl-C(O)—, wherein alkyl and heteroaryl are as defined herein; aryl is $R^{12}$-phenyl or $R^{12}$-naphthyl; and aralkyl is arylalkyl, wherein aryl is as defined above.

"Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

Heteroaryl represents cyclic aromatic groups of 5 or 6 atoms or bicyclic groups of 11 to 12 atoms having 1 or 2 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. For 6-membered heteroaryl rings, carbon atoms can be substituted by $R^7$, $R^8$ or $R^9$ groups. Nitrogen atoms can form an N-oxide. All regioisomers are contemplated, e.g., 2-pyridyl, 3-pyridyl and 4-pyridyl. Typical 6-membered heteroaryl groups are pyridyl, pyrimidinyl, pyrazinyl, pyridazinyl and the N-oxides thereof. For 5-membered heteroaryl rings, carbon atoms can be substituted by $R^{10}$ or $R^{11}$ groups. Typical 5-membered heteroaryl rings are furyl, thienyl, pyrrolyl, thiazolyl, isothiazolyl, imidazolyl, pyrazolyl and isoxazolyl. 5-Membered rings having one heteroatom can be joined through the 2- or 3-position; 5-membered rings having two heteroatoms are preferably joined through the 4-position. Bicyclic groups typically are benzo-fused ring systems derived from the heteroaryl groups named above, e.g. quinolyl, phthalazinyl, quinazolinyl, benzofuranyl, benzothienyl and indolyl.

As used herein, the term "composition" is intended to encompass a product comprising the specified ingredients in the specified amounts, as well as any product which results, directly or indirectly, from combination of the specified ingredients in the specified amounts.

The wavy line ∼∼∼ as a bond generally indicates a mixture of, or either of, the possible isomers, e.g., containing (R)- and (S)-stereochemistry. For example,

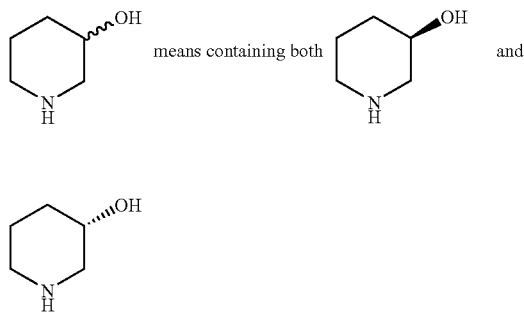

Lines drawn into the ring systems, such as, for example:

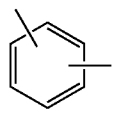

indicate that the indicated line (bond) may be attached to any of the substitutable ring carbon atoms. When reference is made to a substituted ring, e.g., phenyl, the substitution can be at any available position on the phenyl ring.

As well known in the art, a bond drawn from a particular atom wherein no moiety is depicted at the terminal end of the bond indicates a methyl group bound through that bond to the atom, unless stated otherwise. For example:

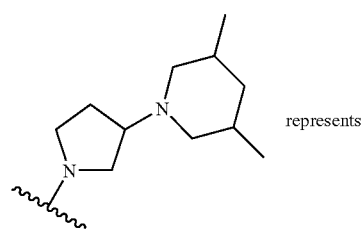 represents

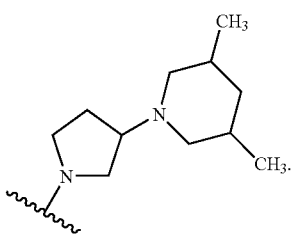

It should also be noted that any carbon or heteroatom with unsatisfied valences in the text, schemes, examples, structural formulae, and any tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting CCR3 receptors and thus producing the desired therapeutic effect in a suitable patient.

When $R^2$ is $R^7$, $R^8$, $R^9$-phenyl; $R^7$, $R^8$, $R^9$-substituted 6-membered heteroaryl; or $R^7$, $R^8$, $R^9$-substituted 6-membered heteroaryl N-oxide, the $R^7$ and $R^8$ substituents are preferably attached to carbon ring members adjacent to the carbon joining the ring to the rest of the molecule and the $R^9$ substituent can be attached to any of the remaining unsubstituted carbon ring members, for example as shown in the following structures:

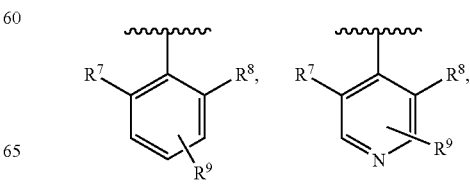

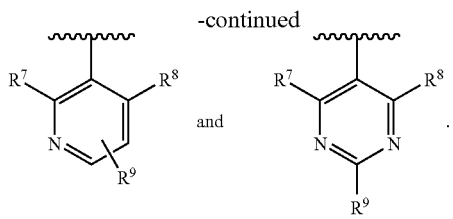

When R² is a 5-membered heteroaryl group, the R¹⁰ and R¹¹ substituents are preferably attached to carbon ring members adjacent to the carbon joining the ring to the rest of the molecule, and R¹¹ is preferably alkyl; however, if a heteroatom is adjacent to the carbon joining the ring to the rest of the molecule (i.e., as in 2-pyrrolyl), R¹⁰ is preferably attached to a carbon ring member adjacent to the carbon joining the ring to the rest of the molecule.

When R² or R²ᵃ is of the formula in addition to the quinolyl groups disclosed above as preferred, typical rings include, isoquinolyl, phthalazinyl, naphthyridinyl, quinoxalinyl, quinazolinyl, cinnolinyl, pteridinyl, pyridopyridazine, or pyridopyridine. An example of two R¹⁵ or two R¹⁵ᵃ substituents forming a fused ring is shown by the following structure:

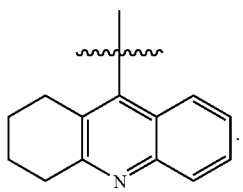

Certain CCR3 antagonist compounds of the invention may exist in different isomeric (e.g., enantiomers, diastereoisomers and atropisomers) forms. The invention contemplates all such isomers both in pure form and in admixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Polymorphic forms of the compounds of Formulas I and II, and of the salts, solvates and prodrugs of the compounds of Formula I and II, are intended to be included in the present invention.

Compounds of the invention can be made by the procedures known in the art, in particular by the methods described in U.S. Pat. No. 6,387,930, incorporated herein by reference, as well as by the method described in U.S. Pat. Nos. 5,883,096; 6,037,352; 5,889,006; 5,952,349; and 5,977,138, also incorporated herein by reference.

Compounds useful in this invention are exemplified by the following preparative examples, which should not be construed to limit the scope of the disclosure. Alternative mechanistic pathways and analogous structures within the scope of the invention may be apparent to those skilled in the art.

The following solvents and reagents may be referred to in the examples by these abbreviations: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxy-benzotriazole (HOBT); m-chloroperbenzoic acid (MCPBA); triethylamine (Et₃N); diethyl ether (Et₂O); tert-butoxy-carbonyl (BOC); 9-boracyclo[3.3.1]nonane (9-BBN); 1,8-diazabicyclo[5.4.0]undec-7-ene (DBU); dimethyl-sulfoxide (DMSO); p-toluene sulfonic acid (p-TSA); 4-dimethylaminopryidine (DMAP); N,N,N-diisopropylethylamine (Dipea); and tert-butyldiphenylsilyl chloride (TBDPS-CI). RT is room temperature.

Enantiomers are separated on Chiral Technology AD columns using 10% isopropanol-hexane with 0.5% diethylamine to 30% isopropanol-hexane with 0.5% diethylamine as eluant.

In the following examples, the "Step" numbers refer to certain procedures, and each time that procedure is used, the same step number is repeated; this results in non-consecutive numbering of steps in the later examples.

Example 1
General Procedure
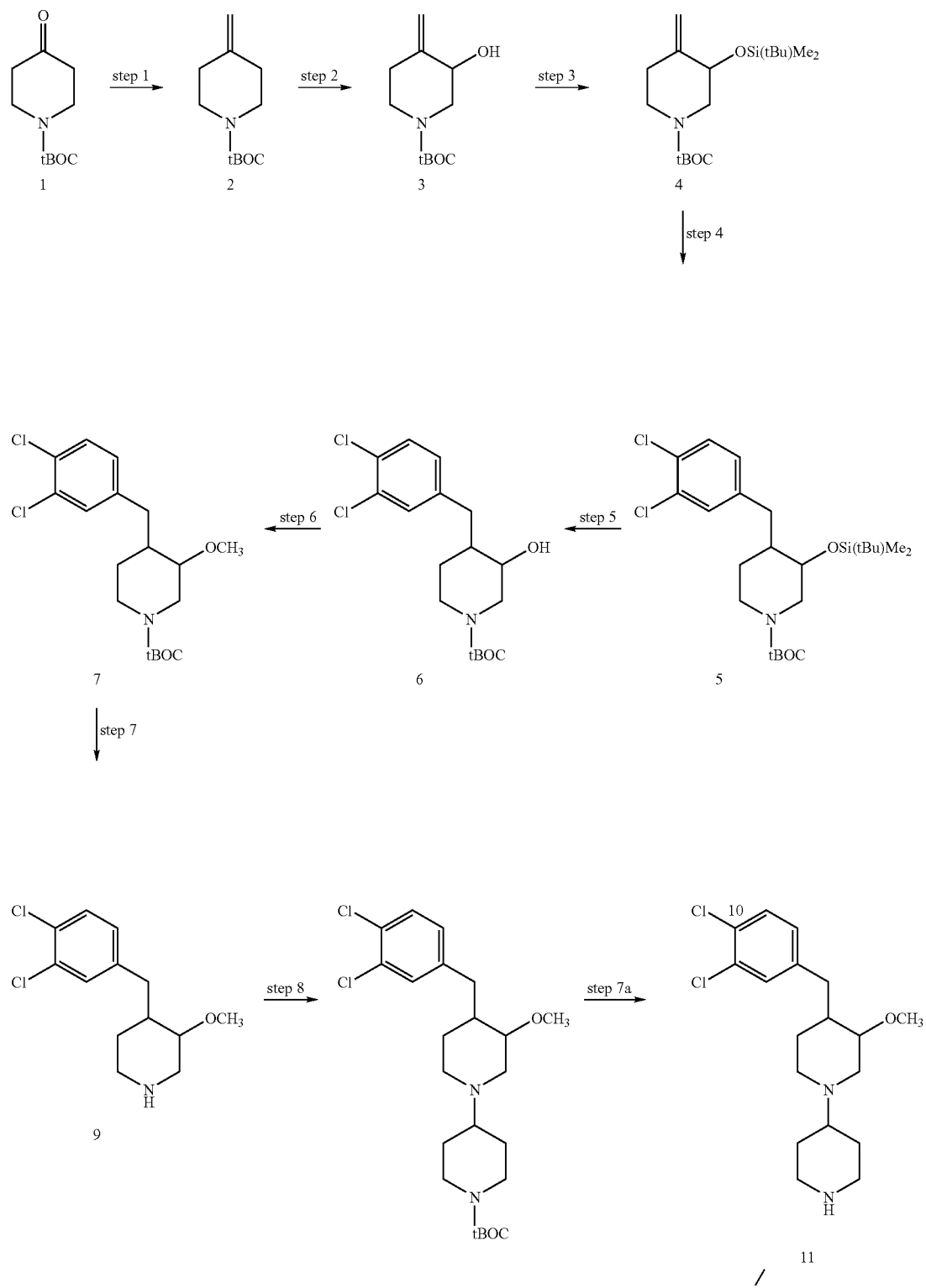

-continued

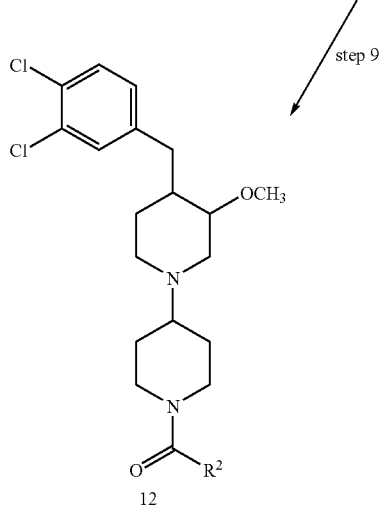

step 9

12

Step 1:

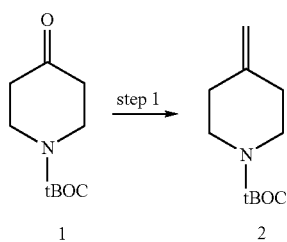

Methyl triphenylphosphonium bromide (38.0 g, 0.106 mol) was suspended in dry THF (250 ml) and cooled to −78° C. under nitrogen. n-Butyl lithium (50.0 ml, 0.100 mol, 2.0 M in cyclohexane) was added dropwise via addition funnel. The cooling bath was removed and the mixture was stirred at 23° C. for 45 mins. 1-t-Butoxycarbonyl-4-piperidone 1 (17.5 g, 0.088 mol) dissolved in dry THF (20 ml) was added dropwise via addition funnel. The mixture was stirred at 23° C. for 3 h, refluxed for 16 h, then cooled to 23° C. The solid was filtered off, washed with Et$_2$O, and the solvent was evaporated. The resultant residue was triturated 3× with Et$_2$O, the solid was filtered off, washed with Et$_2$O, and the solvent was evaporated. The crude product was purified by silica gel chromatography (eluant: 1:8 EtOAc:hexane) to give 14.0 g (0.071 mol, 79%) of the product 2 as a colorless oil. MS (ES for M+1): m/e 198.

Step 2:

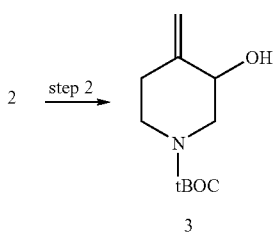

Selenium dioxide (2.81 g, 0.0253 mol) was suspended in CH$_2$Cl$_2$ (150 ml) and cooled to 0° C. t-Butylhydroperoxide (13.9 ml, 0.101 mol, 70% in water) was added and the mixture stirred at 0° C. for 30 mins. Compound 2 (10.0 g, 0.0507 mol) in CH$_2$Cl$_2$ (20 ml) was added and the mixture was stirred at 0° C. for 60 mins, then at 23° C. for 16 h. Ice chips and 10% by weight sodium bisulfite in water (150 ml) were added. The layers were separated and the aqueous layer was extracted with CH$_2$Cl$_2$. The combined organic extracts were dried (MgSO$_4$), filtered, and concentrated. Purification by silica gel chromatography (eluant: 25% EtOAc-hexane to 50% EtOAc-hexane) gave 5.26 g (0.0247 mol, 49%) of the product 3 as a yellow oil. MS (FAB for M+1): m/e 214.

Step 3:

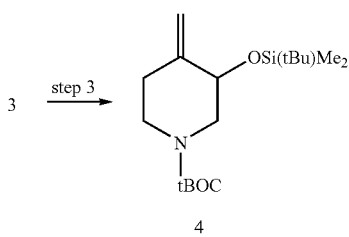

Compound 3 (5.25 g, 24.6 mmol) was dissolved in CH$_2$Cl$_2$, and Et$_3$N (3.74 g, 5.1 mL, 36.9 mmol), DMAP (0.75 g, 6.15 mmol), and t-butyldimethylsilyl chloride (4.64 g, 30.77 mmol) were added. The mixture was stirred at 23° C. for 16 h. Water (150 ml) was added and the layers were separated. The aqueous layer was extracted with CH$_2$Cl$_2$. The combined organic extracts were dried (MgSO$_4$), filtered, and concentrated. Purification by silica gel chromatography (eluant: 1:4 EtOAc:hexane) gave 7.43 g (22.7 mmol, 92%) of the product 4 as a light yellow oil. MS (FAB for M+1): m/e 328.

Step 4:

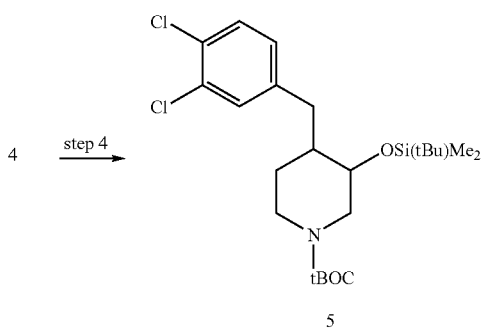

Compound 4 (7.42 g, 22.65 mmol) was dissolved in 9-BBN in THF solution (0.5 N, 68.0 ml, 34.0 mmol) and refluxed under nitrogen for 4 h, then cooled to 23° C. 1,2-Dichloro-4-iodobenzene (9.27 g, 34.0 mmol), $K_2CO_3$ (4.70 g, 34.0 mmol), and 1,1'-bis(diphenylphosphino)ferrocene) dichloropalladium II (1.85 g, 2.27 mmol), DMF (60 ml), and water (4 ml) were added and the mixture was heated in 90° C. oil bath for 16 h. The reaction mixture was concentrated, 0.5 N NaOH (100 ml) was added, and the resultant mixture extracted with $CH_2Cl_2$. The combined organic extracts were dried ($MgSO_4$), filtered, and concentrated. Purification by silica gel chromatography (eluant: 5% EtOAc-hexane to 10% EtOAc-hexane) gave 4.13 g (8.72 mmol, 38%) of the trans isomer of the product 5 as a white waxy solid and 3.83 g (8.09 mmol, 36%) of the cis isomer of the product 5 as a colorless oil. MS (FAB for M+1): m/e 474.

Step 5:

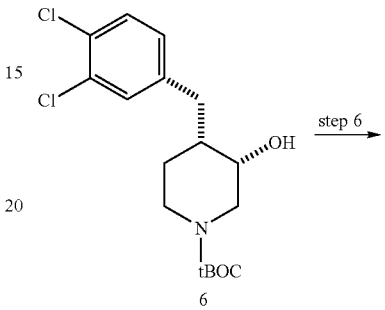

Compound 5 (8.00 g, 16.9 mmol) was dissolved in THF (60 ml) and tetra-n-butylammonium fluoride in THF (1.0 M, 25.4 mL, 25.4 mmol) was added. The mixture was stirred at 23° C. for 16 h, then concentrated. Water (100 ml) was added and the mixture was extracted with $CH_2Cl_2$. The combined organic extracts were dried ($MgSO_4$), filtered, and concentrated. Purification by silica gel chromatography (eluant: 5% EtOAc-hexane to 20% EtOAc-hexane) gave 5.80 g (16.1 mmol, 95%) of the product 6 as a colorless oil. MS (FAB for M+1): m/e 360.

Step 6:

Compound 6 (3.80 g, 10.5 mmol) was dissolved in dry DMF (70 ml) and cooled to 0° C. under nitrogen. Potassium bis(trimethylsilyl)amide (27.4 ml, 13.7 mmol, 0.5 M in toluene) was added and the mixture was stirred at 0° C. for 30 mins. $CH_3I$ (2.25 g, 0.98 ml, 15.8 mmol) was added, the mixture was allowed to warm up slowly, and was stirred at 23° C. for 16 h. The reaction mixture was concentrated, 0.5 N NaOH (70 ml) was added, and the mixture extracted with $CH_2Cl_2$. The combined organic extracts were dried ($MgSO_4$), filtered, and concentrated. Purification by silica gel chromatography (eluant: 5% EtOAc-hexane to 10% EtOAc-hexane) gave 3.20 g (8.55 mmol, 81%) of the product 7A as a colorless oil. MS (FAB for M+1): m/e 374.

Step 7:

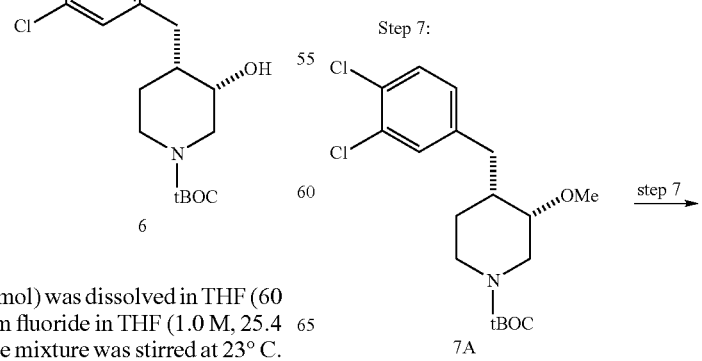

-continued

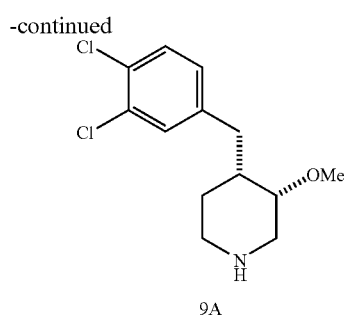

9A

Compound 7A (5.90 g, 0.0158 mol) was dissolved in 1:1 CH$_2$Cl$_2$:MeOH (150 ml), cooled to 0° C., and 4 N HCl in dioxane (31.5 ml, 0.126 mol) was added. The mixture was stirred at 23° C. for 16 h, and concentrated. MeOH (200 ml) was added and the mixture was made basic with diethylaminomethylpolystyrene resin. The resultant mixture was filtered, the resin washed with MeOH, and the solvent removed under vacuum to give 4.30 g (0.0158 mol, 100%) of the product 9A as a tan foam. MS (FAB for M+1): m/e 274.

Step 8:

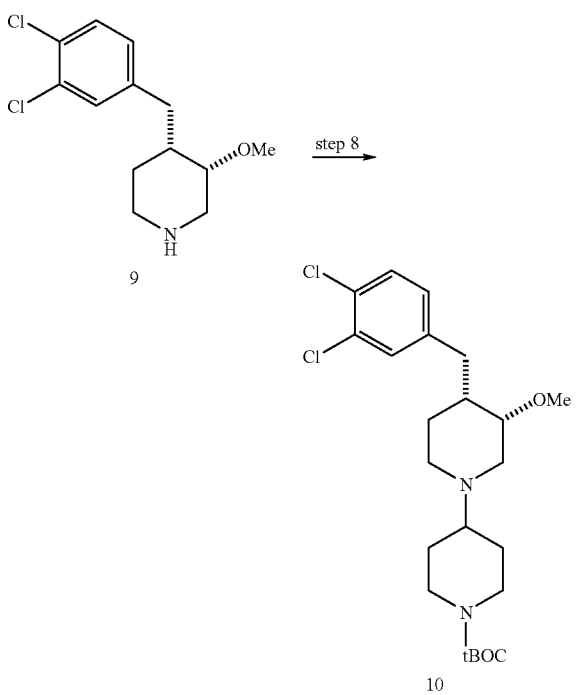

Compound 9 (4.70 g, 17.1 mmol) was dissolved in dry CH$_2$Cl$_2$ (250 ml), 1-t-butoxycarbonyl-4-piperidone (5.10 g, 25.7 mmol), 3 Å sieves (3 g), sodium triacetoxyborohydride (7.30 g, 34.3 mmol), and AcOH (1.02 g, 0.94 ml, 17.1 mmol) were added, and the mixture stirred at 23° C. for 16 h. 0.5 N NaOH (200 ml) was added, the mixture was filtered and then extracted with CH$_2$Cl$_2$. Combined organic extracts were dried (MgSO$_4$), filtered, and concentrated. To remove 1-t-butoxycarbonyl-4-hydroxypiperidine, the crude product was dissolved in CH$_2$Cl$_2$ (200 ml) and Et$_3$N (3.47 g, 4.8 ml, 34.3 mmol), DMAP (1.05 g, 8.57 mmol), and acetyl chloride (1.35 g, 1.2 ml, 17.1 mmol) were added. The mixture was stirred at 23° C. for 16 h. Water (150 ml) was added and the mixture was extracted with CH$_2$Cl$_2$. Combined organic extracts were dried (MgSO$_4$), filtered, and concentrated. Purification by silica gel chromatography (eluant: EtOAc then 5% MeOH with NH$_3$—CH$_2$Cl$_2$) gave 5.20 g (11.4 mmol, 66%) of the product 10 as a brown oil. MS (FAB for M+1): m/e 457.

Step 7a:

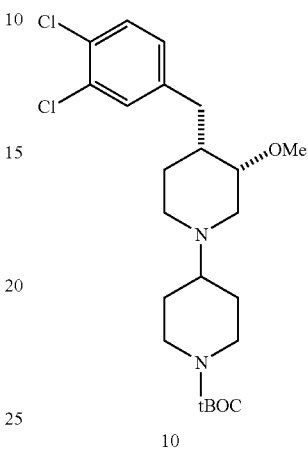

10

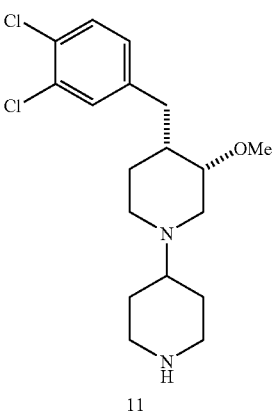

11

The same procedure as used above for Step 7 was used to prepare compound 11 from compound 10. MS (ES for M+1): m/e 357.

Step 9:

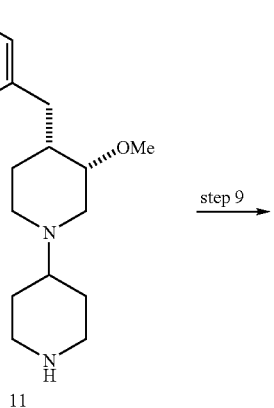

11

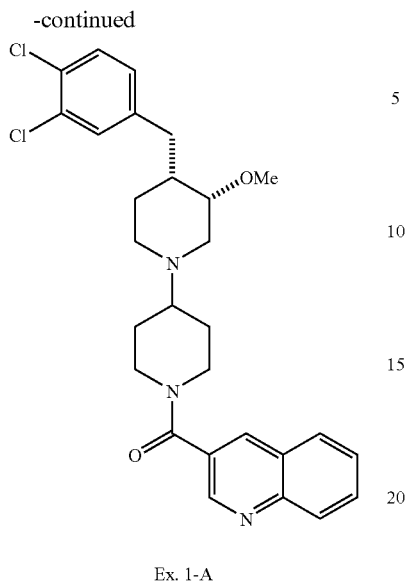

Ex. 1-A

Compound 11 (0.15 g, 0.42 mmol) was combined with 3-quinolinecarboxylic acid (0.11 g, 0.63 mmol), HOBT (0.085 g, 0.63 mmol), 1-ethyl-3-(3-dimethylaminopropyl) carbodiimide (0.16 g, 0.84 mmol), and Dipea (0.11 g, 0.84 mmol) in 1:1 $CH_2Cl_2$:DMF (8 ml) and the mixture was refluxed for 16 h, then cooled to 23° C. 0.5 N NaOH (10 ml) was added, and the mixture was filtered and extracted with $CH_2Cl_2$. Combined organic extracts were dried ($MgSO_4$), filtered, and concentrated. Purification by silica gel chromatography (eluant: 3% MeOH with $NH_3$—$CH_2Cl_2$) gave 0.13 g (0.25 mmol, 62%) of the product Example 1A as a yellow foam. MS (FAB for M+1): m/e 512.

The following compounds were prepared according to a similar procedure:

| Ex. | Structure | MS (CI, FAB, or ES) |
|---|---|---|
| 1-B | | 512 diastereomer and enantiomers A and B |
| 1-C | 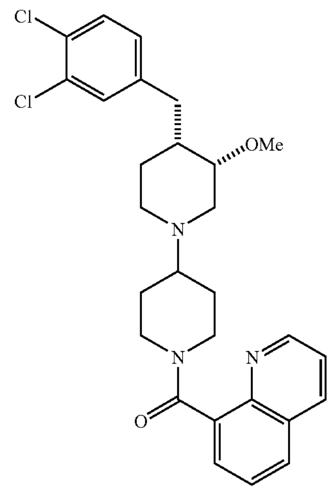 | 512 |
| 1-D | 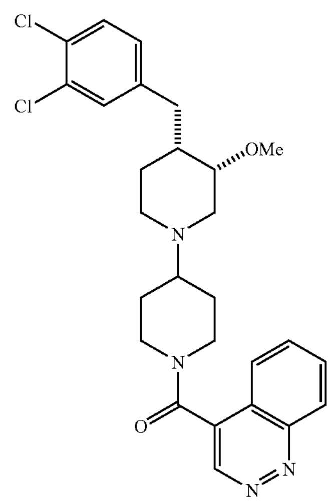 | 513 |
| 1-E | 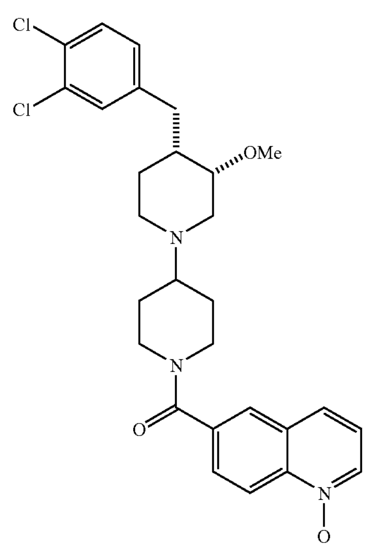 | 528.5 |

-continued
| Ex. | Structure | MS (Cl, FAB, or ES) |
|---|---|---|
| 1-F | 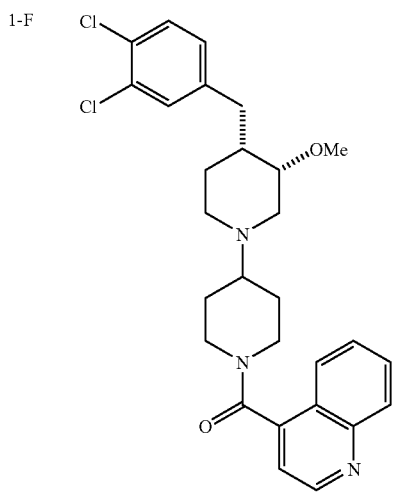 | 512 |
| 1-G | 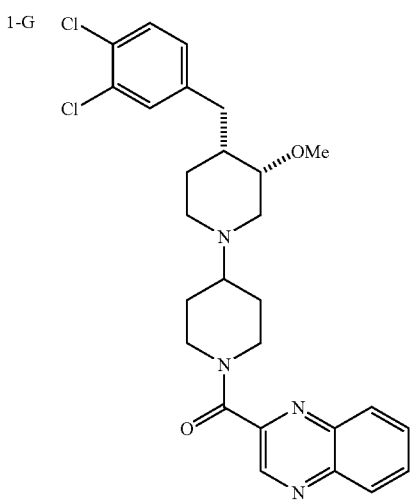 | 513 |
| 1-H | 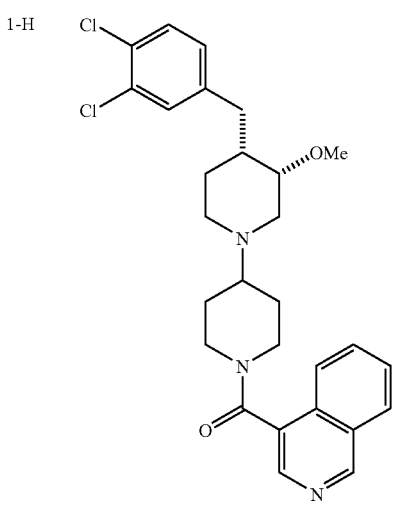 | 512 |
-continued
| Ex. | Structure | MS (Cl, FAB, or ES) |
|---|---|---|
| 1-I | 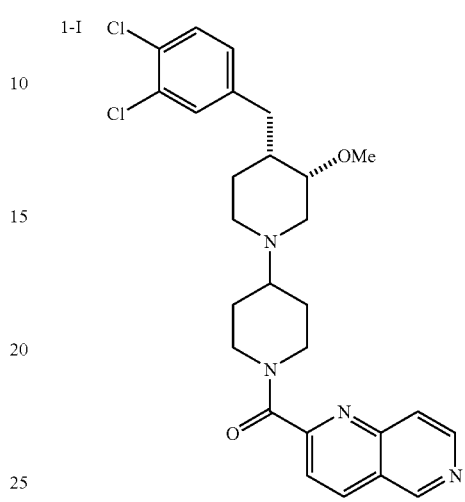 | 513 |
| 1-J | 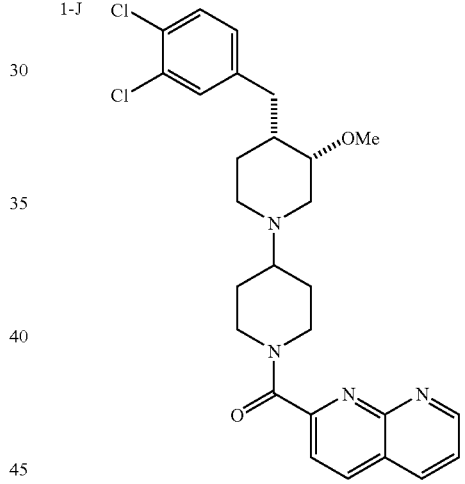 | 513 |
| 1-K | 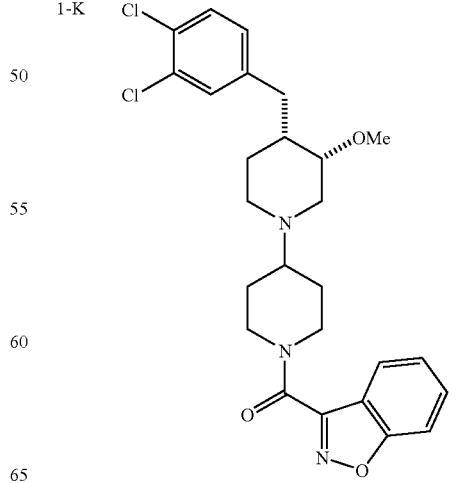 | 501 |

-continued
| Ex. | Structure | MS (Cl, FAB, or ES) |
|---|---|---|
| 1-L | 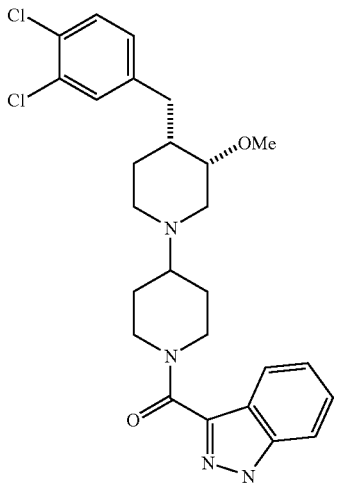 | 501 |
| 1-M | 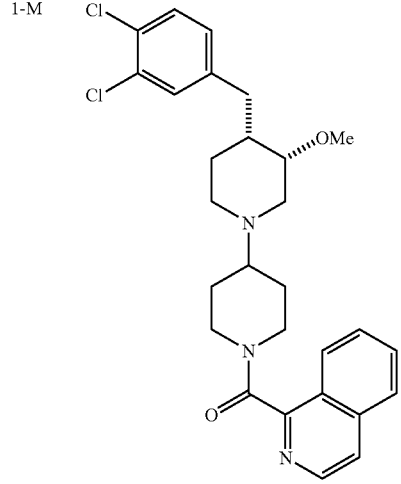 | 512 |
| 1-N | 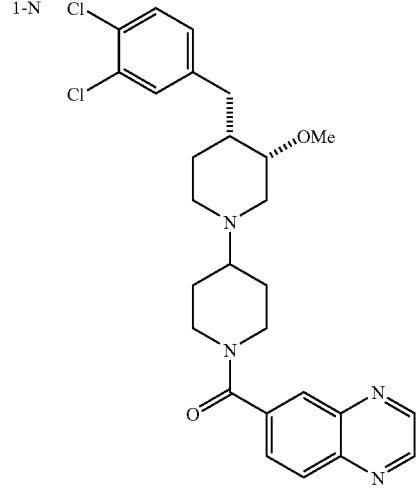 | 513 |
-continued
| Ex. | Structure | MS (Cl, FAB, or ES) |
|---|---|---|
| 1-O | 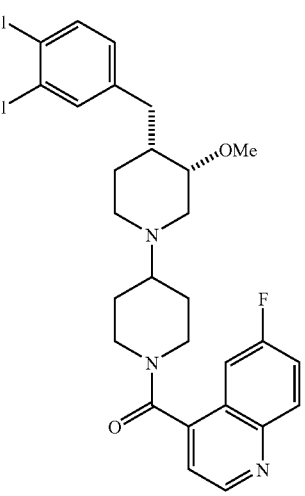 | 530 |
| 1-P | 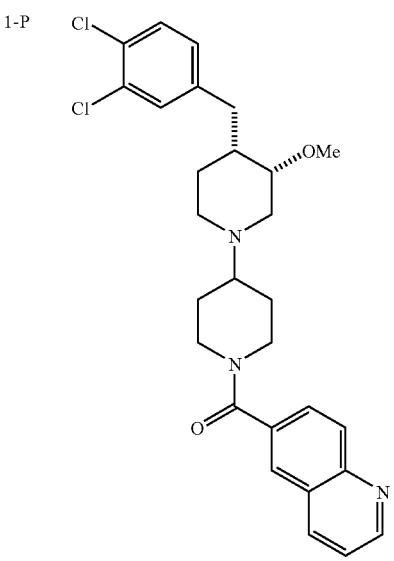 | 526 trans enantiomer C, nl cis enantiomer D, trans enantiomer A, cis enantiomer B |
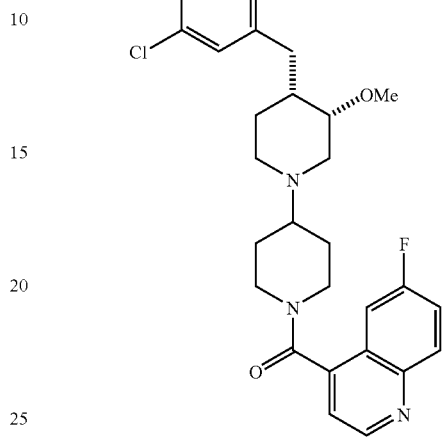

Example 2
General Procedure
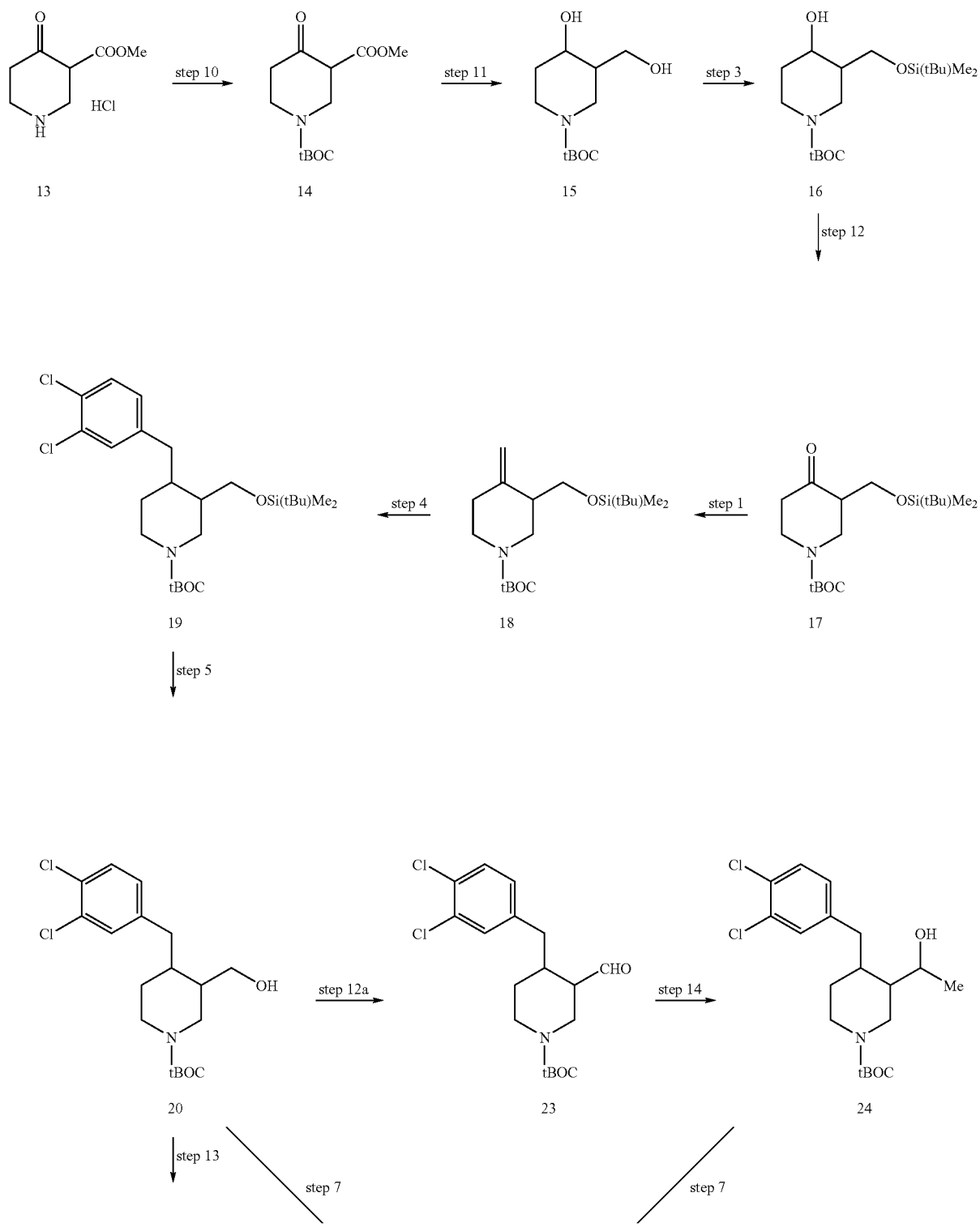

-continued

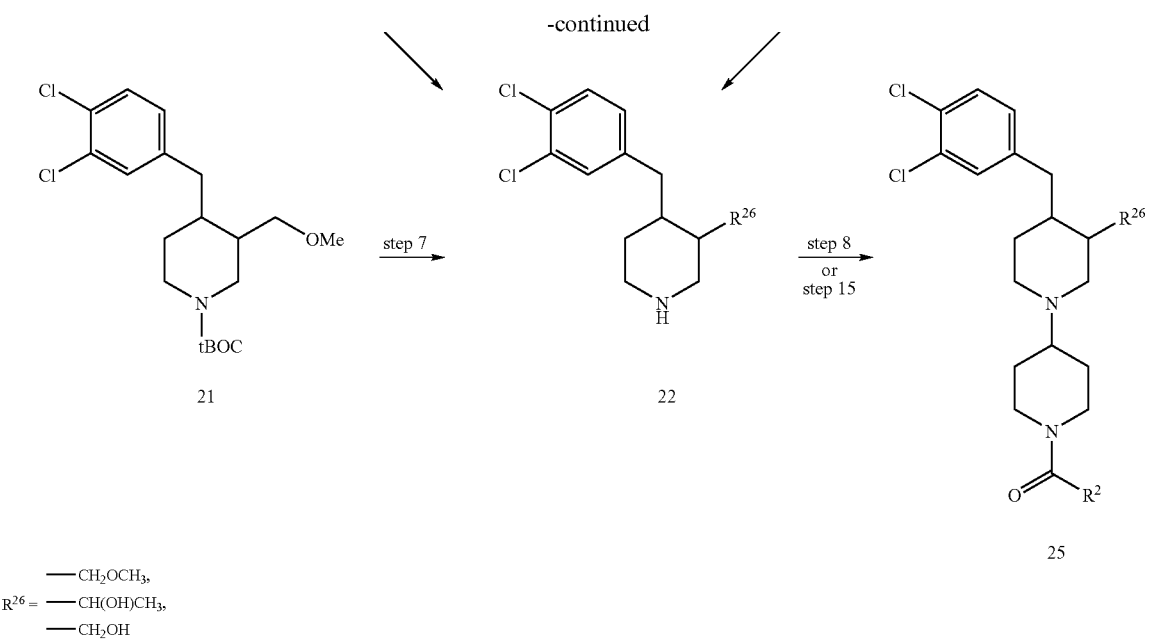

$R^{26} = $ —CH$_2$OCH$_3$,
—CH(OH)CH$_3$,
—CH$_2$OH

Step 10:

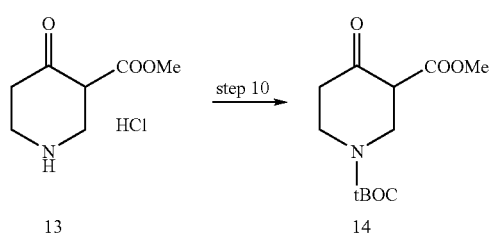

Compound 13 (25.0 g, 0.129 mol), di-t-butyl dicarbonate (33.8 g, 0.155 mol), and Et$_3$N (26.1 g, 36.0 ml, 0.258 mol) were combined in CH$_2$Cl$_2$ (240 ml) and MeOH (60 ml), stirred at 23° C. for 16 h and concentrated. 1.0 N NaOH (100 ml) was added and the mixture extracted with CH$_2$Cl$_2$. The combined organic extracts were dried (MgSO$_4$), filtered, and concentrated. Purification by silica gel chromatography (eluant: 5% EtOAc-hexane, to 10% EtOAc-hexane) gave 33.2 g (0.129 mol, 100%) of the product 14 as a colorless oil. MS (FAB for M+1): m/e 258.

Step 11:

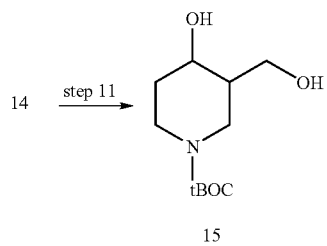

Compound 14 (10.0 g, 0.0389 mol) and NaBH$_4$ (3.69 g, 0.0973 mol) were dissolved in dry THF (150 ml) and refluxed under nitrogen. MeOH (30 ml) was added dropwise via syringe pump at a rate of 8.4 ml/hour. After MeOH addition was complete, the reaction mixture was refluxed for 3 h, then cooled to 23° and concentrated. Water (150 ml) was added and the mixture extracted with CH$_2$Cl$_2$. The combined organic extracts were dried (MgSO$_4$), filtered, and concentrated. Purification by silica gel chromatography (eluant: 5% MeOH—CH$_2$Cl$_2$ to 10% MeOH—CH$_2$Cl$_2$) gave 8.27 g (0.0358 mol, 92%) of the product 15 as a colorless oil. MS (ES for M+1): m/e 232.

Step 3:

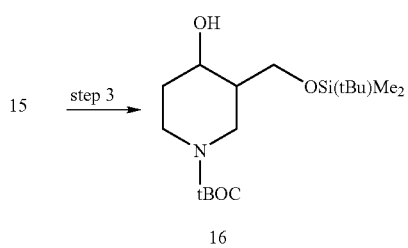

Using the same procedure as in Example 1, Step 3, compound 16 was prepared. MS (ES for M+1): m/e 346.

Step 12:

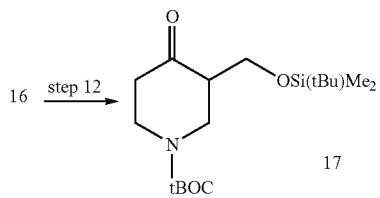

Oxalyl chloride (5.71 g, 0.0450 mol) was dissolved in dry CH₂Cl₂ (125 ml) and cooled to −78° C. under nitrogen. DMSO (7.03 g, 6.4 ml, 0.0900 mol) dissolved in dry CH₂Cl₂ (25 ml) was added dropwise via addition funnel. The mixture was stirred at −78° C. for 15 mins, then compound 16 (12.40 g, 0.0360 mol) dissolved in dry CH₂Cl₂ (50 ml) was added dropwise via addition funnel. The mixture was stirred at −78° C. for 60 mins, then Et₃N (10.92 g, 15.0 ml, 0.108 mol) was added and the mixture stirred again at −78° C. for 20 mins, then at 0° C. for 30 mins. Water (200 ml) was added, the layers were separated, and the aqueous solution was extracted with CH₂Cl₂. The combined organic extracts were dried (MgSO₄), filtered, and concentrated. Purification by silica gel chromatography (eluant: 1:4 EtOAc:hexane) gave 11.90 g (0.0347 mol, 97%) of the product 17 as a light yellow oil. MS (FAB for M+1): m/e 344.

Step 1:

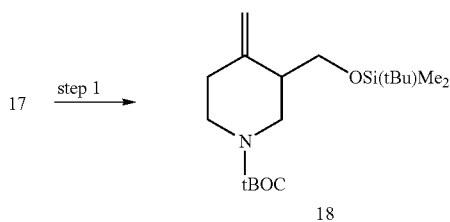

Using the same procedure as for Example 1, Step 1, compound 18 was prepared. MS (ES for M+1): m/e 342.

Step 4:

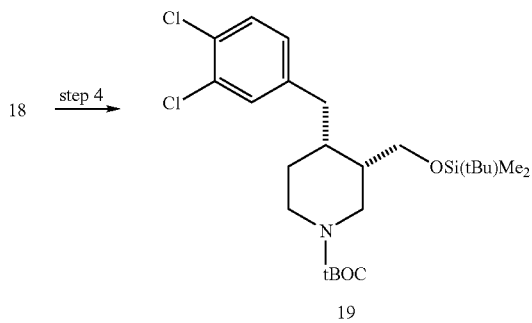

Using the same procedure as for Example 1, Step 4, compound 19 was prepared. MS (ES for M+1): m/e 488.

Step 5:

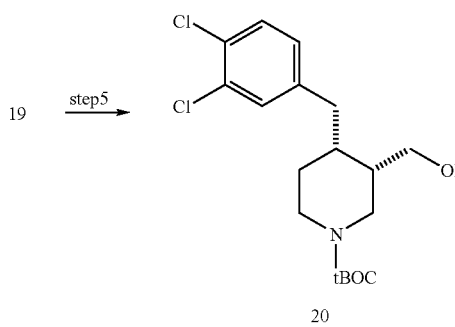

Using the same procedure as for Example 1, Step 5, compound 20 was prepared. MS (ES for M+1): m/e 374.

Step 13:

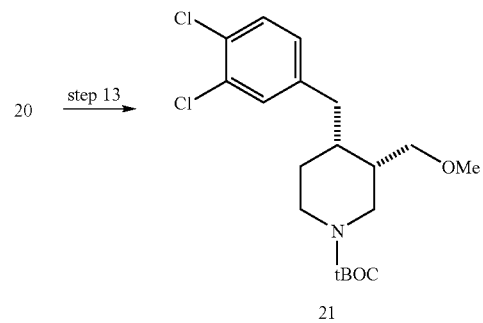

Compound 20 (0.80 g, 2.13 mmol) was dissolved in dry DMF (25 ml) and cooled to 0° C. NaH (0.13 g of 60 weight % in oil, 3.20 mmol) was added and the mixture was stirred at 0° C. for 15 mins, then at 23° C. for 30 mins. CH₃I (0.60 g, 0.27 ml, 4.26 mmol) was added, the mixture was stirred at 23° C. for 16 h, then concentrated. Water (40 ml) was added and the mixture was extracted with CH₂Cl₂. The combined organic extracts were dried (MgSO₄), filtered, and concentrated. Purification by silica gel chromatography (eluant: 20% EtOAc-hexane to 30% EtOAc-hexane) gave 0.82 g (2.13 mmol, 100%) of the product 21 as a colorless oil. MS (FAB for M+1): m/e 388.

Step 12:

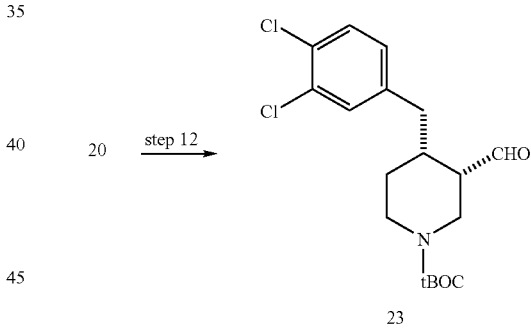

Using the same procedure as for Step 12, above, compound 23 was prepared. MS (ES for M+1): m/e 372.

Step 14:

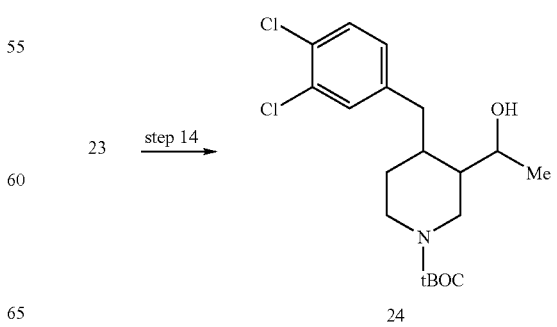

Compound 23 (0.95 g, 2.56 mmol) was dissolved in dry THF (20 ml) and CH₃MgBr (1.30 ml, 3.84 mmol, 2.95 M in THF) was added. The mixture was refluxed for 3 h, then cooled to 0° C. and concentrated. Saturated NH₄Cl (50 ml) was added and the mixture was extracted with CH₂Cl₂. The combined organic extracts were dried (MgSO₄), filtered, and concentrated. Purification by silica gel chromatography (eluant: 1:1 EtOAc:hexane) gave 0.39 g (1.01 mmol, 40%) of the product 24 as a white foam. MS (FAB for M+1): m/e 388.

Step 7:

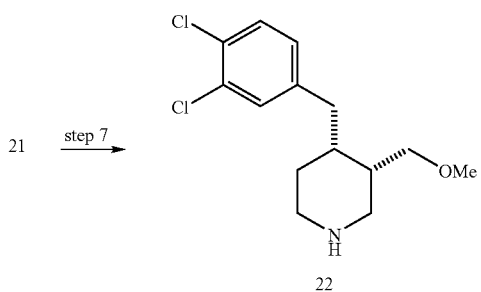

Using the same procedure as for Example 1, Step 7, compound 22 was prepared. MS (ES for M+1): m/e 288.

Following a similar procedure, additional intermediates were prepared:

| Compound | MS (FAB or ES) |
|---|---|
| (3,4-dichlorobenzyl piperidine with CH₂OH) | 274 |
| (3,4-dichlorobenzyl piperidine with CH(OH)Me) | 288 |

Step 8:

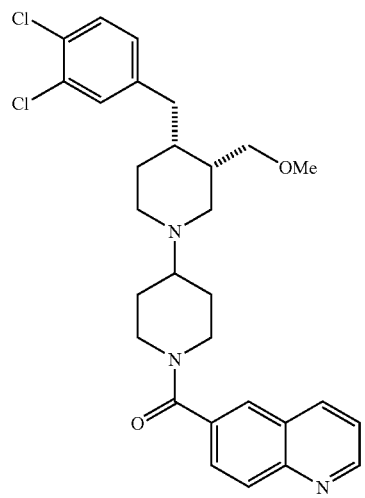

Ex. 2-A

Using the same procedure as for Example 1, Step 8, the compound of Example 2-A was prepared. MS (ES for M+1): m/e 526.

Step 15:

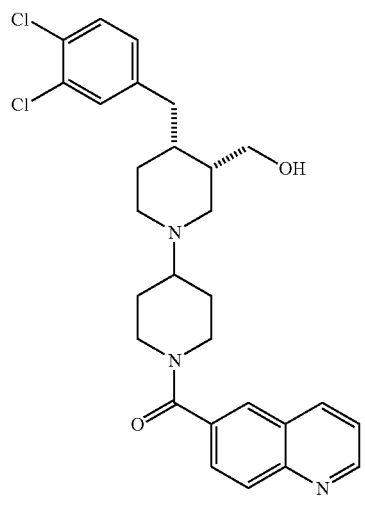

Ex. 2-B

Compound 22 (0.36 g, 1.42 mmol), N-(6-quinolinylcarboxyl)-4-piperidone (0.39 g, 1.42 mmol), and titanium isopropoxide (0.51 g, 1.78 mmol) were combined in dry CH₂Cl₂ (2 ml) and stirred at 23° C. under nitrogen for 8 h. NaBH₃CN (0.11 g, 1.78 mmol) and EtOH (5 ml) were added and stirred at 23° C. for 16 h. CH₂Cl₂ (20 ml) and 1.0 N NaOH (20 ml) were added and the mixture was filtered through celite. The celite was washed with CH₂Cl₂ and water, the filtrate layers were separated, and the aqueous solution was extracted with CH₂Cl₂. The combined organic extracts were dried (MgSO₄), filtered, and concentrated. Purification by silica gel chromatography (eluant: 5% MeOH—CH₂Cl₂ to 10% MeOH—

CH$_2$Cl$_2$) gave 0.46 g (0.898 mmol, 63%) of Example 2-B as a white foam. MS (FAB for M+1): m/e 512.

The following compounds were prepared according to a similar procedure:

| Ex. | Compound | MS (CI, FAB or ES) |
|---|---|---|
| 2-C | (structure) | 512 enantiomers A and B |
| 2-D | (structure) | 512 enantiomers A and B |
| 2-E | (structure) | 512 enantiomers A and B |
| 2-F | (structure) | 582 |
| 2-G | (structure) | 548 enantiomers A and B |
| 2-H | (structure) | 548 enantiomers A and B |

-continued

| Ex. | Compound | MS (CI, FAB or ES) |
|---|---|---|
| 2-I | [3,4-dichlorobenzyl-piperidine-CH2OH, N-linked to piperidine, N-carbonyl-(2-hydroxyquinolin-4-yl)] | 528 enantiomers A and B |
| 2-J | [3,4-dichlorobenzyl-piperidine-CH2OH, N-linked to piperidine, N-carbonyl-(2-trifluoromethylquinolin-6-yl)] | 580 |
| 2-K | [3,4-dichlorobenzyl-piperidine-CH2OH, N-linked to piperidine, N-carbonyl-(8-methoxy-2-trifluoromethylquinolin-5-yl)] | 610 |
| 2-L | [3,4-dichlorobenzyl-piperidine-CH2OH, N-linked to piperidine, N-carbonyl-(2-propylquinolin-4-yl)] | 554 |
| 2-M | [3,4-dichlorobenzyl-piperidine-CH2OH, N-linked to piperidine, N-carbonyl-(1,2,3,4-tetrahydroacridin-9-yl)] | 566 |

-continued
| Ex. | Compound | MS (CI, FAB or ES) |
|---|---|---|
| 2-N | 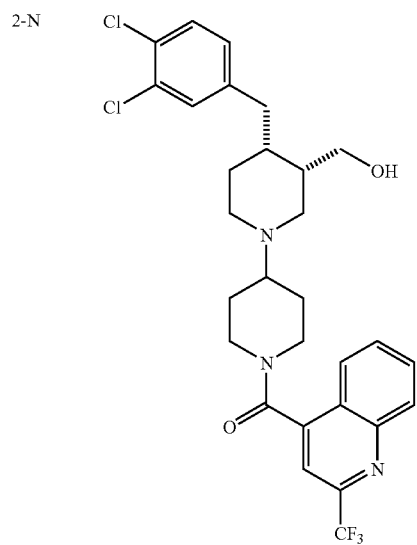 | 580 |
| 2-O | 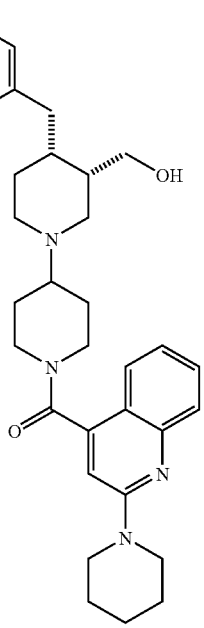 | 595 |
-continued
| Ex. | Compound | MS (CI, FAB or ES) |
|---|---|---|
| 2-P | 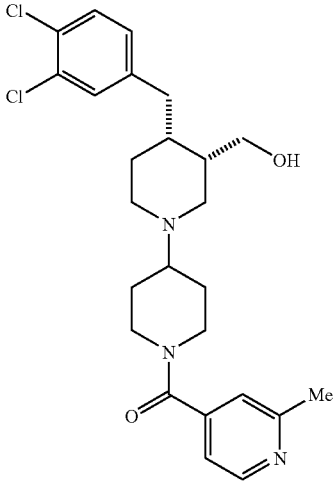 | 476 |
| 2-Q | 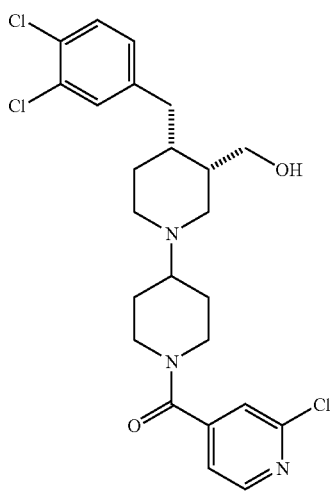 | 498 |
| 2-R | 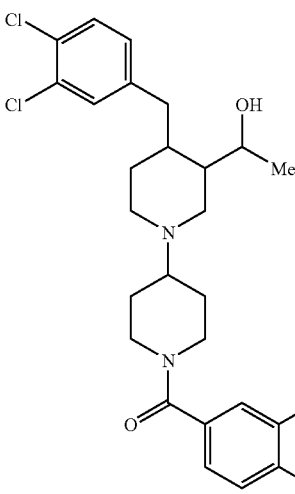 | 526 |
(enant. B)

-continued
| Ex. | Compound | MS (CI, FAB or ES) |
|---|---|---|
| 2-S | 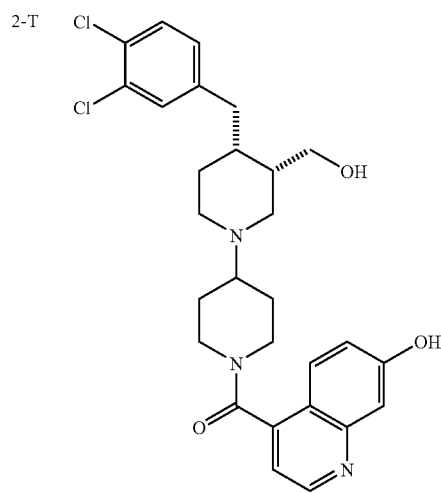 | 528 enantiomers A and B |
| 2-T | 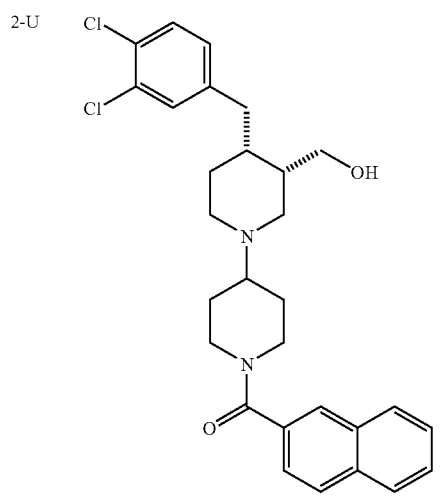 | 528 |
| 2-U | | 511 |
-continued
| Ex. | Compound | MS (CI, FAB or ES) |
|---|---|---|
| 2-V | 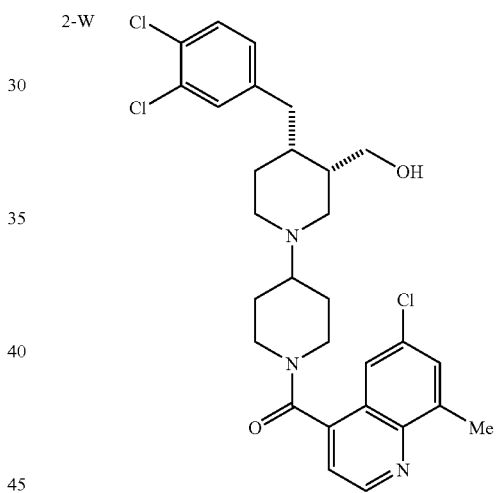 | 542 |
| 2-W | 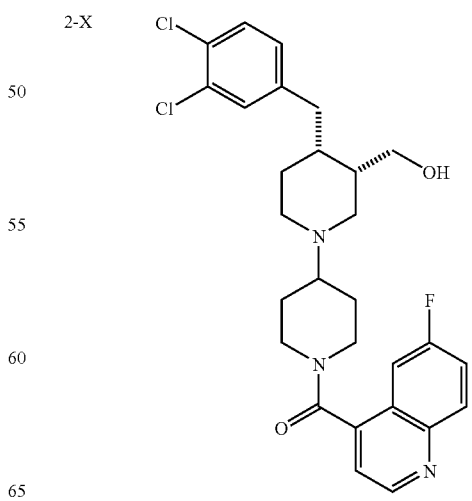 | 560 |
| 2-X | | 530 |

-continued

| Ex. | Compound | MS (CI, FAB or ES) |
|---|---|---|
| 2-Y | 3,4-dichlorobenzyl-piperidine-CH2OH linked to N-piperidinyl-C(O)-(3-methylquinolin-4-yl) | 526 |
| 2-Z | 3,4-dichlorobenzyl-piperidine-CH2OH linked to N-piperidinyl-C(O)-(6-fluoro-3-methylquinolin-4-yl) | 544 |
| 2-AA | 3,4-dichlorobenzyl-piperidine-CH2OH linked to N-piperidinyl-C(O)-(6-OCF3-quinolin-4-yl) | 596 |

-continued

| Ex. | Compound | MS (CI, FAB or ES) |
|---|---|---|
| 2-BB | 3,4-dichlorobenzyl-piperidine-CH2OH linked to N-piperidinyl-C(O)-(3-ethylquinolin-4-yl) | 540 |
| 2-CC | 3,4-dichlorobenzyl-piperidine-CH2OH linked to N-piperidinyl-C(O)-(6-CF3-pyridin-3-yl) | 530 |
| 2-DD | 3,4-dichlorobenzyl-piperidine-CH2OH linked to N-piperidinyl-C(O)-(4-CF3-naphthalen-1-yl) | 529 |

-continued

| Ex. | Compound | MS (CI, FAB or ES) |
|---|---|---|
| 2-EE | (3,4-dichlorobenzyl)-piperidine-CH2OH linked to N-piperidine-C(O)-(8-methoxyquinolin-5-yl) | 542 diastereomer and enantiomers A and B |
| 2-FF | (3,4-dichlorobenzyl)-piperidine-CH2OH linked to N-piperidine-C(O)-(5-chloro-4-methylquinolin-8-yl) | 560 |
| 2-GG | (3,4-dichlorobenzyl)-piperidine-CH2OH linked to N-piperidine-C(O)-(6-fluoro-2-hydroxyquinolin-4-yl) | 546 |
| 2-HH | (3,4-dichlorobenzyl)-piperidine-CH2OH linked to N-piperidine-C(O)-(8-chloroquinolin-5-yl) | 546 |
| 2-II | (3,4-dichlorobenzyl)-piperidine-CH2OH linked to N-piperidine-C(O)-(8-chloroquinolin-5-yl) | 528 |
| 2-JJ | (3,4-dichlorobenzyl)-piperidine-CH2OH linked to N-piperidine-C(O)-(8-methoxy-2-trifluoromethylquinolin-5-yl) | 610 diastereomer and enantiomers A and B |

-continued
| Ex. | Compound | MS (CI, FAB or ES) |
|---|---|---|
| 2-KK | 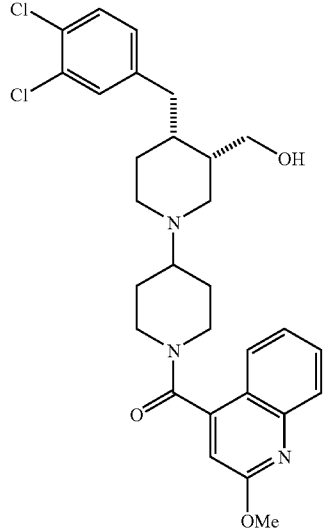 | 542 |
| 2-LL | 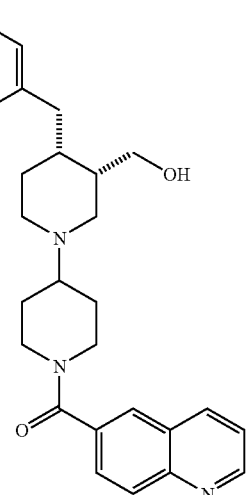 | 494 |
| 2-MM | 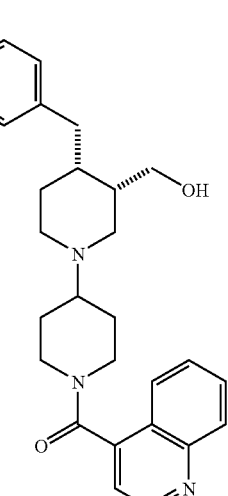 | 494 |
-continued
| Ex. | Compound | MS (CI, FAB or ES) |
|---|---|---|
| 2-NN | 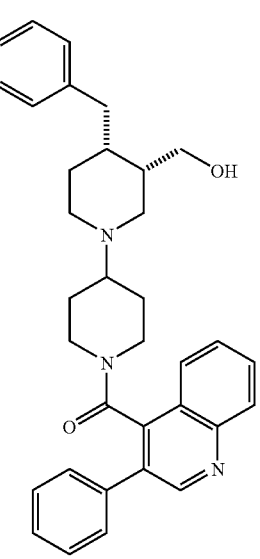 | 588 |
| 2-OO | 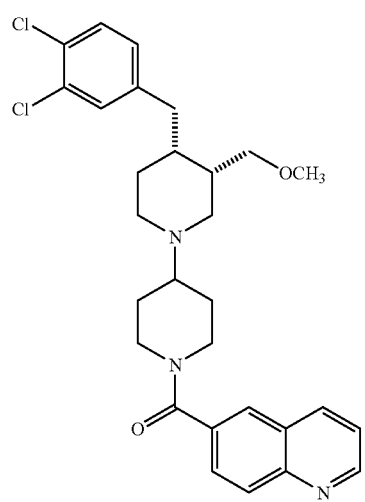 | 526 cis enantiomers A and B |

Example 3
General Procedure
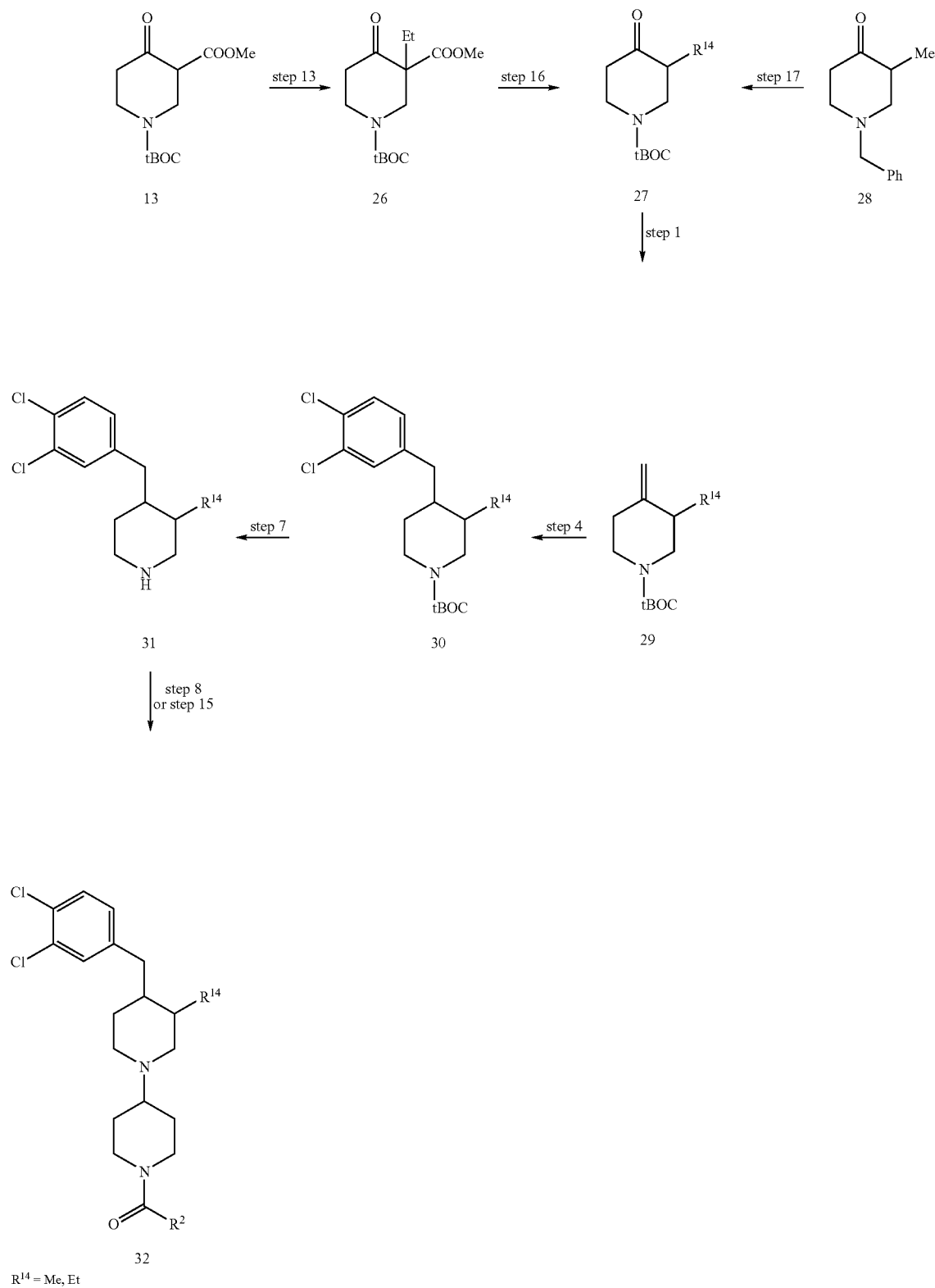
$R^{14}$ = Me, Et

Step 13:

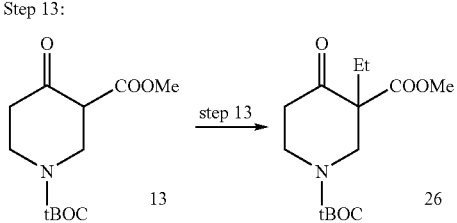

Using the same procedure as for Example 2, Step 13, compound 26 was prepared. MS (FAB for M+1): m/e 286.

Step 16:

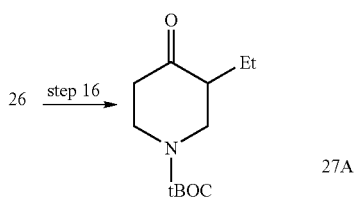

Compound 26 (2.90 g, 10.2 mmol) was suspended in 6 N HCl (85 ml) and refluxed for 16 h. The product was concentrated and azeotroped three times with isopropanol to give a yellow solid. The solid was dissolved in 1:1 $CH_2Cl_2$:MeOH (50 ml) and $Et_3N$ (3.08 g, 4.3 ml, 30.5 mmol) and di-t-butyl dicarbonate (3.32 g, 15.2 mmol) were added. The mixture was stirred at 23° C. for 16 h, then concentrated. 0.5 N NaOH (50 ml) was added and the mixture extracted with $CH_2Cl_2$. The combined organic extracts were dried ($MgSO_4$), filtered, and concentrated. Purification by silica gel chromatography (eluant: 10% EtOAc-hexane) gave 1.92 g (8.46 mmol, 83%) of the product 27A as a colorless oil. MS (ES for M+1): m/e 228.

Step 17:

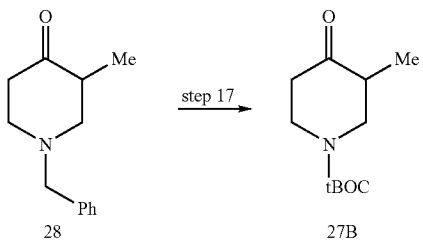

Compound 28 (15.0 g, 0.0738 mol) and di-t-butyl dicarbonate (17.7 g, 0.0812 mol) were dissolved in EtOAc (400 ml). Palladium hydroxide catalyst (4 g) was added and the mixture was shaken on a Paar shaker under 40 psi of hydrogen pressure for 24 h. The resultant mixture was filtered through celite and the celite was washed with EtOAc. The filtrate was concentrated to give 15.73 g (0.0738 mol, 100%) of the product 27B as a colorless oil. MS (ES for M-tBOC+1): m/e 114.

Step 1:

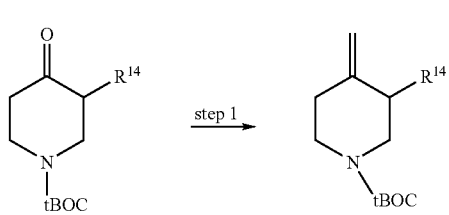

$R^{14}$ = Me, Et

Using the same procedure as for Example 1, Step 1, compounds 29a and 29b were prepared:

| Compound | | MS (FAB or ES) |
|---|---|---|
| 29a | 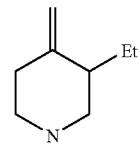 | 226 |
| 29b | 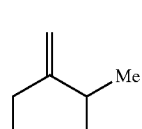 | 220/320<br>dimer-2-tBOC(100) = 320<br>dimer-2-[2X tBOC] = 220 |

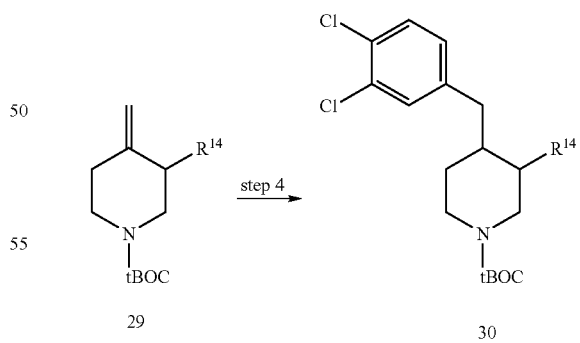

$R^{14}$ = Et, Me

Using the same procedure as for Example 1, Step 4, compounds 30a and 30b were prepared. The cis and trans isomers of compound 30b ($R^{14}$=Me) were separated by silica gel chromatography (eluant 3% EtOAc-hexane to 10% EtOAc-hexane) to 90% purity.

| Compound | MS FAB or ES |
|---|---|
| 30a (3,4-dichlorobenzyl-4-yl, 3-Et, N-tBOC piperidine) | 372 |
| 30b (3,4-dichlorobenzyl-4-yl, 3-Me, N-tBOC piperidine) | 358 |

| Compound | MS (FAB or ES) |
|---|---|
| 31a (3,4-dichlorobenzyl-4-yl, 3-Et, NH piperidine) | 272 |
| 31b (3,4-dichlorobenzyl-4-yl, 3-Me, NH piperidine) | 258 |

Step 7:

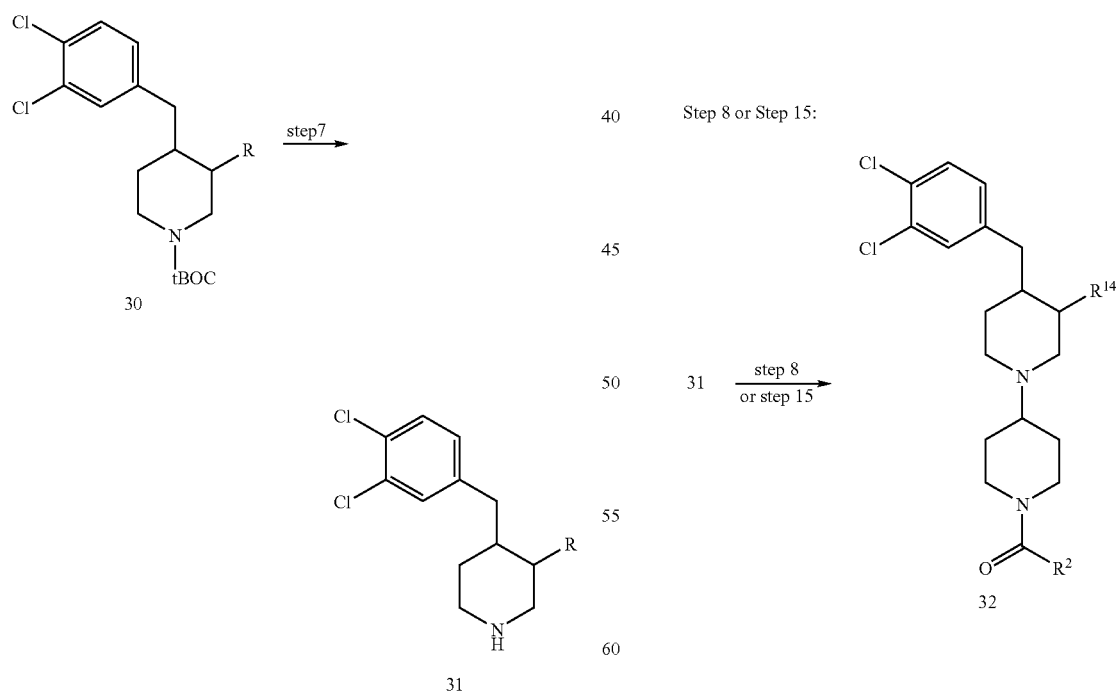

$R^{14}$ = Et, Me

Using the same procedure as for Example 1, Step 7, compounds 31a and 31b were prepared.

Using the same procedure as for Example 1, Step 8, or Example 2, Step 15, the following compounds were prepared:

| Ex. | Compound | MS (FAB or ES) |
|---|---|---|
| 3-A | 3,4-dichlorobenzyl-(3-methylpiperidin-4-yl)-[1-(quinoline-6-carbonyl)piperidin-4-yl] | 496 diastereomer and cis enantiomers A and B |
| 3-B | 3,4-dichlorobenzyl-(3-ethylpiperidin-4-yl)-[1-(quinoline-6-carbonyl)piperidin-4-yl] | 510 |
| 3-C | 3,4-dichlorobenzyl-(3-methylpiperidin-4-yl)-[1-(quinoline-4-carbonyl)piperidin-4-yl] | 496 diastereomer and cis enantiomers A and B |
| 3-D | 3,4-dichlorobenzyl-(3-methylpiperidin-4-yl)-[1-(quinoline-3-carbonyl)piperidin-4-yl] | 496 |
| 3-E | 3,4-dichlorobenzyl-(3-methylpiperidin-4-yl)-[1-(quinoline-8-carbonyl)piperidin-4-yl] | 496 cis enantiomers A and B |
| 3-F | 3,4-dichlorobenzyl-(3-methylpiperidin-4-yl)-[1-(3,7-dichloroquinoline-8-carbonyl)piperidin-4-yl] | 566 cis enantiomers A and B |

-continued
| Ex. | Compound | MS (FAB or ES) |
|---|---|---|
| 3-G | | 582 cis enantiomers A and B |
| 3-H | | 497 |
| 3-I | | 497 cis/trans mixture and cis enantiomer |
Example 4-A
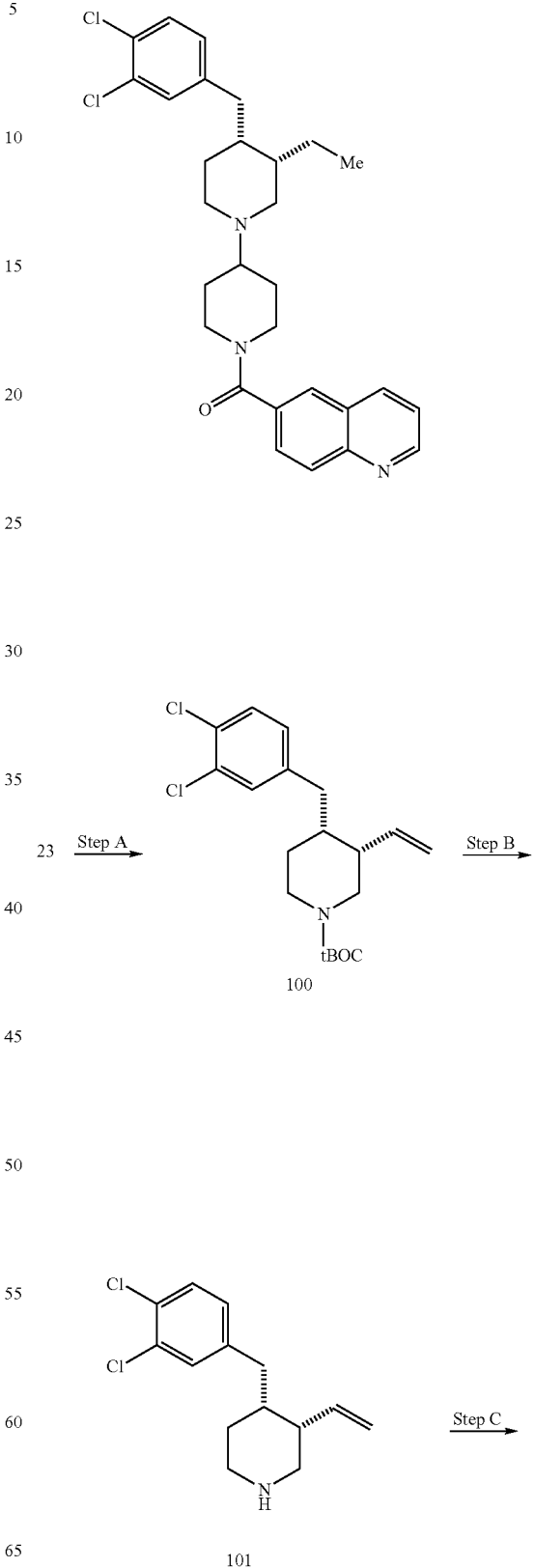

-continued

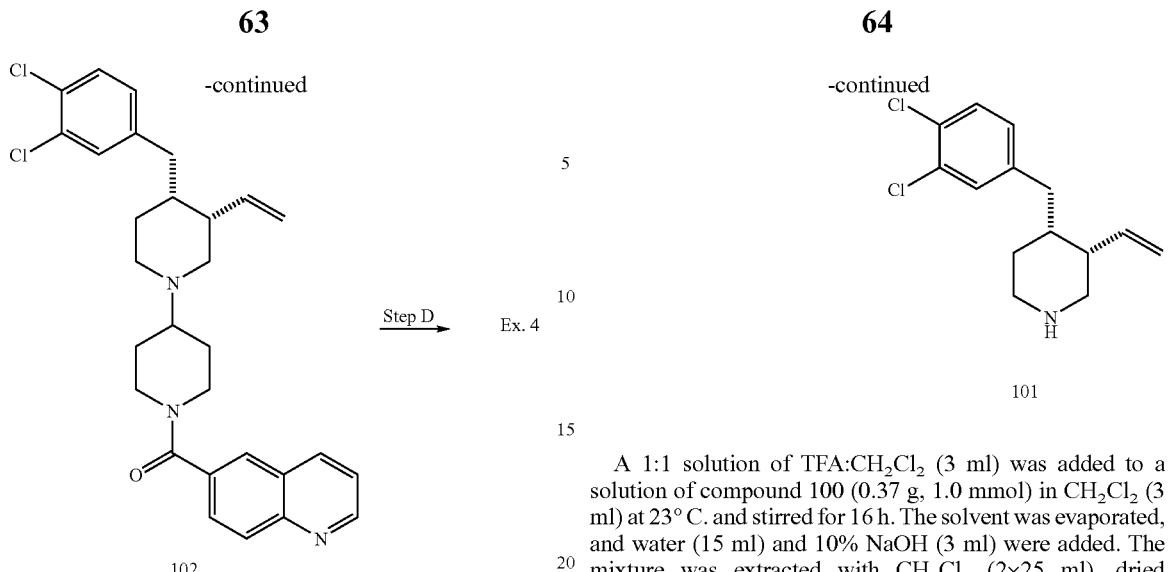

Step A:

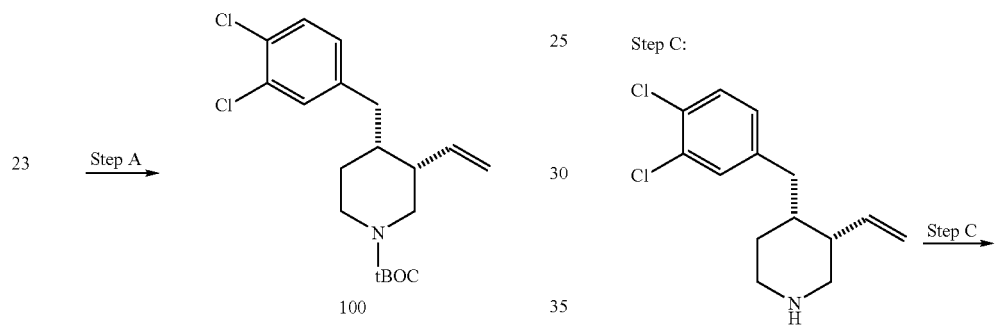

A solution of 0.5M potassium bis(trimethylsilyl)amide in toluene (2.68 ml, 1.34 mmol), was added to a suspension of methyl(triphenyl)phosphonium bromide (0.70 g, 1.95 mmol) in Et$_2$O (anhydrous, 10 ml) at −78° C. The mixture was stirred for 1 h at 10-30° C., then cooled to −40° C., and a solution of the aldehyde 23 (0.50 g, 1.34 mmol) in Et$_2$O (anhydrous, 5 ml) was added dropwise. The reaction mixture was stirred at −30° C. for 30 min, then quenched with acetone (1 ml). Et$_2$O (100 ml) and water (50 ml) were added, and the organic layer was separated, then dried (MgSO$_4$), filtered, and concentrated. Purification by silica gel chromatography (eluant: 10% v/v acetone/hexane) gave 0.37 g (1.00 mmol, 75%) of the "cis" isomer product 100 as a colorless oil. MS (FAB for M+1): m/e 370.

Step B:

-continued

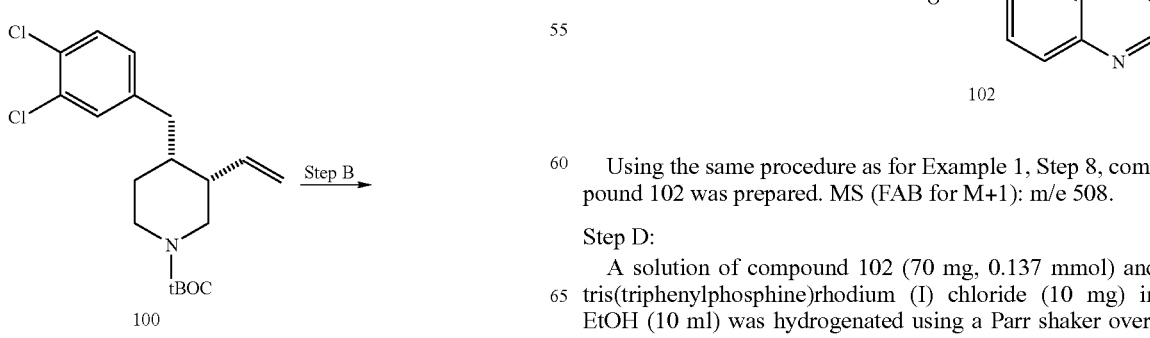

A 1:1 solution of TFA:CH$_2$Cl$_2$ (3 ml) was added to a solution of compound 100 (0.37 g, 1.0 mmol) in CH$_2$Cl$_2$ (3 ml) at 23° C. and stirred for 16 h. The solvent was evaporated, and water (15 ml) and 10% NaOH (3 ml) were added. The mixture was extracted with CH$_2$Cl$_2$ (2×25 ml), dried (MgSO$_4$), filtered and concentrated to give 0.24 g (0.89 mmol, 89%) of the product 101. MS (FAB for M+1): m/e 270.

Step C:

Using the same procedure as for Example 1, Step 8, compound 102 was prepared. MS (FAB for M+1): m/e 508.

Step D:
A solution of compound 102 (70 mg, 0.137 mmol) and tris(triphenylphosphine)rhodium (I) chloride (10 mg) in EtOH (10 ml) was hydrogenated using a Parr shaker overnight. The reaction was filtered through celite and the celite was washed with EtOH. The filtrate was concentrated. Purification by silica gel chromatography (eluant: 10% v/v MeOH with NH$_3$/EtOAc) gave 36 mg (0.076 mmol, 55%) of the title compound (Ex. 4-A) as a white foam. MS (FAB for M+1)=510.
Example 4-B
General Procedure
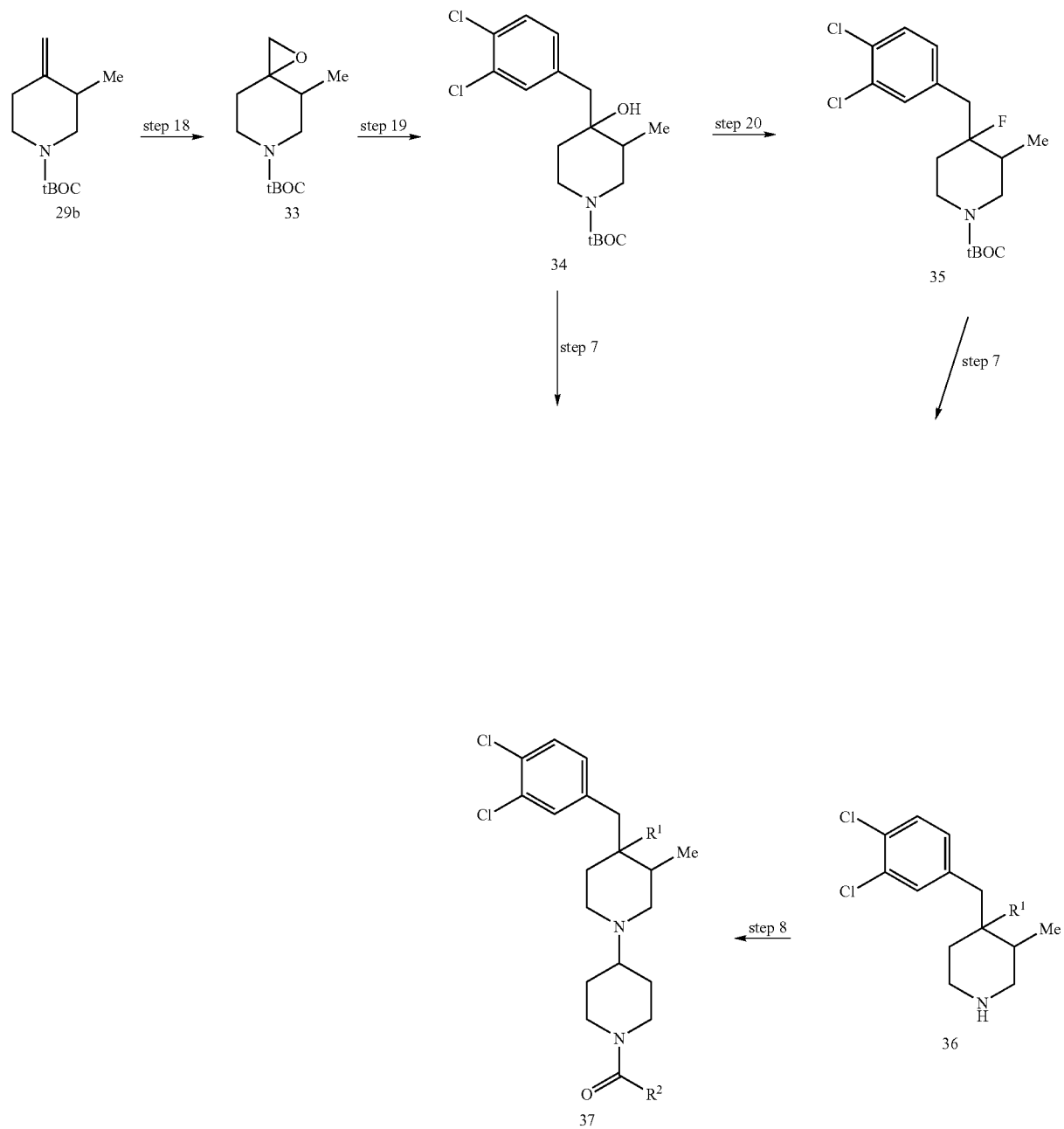

Step 18:

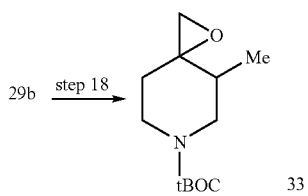 33

Compound 29b (7.92 g, 0.0375 mol) was dissolved in CH$_2$Cl$_2$ (250 ml) and cooled to 0° C. NaHCO$_3$ (4.73 g, 0.0563 mol) and MCPBA (12.95 g of 75% purity, 0.0563 mol) were added and the mixture was stirred at 0° C. for 20 mins, then at 23° C. for 16 h. CH$_2$Cl$_2$ (500 ml) was added and the mixture was washed with 0.5 N NaOH (300 ml) and saturated sodium bisulfite (300 ml). The combined organic extracts were dried (MgSO$_4$), filtered, and concentrated. Purification by silica gel chromatography (eluant: 1:3 EtOAc:hexane) gave 6.83 g (0.030 mol, 80%) of the product 33 as a colorless oil. MS (ES for M+1): m/e 228.

Step 19:

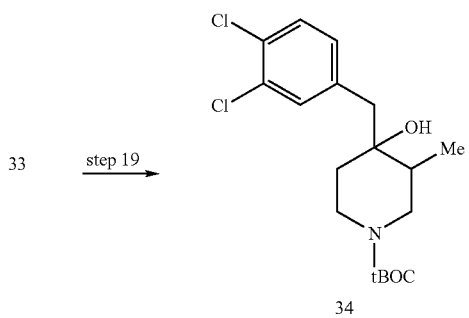

Magnesium (1.46 g, 0.060 mol) was suspended in dry THF (10 ml) and 1-bromo-3,4-dichlorobenzene (13.56 g, 0.060 mol) was added via addition funnel. A crystal of iodine and few drops of 1,2-dibromoethane were added to start the grignard reaction. Dry THF (10 ml) was added and the mixture was refluxed for 45 mins. Dry THF (80 ml) was added and cooled to −30° C. Copper iodide (5.71 g, 0.030 mol) and dimethylsulfide (10 ml) were added and the mixture was stirred at −30° C. for 2 h. Compound 33 (6.82 g, 0.030 mol) dissolved in dry THF (25 ml) was added dropwise via addition funnel and the mixture was stirred at −15° C. for 16 h, then at 23° C. for 24 h. Saturated NH$_4$Cl (200 ml) was added and the mixture extracted with EtOAc. The combined organic extracts were dried (MgSO$_4$), filtered, and concentrated. Purification by silica gel chromatography (eluant: 1:2 Et$_2$O-hexane, then 1:1 Et$_2$O-hexane, then 1:2 EtOAc:hexane) gave 3.29 g (0.0088 mol, 29%) of the product 34 as a yellow foam. MS (ES for M+1): m/e 374.

Step 60:

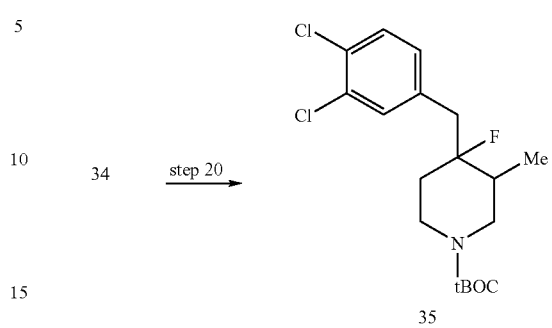

Compound 34 (2.38 g, 6.36 mmol) was dissolved in dry CH$_2$Cl$_2$ (40 ml) and cooled to −78° C. Diethylaminosulfur trifluoride (1.28 g, 7.95 mmol) was added and the mixture was stirred at −78° C. for 15 mins, then warmed slowly to 0° C. 1 N NaOH (75 ml) was added and the mixture extracted with CH$_2$Cl$_2$. The combined organic extracts were dried (MgSO$_4$), filtered, and concentrated to give a yellow oil. The oil was dissolved in CH$_2$Cl$_2$ (40 ml) and NaHCO$_3$ (0.53 g, 6.36 mmol) and MCPBA (1.46 g of 75% purity, 6.36 mmol) were added to epoxidize the alkene by-product for purification. The mixture was stirred at 23° C. for 16 h. 0.5 N NaOH (50 ml) was added and the mixture extracted with CH$_2$Cl$_2$. The combined organic extracts were dried (MgSO$_4$), filtered, and concentrated. Purification by silica gel chromatography (eluant: 10% EtOAc-hexane to 25% EtOAc-hexane) gave 1.20 g (3.19 mmol, 50%) of the product 35 as a colorless oil. MS (ES for M-tBu+1): m/e 319.

Step 7:

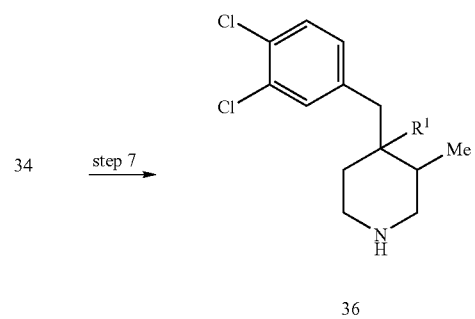

Using the same procedure as for Example 1, Step 7, the following compounds were prepared.

| Compound | MS (FAB or ES) |
|---|---|
| 36a | 274 |
| 36b | 276 |
| Ex. | Compound | MS (FAB or ES) |
|---|---|---|
| 4-B | | 512 diastereomers A and B |
| 4-C | | 514 diastereomers A and B |
Step 8:
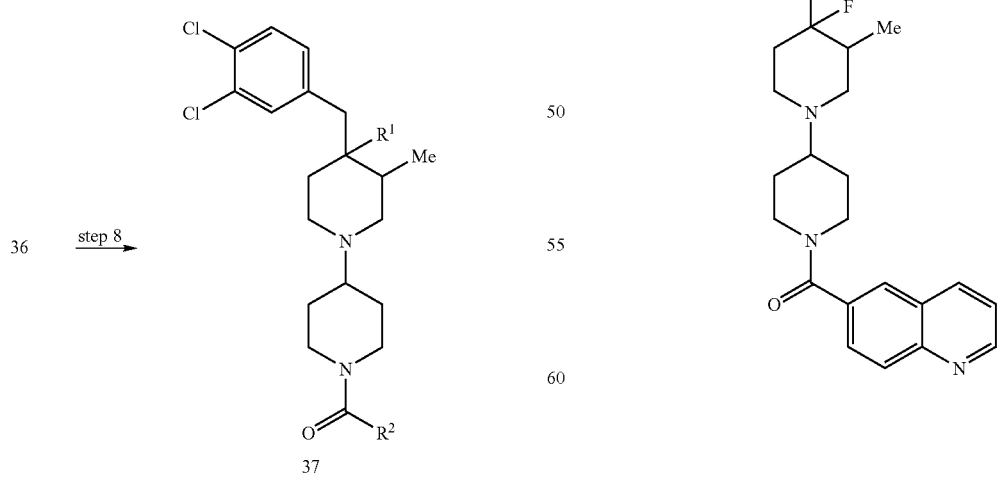
Using the same procedure as for Example 1, Step 8, the following compounds were prepared:

Example 5-A

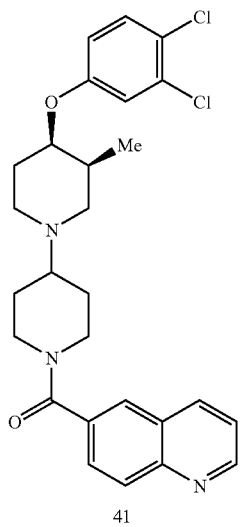
41

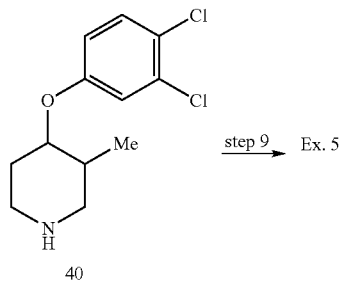
40 → step 9 → Ex. 5

Step 21:

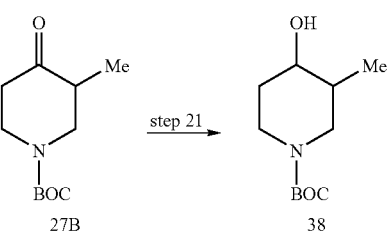
27B → step 21 → 38

NaBH$_4$ (2.18 g, 57.7 mmol) was added to a solution of compound 27B (6.10 g, 28.8 mmol) in ethanol (200 ml) at 0° C. over a period of 20 min. After 30 min, the reaction mixture was concentrated. EtOAc (150 ml) was added, and the mixture was washed with brine, dried (Na$_2$SO$_4$), filtered, and concentrated to provide 5.45 g (25.5 mmol, 88%) of compound 38 as a colorless oil. MS: m/e 160 (M-56).

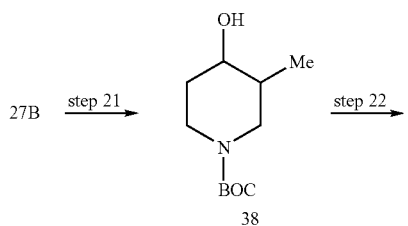
27B → step 21 → 38 → step 22

Step 22:

38 → step 22 → 
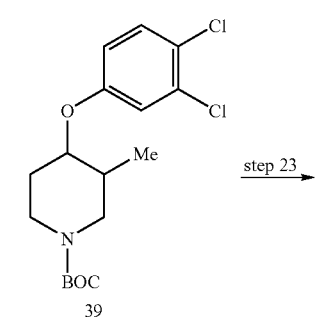
39

Diethyl azodicarboxylate (3.7 g, 21 mmol) was added to a solution of compound 38 (4.0 g, 16.7 mmol) and 3,4-dichlorophenol (2.3 g, 14.0 mmol) in THF (65 ml). The mixture was stirred at 23° C. for 3 days, then at 50° C. for 27 h. Et$_2$O was added and the mixture was washed with water, 0.4 N NaOH, water and saturated NaCl. The organic extract was dried (Na$_2$SO$_4$), filtered, and concentrated. Purification by silica gel chromatography (eluant: 1:9 EtOAc:hexane) provided 2.0 g (5.5 mmol, 40%) of compound 39 as a colorless oil. MS: m/e 360.

Step 23:

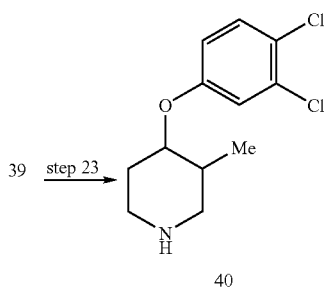

TFA (14 ml) was added slowly to a solution of compound 39 (2.0 g, 5.6 mmol) in $CH_2Cl_2$ (55 ml) and stirred at 23° C. for 30 min. The mixture was concentrated, 1N NaOH (40 ml) was added and the mixture was extracted with $CH_2Cl_2$. The combined organic extracts were dried ($Na_2SO_4$), filtered, and concentrated. Purification by silica gel preparative TLC (eluent: 1:MeOH with $NH_3$—$CH_2Cl_2$) provided 0.49 g (1.9 mmol, 34%) of the cis isomer of compound 40 as a colorless oil and 0.23 g (0.88 mmol, 16%) of the trans isomer of compound 40 as a colorless oil. MS: m/e 260.

Step 8:

Using the same procedure as for Example 1, Step 8, compound 41 (Ex. 5-A) was prepared from cis compound 40. MS: m/e 498.

Using a similar procedure, Example 5-B was prepared from trans compound 40.

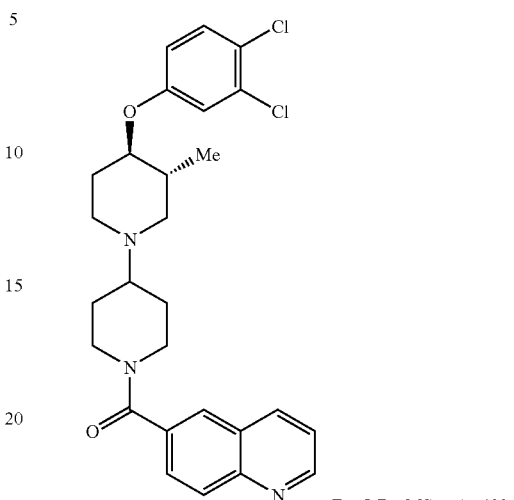

Ex. 5-B MS: m/e: 498

Example 6

Procedure for Compounds wherein $R^{14}$ is —$NH_2$, —$NHCOCF_3$, —$NHSO_2CH_3$, —$NHCOCH_3$

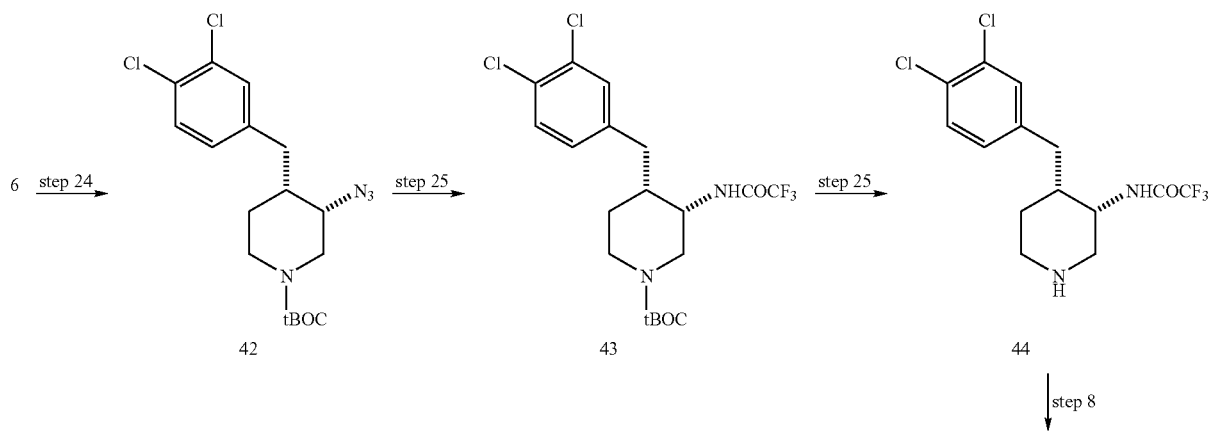

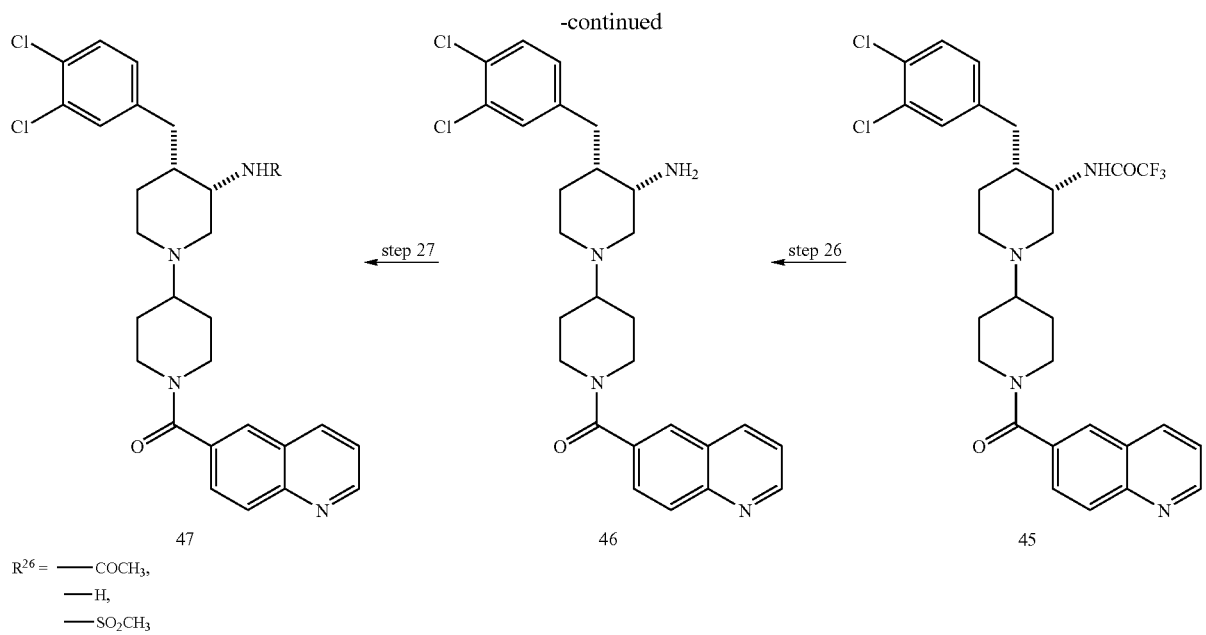

R²⁶ = —COCH₃,
—H,
—SO₂CH₃

Step 24:

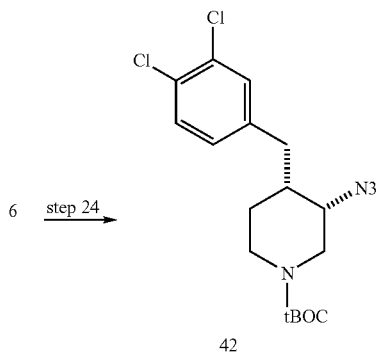

Step 25:

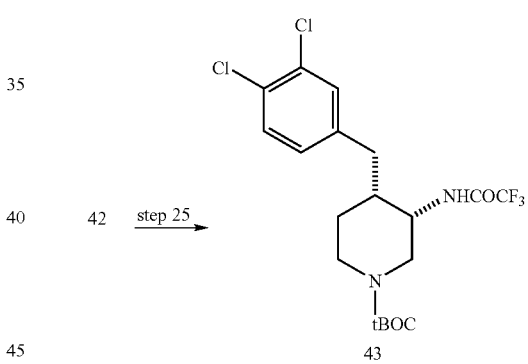

Compound 6 (1.02 g, 2.84 mmol) was dissolved in dry CH₂Cl₂ (8 ml) and cooled to 0° C. Et₃N (0.43 g, 0.59 ml, 4.25 mmol), then CH₃SO₂Cl (0.27 ml, 3.49 mmol) were added and the mixture was stirred at 23° C. for 2 h. EtOAc (40 ml) was added and the mixture was washed with 1 N HCl (25 ml). The aqueous layer was separated and extracted with EtOAc. The combined organic extracts were dried (MgSO₄), filtered and concentrated to give the mesylate (1.22 g, 2.77 mmol). The mesylate was dissolved in DMF (10 ml) and sodium azide (0.45 g, 6.92 mmol) was added. The mixture was heated at 65° C. for 12 days, then cooled to 23° C. Et₂O (75 ml) was added and the mixture was washed with water (5×10 ml). The aqueous layers were combined and extracted with Et₂O. The combined organic extracts were dried (MgSO₄), filtered and concentrated. Purification by silica gel chromatography (eluant: 1:8 EtOAc-hexane to 1:5 EtOAc-hexane) gave 0.61 g (1.59 mmol, 56%) of the product 42 as a light yellow oil. MS (ES for M+1): m/e 385.

Compound 42 (0.29 g, 0.76 mmol) was dissolved in THF (5 ml) and water (0.5 ml) and triphenylphosphine (0.41 g, 1.56 mmol) were added. The mixture was refluxed for 16 h, cooled to 23° C. and concentrated. Saturated NaCl was added and the mixture extracted with CH₂Cl₂. The combined organic extracts were dried (MgSO₄), filtered, and concentrated. The crude product was dissolved in dry CH₂Cl₂ (5 ml), cooled to 0° C., and Et₃N (0.26 ml, 1.87 mmol) and TFAA (0.13 ml, 0.92 mmol) were added. The mixture was stirred at 23° C. for 4 h, then was concentrated. Purification by silica gel chromatography (eluant: 1:10 EtOAc-hexane to 1:3 EtOAc-hexane) gave 0.25 g (0.55 mmol, 73%) of the product 43 as a white foam. MS (ES for M+1-tBOC): m/e 355.

Step 23:

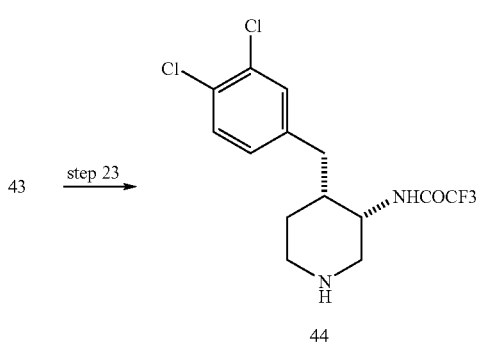

The same procedure was used as for Example 5, Step 23 to obtain compound 44. MS (ES for M+1): m/e 355.

Step 8:

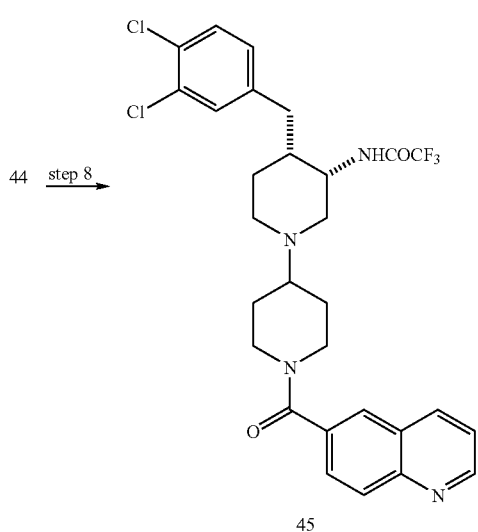

The same procedure was used as for Example 1, Step 8, to obtain compound 45. MS (ES for M+1): m/e 593.

Step 26:

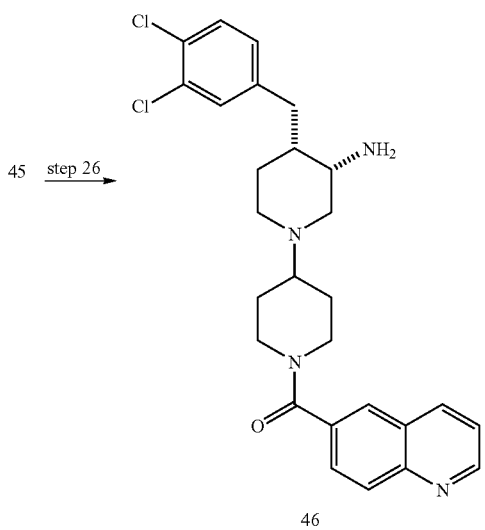

Compound 45 (0.080 g, 0.13 mmol) and $K_2CO_3$ (0.080 g, 0.58 mmol) were suspended in MeOH (1.5 ml) and water (0.5 ml), stirred at 23° C. for 3 days and concentrated. $CH_2Cl_2$ (15 ml) and water (10 ml) were added, the aqueous layer was separated and extracted with $CH_2Cl_2$ (3×15 ml). The organic extracts were combined, dried ($MgSO_4$), filtered and concentrated. Purification by silica gel chromatography (eluant: 1:10 MeOH—$CH_2Cl_2$ then 1:5 4% MeOH with $NH_3$—$CH_2Cl_2$) gave 0.052 g (0.10 mmol, 77%) of the product 46 as a white foam. MS (ES for M+1): m/e 477.

Step 23:

Ex. 6-C

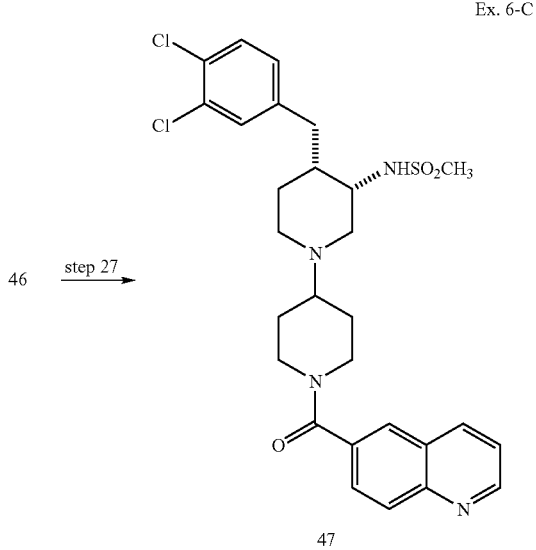

Compound 46 (0.027 g, 0.054 mmol) was dissolved in $CH_2Cl_2$ (2 ml), and $Et_3N$ (0.050 ml, 0.36 mmol) and $CH_3SO_2Cl$ (0.015 ml, 0.19 mmol) were added. The mixture was stirred at 23° C. for 16 h. 1N NaOH (10 ml) was added and the mixture extracted with $CH_2Cl_2$. The combined organic extracts were washed with brine, dried ($MgSO_4$), filtered and concentrated. Purification by silica gel preparative thin layer chromatography (eluant: 1:10 MeOH—$CH_2Cl_2$) gave 0.019 g (0.032 mmol, 60%) of compound 47 as a white foam. MS (ES for M+1): m/e 575.

Example 6-D was prepared according to the same procedure, using acetyl chloride in place of mesyl chloride:

79
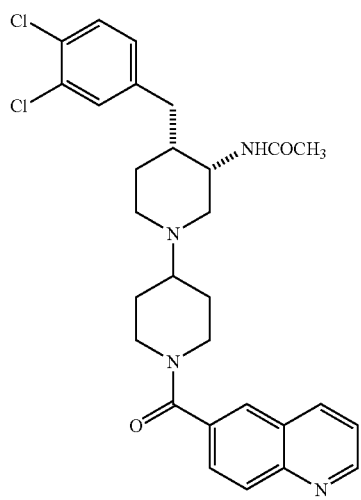
MS: m/e 539
Example 7
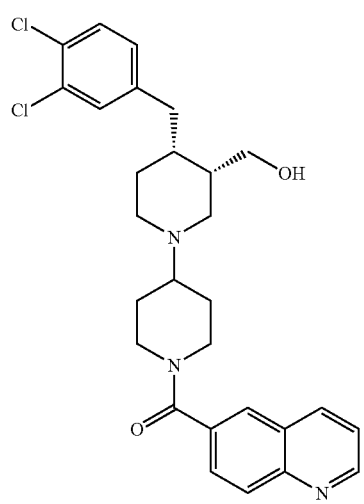
48
Ex. 6-D
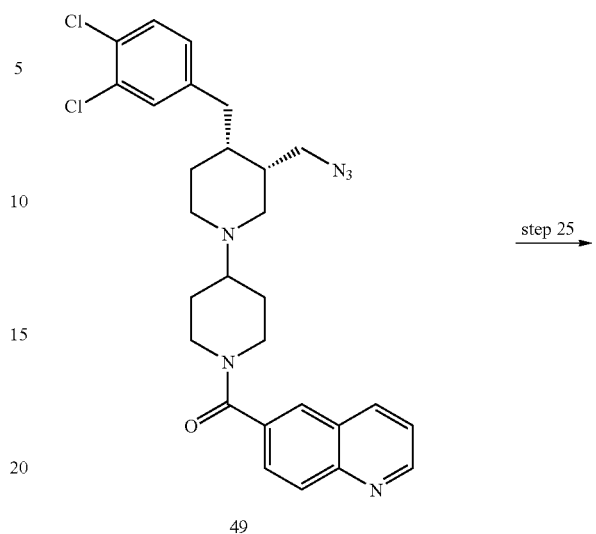
-continued
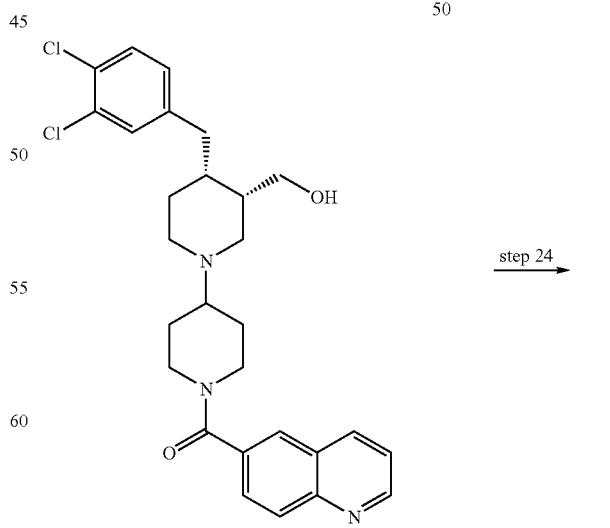
step 25 →
step 24 →
step 24 →

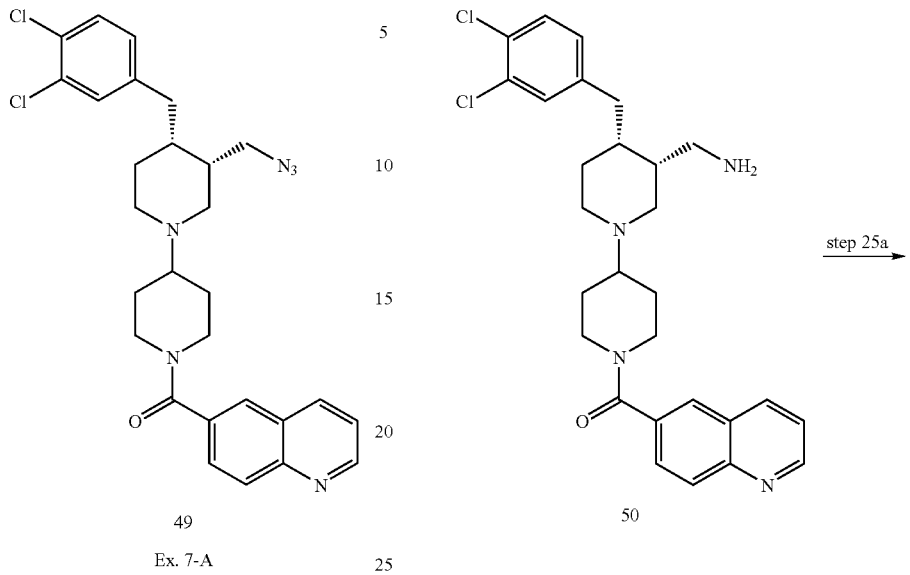

49
Ex. 7-A

Using the same procedure as for Example 6, Step 24, compound 49 was prepared. MS (ES for M+1): m/e 537.

Step 24:

Ex. 7-B

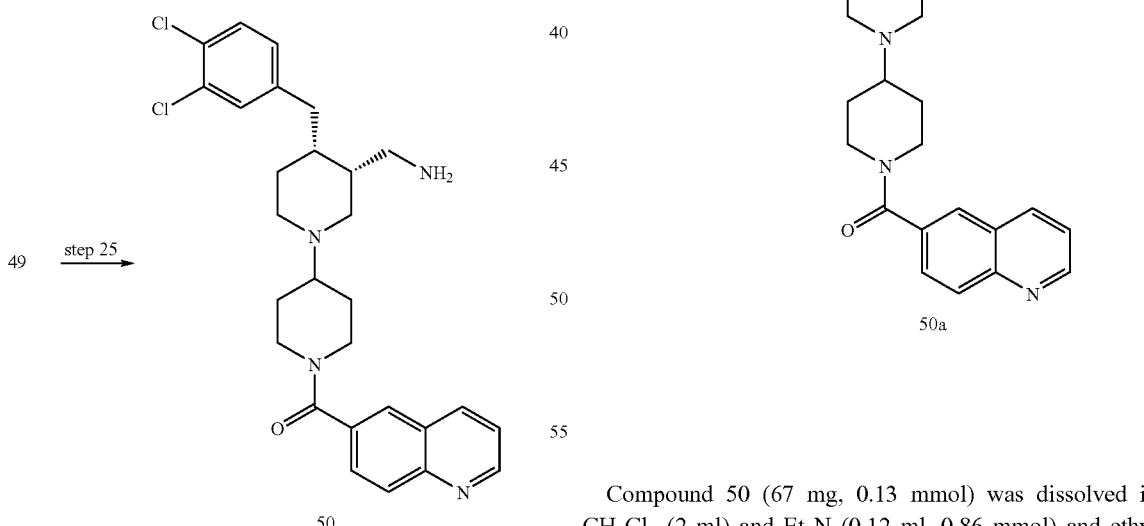

Using the same procedure as for Example 6, Step 25, but without adding the TFAA, compound 50 was prepared. MS (ES for M+1): m/e 511.

Compound 50 (67 mg, 0.13 mmol) was dissolved in $CH_2Cl_2$ (2 ml) and $Et_3N$ (0.12 ml, 0.86 mmol) and ethyl chloroformate (0.04 ml, 0.42 mmol) were added. The mixture was stirred at 23° C. for 16 h. 1 N NaOH (5 ml) was added and the mixture was extracted with $CH_2Cl_2$. The combined organic layers were dried ($MgSO_4$), filtered and concentrated. Purification by silica gel preparative TLC (eluant: 10% MeOH—$CH_2Cl_2$) gave 41 mg (51%) of the product 50a (Ex. 7-C) as a white foam. MS (for M+1): m/e 583.

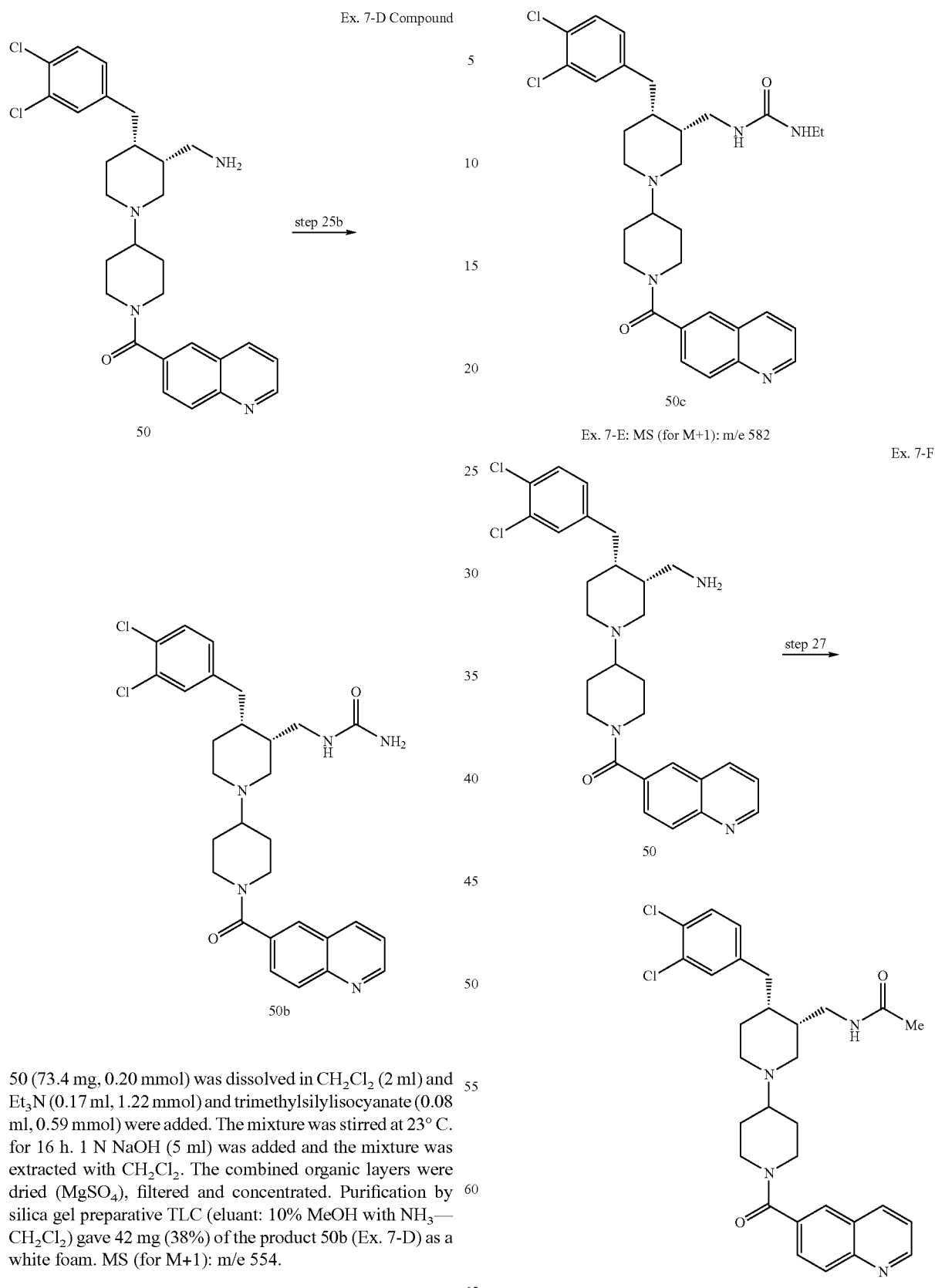

50 (73.4 mg, 0.20 mmol) was dissolved in CH$_2$Cl$_2$ (2 ml) and Et$_3$N (0.17 ml, 1.22 mmol) and trimethylsilylisocyanate (0.08 ml, 0.59 mmol) were added. The mixture was stirred at 23° C. for 16 h. 1 N NaOH (5 ml) was added and the mixture was extracted with CH$_2$Cl$_2$. The combined organic layers were dried (MgSO$_4$), filtered and concentrated. Purification by silica gel preparative TLC (eluant: 10% MeOH with NH$_3$—CH$_2$Cl$_2$) gave 42 mg (38%) of the product 50b (Ex. 7-D) as a white foam. MS (for M+1): m/e 554.

The following compound was prepared according to a similar procedure:

Using the same procedure as for Example 6, Step 27, with acetyl chloride instead of mesyl chloride, compound 50d (Ex. 7-F) was prepared. MS (for M+1): m/e 553.
Ex. 7-G
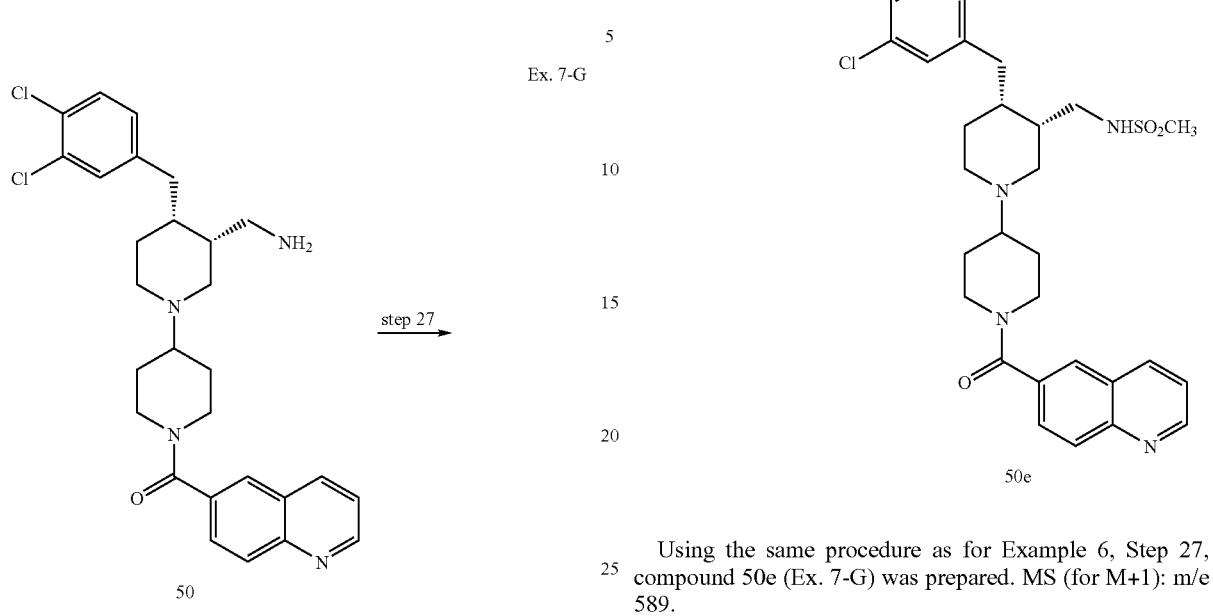
Using the same procedure as for Example 6, Step 27, compound 50e (Ex. 7-G) was prepared. MS (for M+1): m/e 589.
Example 8
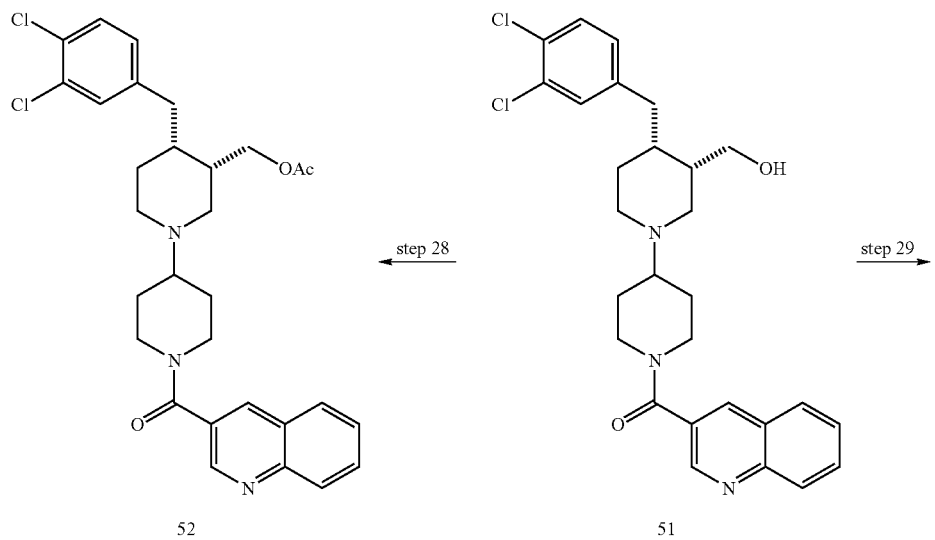

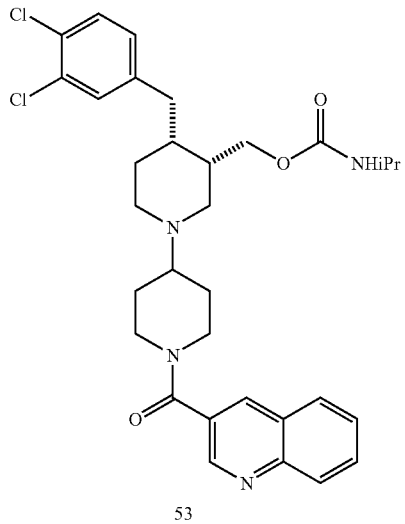

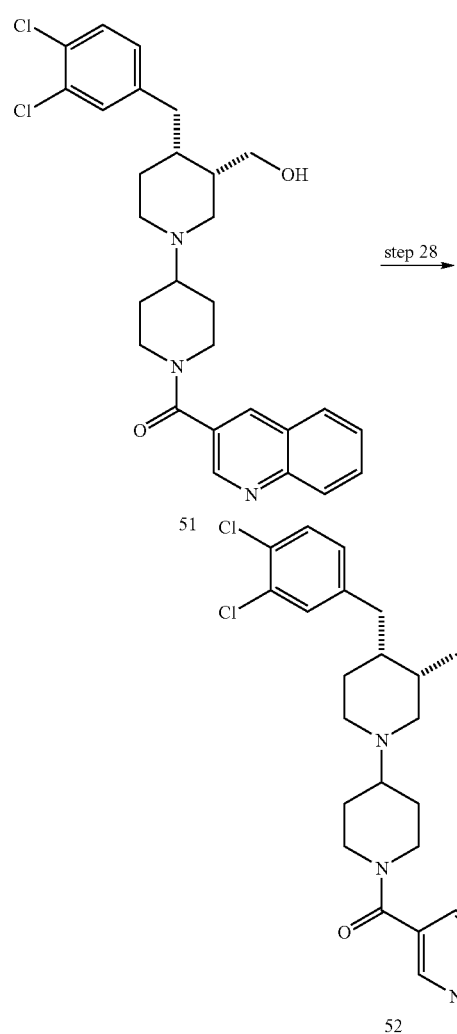

Compound 51 (0.20 g, 0.39 mmol) was dissolved in $CH_2Cl_2$ (15 ml) and $Et_3N$ (0.060 g, 0.083 ml, 0.59 mmol) and acetyl chloride (0.037 g, 0.033 ml, 0.47 mmol) were added. The mixture was stirred at 23° C. for 16 h, water (20 ml) was added and the mixture was extracted with $CH_2Cl_2$. The combined organic extracts were dried ($MgSO_4$), filtered, and concentrated. Purification by silica gel chromatography (eluant: 5% MeOH with $NH_3$—$CH_2Cl_2$) gave 0.20 g (0.36 mmol, 93%) of the product 52 as a white foam. MS (FAB for M+1): m/e 554.

-continued

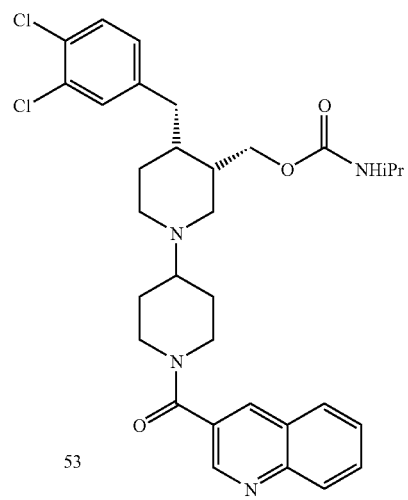

53

Compound 51 (0.20 g, 0.39 mmol) was dissolved in dry THF (10 ml) and Et₃N (0.12 g, 0.17 ml, 1.17 mmol) and isopropylisocyanate (0.075 g, 0.086 ml, 0.89 mmol) were added. The mixture was refluxed for 16 h, then 0.5 N NaOH (20 ml) was added and the mixture was extracted with CH₂Cl₂. The combined organic extracts were dried (MgSO₄), filtered, and concentrated. Purification by silica gel chromatography (eluant: 3% MeOH with NH₃—CH₂Cl₂) gave 0.22 g (0.37 mmol, 95%) of the product 53 (Ex. 8-B) as a white foam. MS (FAB for M+1): m/e 597.

The following compounds were prepared according to a similar procedure:

| Ex. | Compound | MS (Cl, FAB, or ES) |
|---|---|---|
| 8-C | 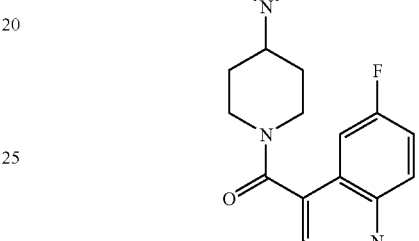 | 572 |
| 8-D | 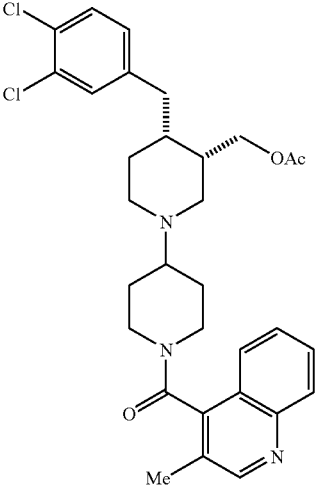 | 568 |

91
Example 9
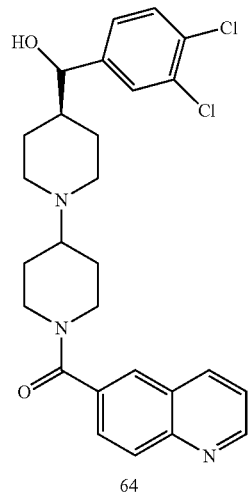
64
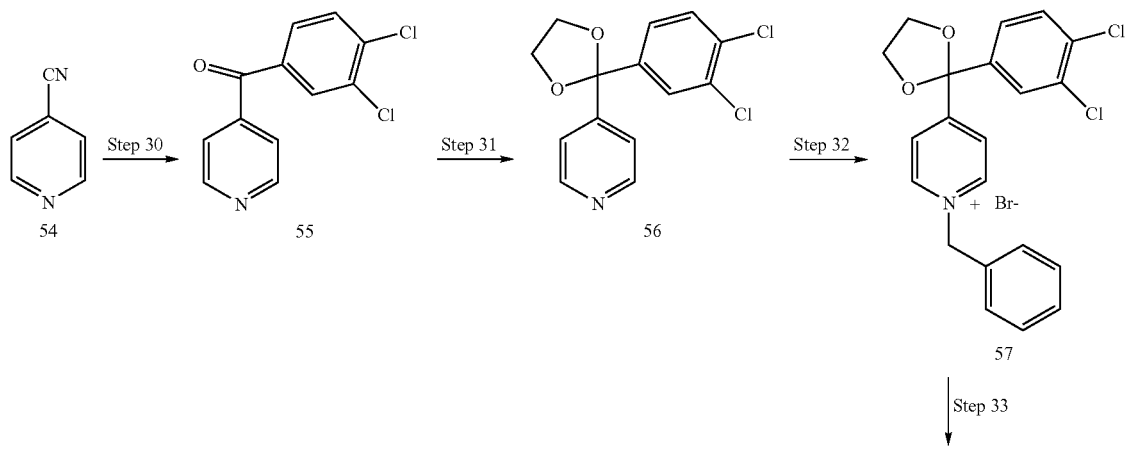
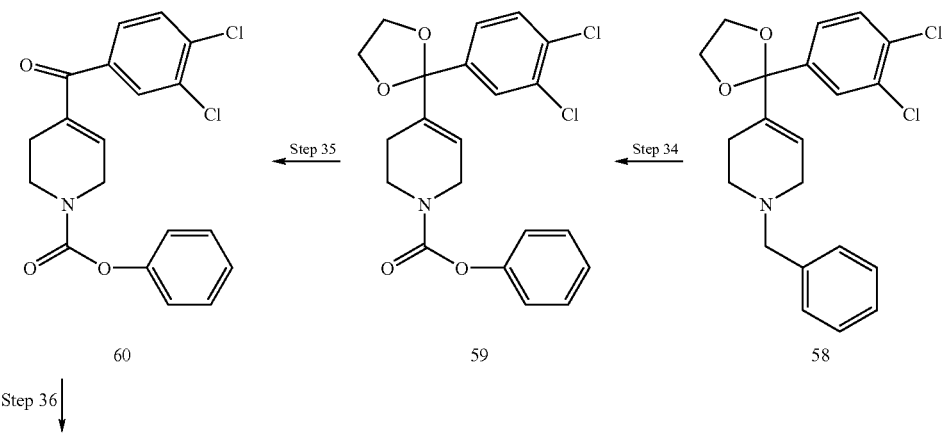

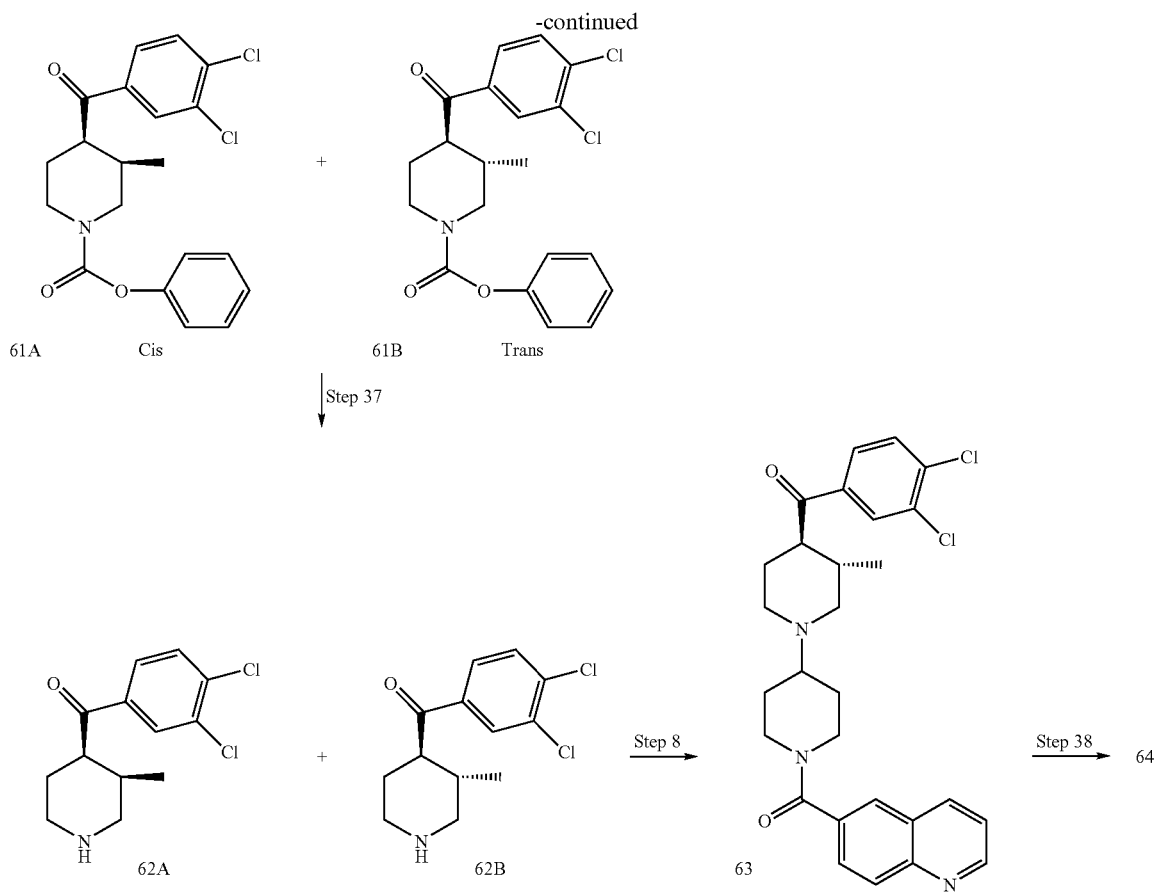

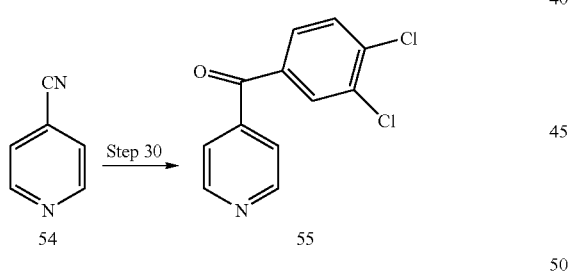

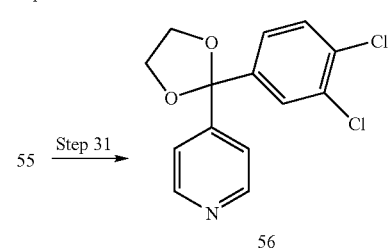

A solution of 1-bromo-3,4-dichlorobenzene (16.92 g, 0.074 mol) in Et$_2$O (100 ml) was added to a suspension of magnesium turnings in Et$_2$O (60 ml) and the mixture was refluxed for 1 hour. The reaction was cooled to 23° C. and a solution of 4-cyanopyridine 54 (7.80 g, 0.075 mol) in 1:1 Et$_2$O:THF (150 ml) was added rapidly with vigorous stirring. The mixture was refluxed for 24 h, then cooled to 23° C. Ice (100 g) was added, followed by 50% H$_2$SO$_4$ (50 ml), and the mixture was stirred for 1 h. Et$_2$O (100 ml) was added, the aqueous layer was separated, made basic with 10% NaOH, and extracted with EtOAc (2×250 ml). The combined organic layer was dried (Na$_2$SO$_4$), filtered, and concentrated. Purification by silica gel chromatography (eluant: 30% EtOAc: CH$_2$Cl$_2$) gave 12 g (0.047 mol, 64%) of the product 55 as a colorless oil. MS (FAB for M+1): m/e 252.

A mixture of compound 55 (10 g, 40 mmol), ethylene glycol (25 ml), and para-toluenesulfonic acid (8.56 g, 45 mmol) in toluene (200 ml) was refluxed for 36 h, using a Dean-Stark trap to remove water. The reaction was cooled to 23° C. and basified with 10% Na$_2$CO$_3$. The reaction was extracted with Et$_2$O, and the organic layer dried (MgSO$_4$), filtered and concentrated. Purification by silica gel chromatography (eluant: 30% EtOAc:CH$_2$Cl$_2$) gave 11 g (37 mmol, 100%) of the product 56 as a colorless oil. MS (FAB for M+1): m/e 296.

Step 32:

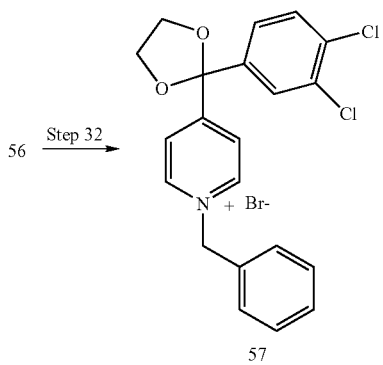

Benzyl bromide (7 ml, 58.5 mmol) was added to a solution of compound 56 (9 g, 30.5 mmol) in acetone (250 ml) at 23° C. then stirred for 16 h. Et$_2$O (300 ml) was added, and the precipitate filtered, washed with Et$_2$O (100 ml), and dried to give 9 g (23.3 mmol, 76%) of the product 57 as a white solid. MS (FAB for M+1): m/e 386.

Step 33:

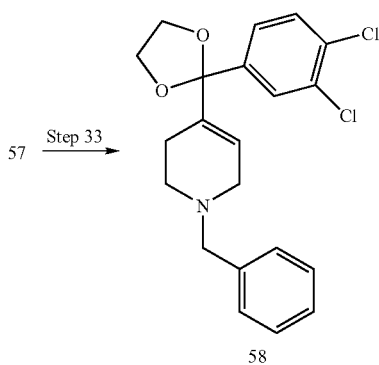

NaBH$_4$ (1 g, 27 mmol) was added to a solution of compound 57 (4 g, 10.33 mmol) in MeOH (80 ml) at 0° C., then warmed to 23° C., and stirred for 4 h. The solvent was evaporated, NaHCO$_3$ (100 ml) added, and the mixture extracted with CH$_2$Cl$_2$ (300 ml). The organic layer was separated, dried (MgSO$_4$), filtered, and concentrated. Purification by silica gel chromatography (eluant: 20% acetone-CH$_2$Cl$_2$) gave 3.5 g (8.97 mmol, 87%) of the product 58 as an oil. MS (FAB for M+1): m/e 391.

Step 34:

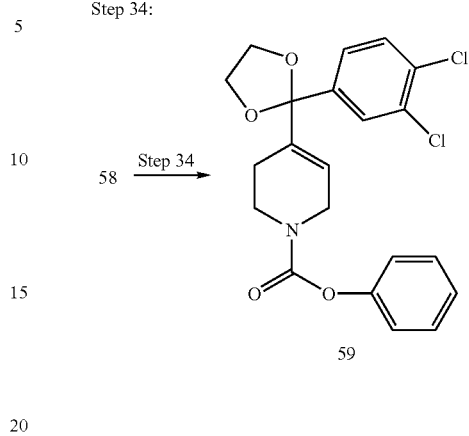

Phenyl chloroformate (3 ml, 23.8 mmol) was added to a solution of compound 58 (4.0 g, 10.2 mmol) and Et$_3$N (2 ml, 14.4 mmol) in 1,2-dichloroethane (40 ml) at 23° C. then refluxed for 1 h. The reaction was cooled, concentrated, water was added, the mixture extracted with CH$_2$Cl$_2$, dried (MgSO$_4$), filtered and concentrated. Purification by silica gel chromatography (eluant: 30% acetone-hexane) gave 4.1 g (9.78 mmol, 76%) of the product 59 as a white oil. MS (FAB for M+1): m/e 420.

Step 35:

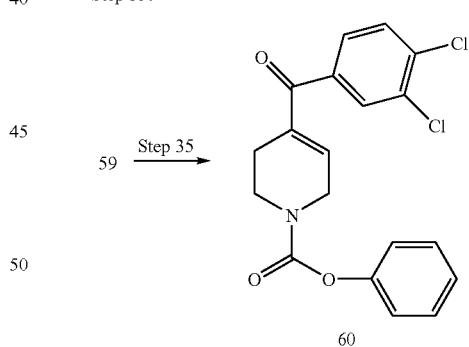

p-TSA (0.70 g, 3.67 mmol) was added to a solution of compound 59 (1.0 g, 2.38 mmol) in 3:1 acetone:water (20 ml) then refluxed for 3 h. The mixture was cooled and 5% Na$_2$CO$_3$ (50 ml) was added. The mixture was extracted with EtOAc, dried (Na$_2$SO$_4$), filtered, and concentrated to give 0.80 g (2.13 mmol, 89%) of the product 60. MS (FAB for M+1): m/e 376.

Step 36:

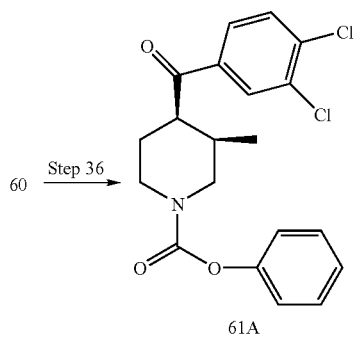

+

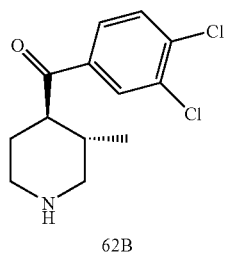

A solution of compounds 61A and 61B (2:1 mixture, 500 mg, 1.28 mmol) in 50% $H_2SO_4$ (20 ml) was refluxed for 4 h, then cooled to 23° C., diluted with water, and washed with $CH_2Cl_2$ (30 ml). The aqueous layer was basified with 10% NaOH, and extracted with $CH_2Cl_2$ (2×50 ml). The combined organic extracts were dried ($MgSO_4$), filtered and concentrated to give 345 mg (1.27 mmol, 99%) of the products 62A:62B (ratio 1:9) as a white solid. MS (FAB for M+1): m/e 272.

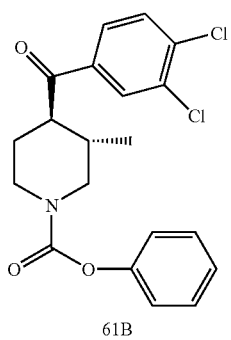

$CH_3Li$ (1.6 ml, 1.6 mmol) was added to a suspension of CuI (99%, 304 mg, 1.6 mmol) in dry $Et_2O$ (5 ml) at 10° C., then stirred at this temperature for 15 mins. The reaction was cooled to −50° C., and a solution of compound 60 (200 mg, 0.533 mmol) in $Et_2O$ (5 ml) was added. The reaction was stirred at −50° C. for 1 h, then warmed to 0° C. over a 1 h period. The reaction was quenched by addition of water (3 ml) and 10% $Na_2CO_3$ (10 ml). The organic layer was separated, dried ($Na_2SO_4$), filtered, and concentrated. Purification by silica gel chromatography (eluant: 25% acetone-hexane) gave 100 mg (0.256 mmol, 48%) of compound 61A as a white solid (FAB for M+1): m/e 391 and 45 mg (0.115 mmol, 22%) of compound 61B as a white solid. (FAB for M+1): m/e 391.

Step 8:

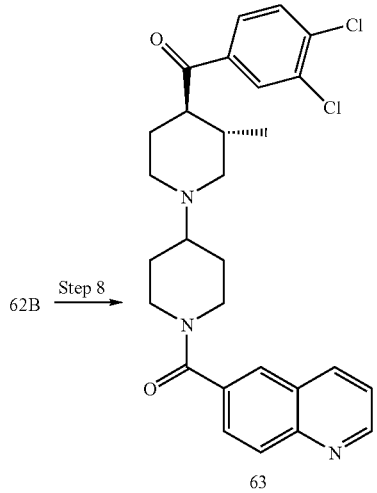

Using the same procedure as for Example 1, Step 8, compound 63 was prepared from compound 62B. MS (FAB for M+1): m/e 510.

Step 37:

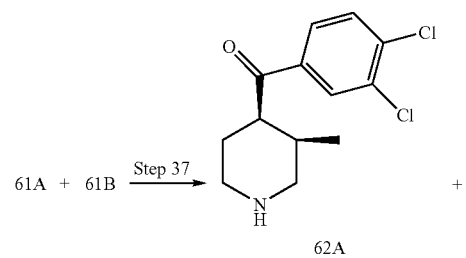

+

Step 38:

$NaBH_4$ (15 mg, 0.40 mmol) was added to a solution of compound 63 (150 mg, 0.29 mmol) in EtOH (5 ml) at 0° C., then stirred at 23° C. for 16 h. The resultant mixture was concentrated and $CH_2Cl_2$ (100 ml), water (50 ml) and 10% NaOH (2 ml) were added. The organic layer was separated, dried ($Na_2SO_4$), filtered, and concentrated. Purification by silica gel chromatography (eluant: 5% MeOH with $NH_3$—

CH$_2$Cl$_2$) gave 130 mg (0.25 mmol, 86%) of the product 64 as a mixture of isomers. MS (FAB for M+1): m/e 512.

Example 10

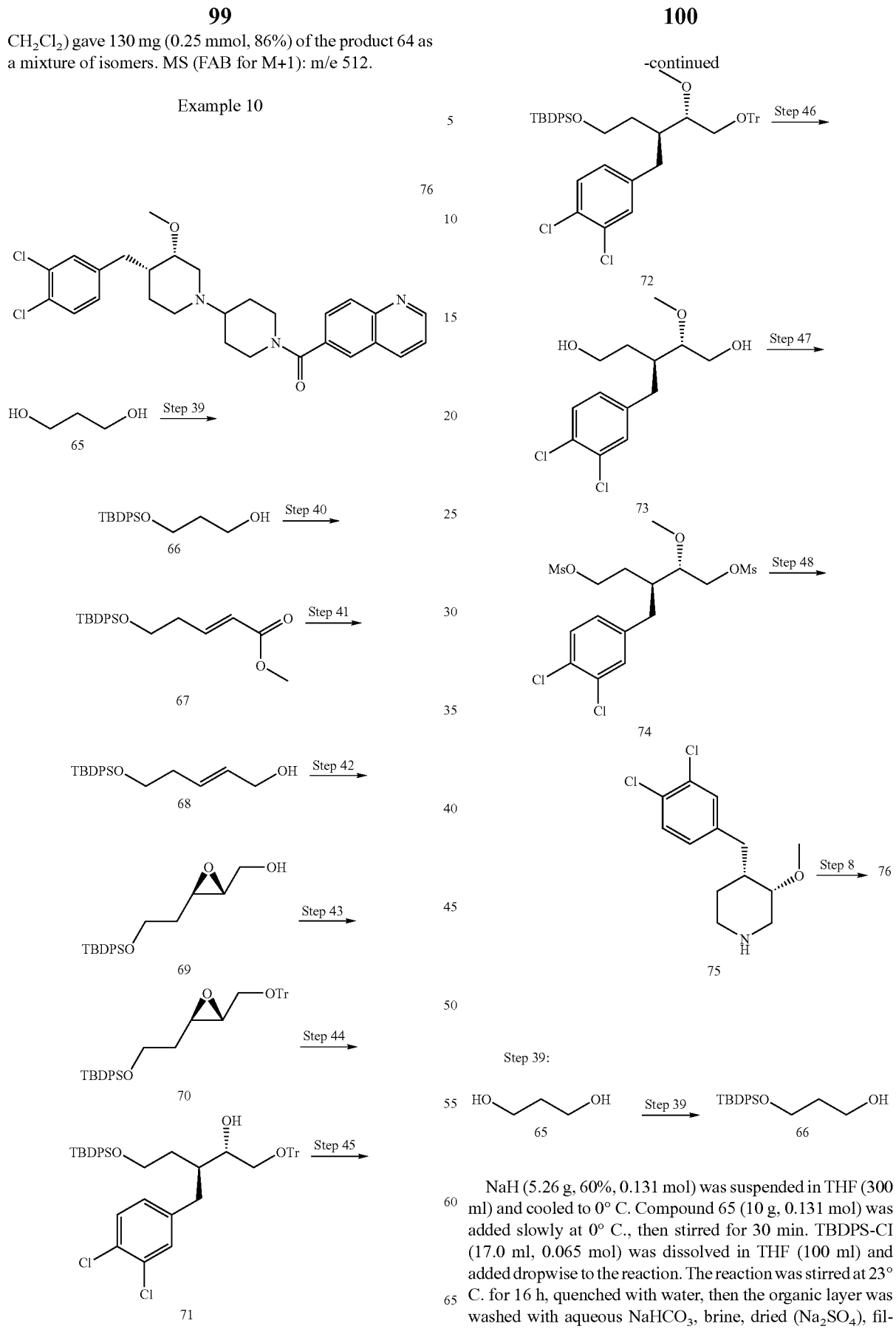

Step 39:

NaH (5.26 g, 60%, 0.131 mol) was suspended in THF (300 ml) and cooled to 0° C. Compound 65 (10 g, 0.131 mol) was added slowly at 0° C., then stirred for 30 min. TBDPS-Cl (17.0 ml, 0.065 mol) was dissolved in THF (100 ml) and added dropwise to the reaction. The reaction was stirred at 23° C. for 16 h, quenched with water, then the organic layer was washed with aqueous NaHCO$_3$, brine, dried (Na$_2$SO$_4$), filtered, and concentrated. Purification by silica gel chromatography (eluant: 10% EtOAc-hexane) gave 18.31 g (0.058 mol, 89%) of the product 66. MS (M+1): 315.

Step 40:

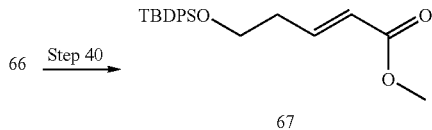

Oxalyl chloride (0.416 ml, 4.77 mmol) was dissolved in CH$_2$Cl$_2$ (30 ml), and cooled to –78° C. DMSO (0.338 ml, 4.77 mmol) was added dropwise and stirred at –78° C. for 15 min. Compound 66 (1.0 g, 3.18 mmol) was dissolved in CH$_2$Cl$_2$ (8 ml), and added dropwise. The mixture was stirred at –78° C. for 20 min. Et$_3$N (1.33 ml, 9.54 mmol) was added dropwise, and stirred at –78° C. for 40 min. Methyl(triphenyl-phosphoranylidene)acetate (1.59 g, 4.77 mmol) was dissolved in CH$_2$Cl$_2$ (8 ml), and added dropwise, and the mixture was stirred at –78° C. for 10 min, then at 23° C. for 16 h. The reaction mixture was diluted with Et$_2$O (100 ml) and the precipitate was filtered. The filtrate was washed with water, then brine, dried (Na$_2$SO$_4$), filtered, and concentrated. Purification by silica gel chromatography (eluant: 3% EtOAc-hexane) gave 0.65 g (55%) of the product 67. MS (M+1): 369.

Step 41:

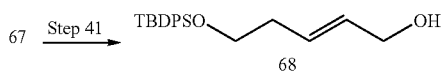

Compound 67 (0.65 g, 1.67 mmol) was dissolved in CH$_2$Cl$_2$ (10 ml) under N$_2$, and cooled to 0° C. DIBAL-H (4.53 ml 1.0 M in hexane, 4.53 mmol) was added dropwise and the mixture was stirred at 0° C. for 2 h. Saturated aqueous Na$_2$SO$_4$ (10 ml) was added and the mixture was filtered through a pad of celite. The filtrate was washed with brine, dried (Na$_2$SO$_4$), filtered, and concentrated. Purification by silica gel chromatography (eluant: 15% EtOAc-hexane) gave 420 mg (1.23 mmol, 70%) of the product 68. MS (LCMS for M+1)=341.

Step 42:

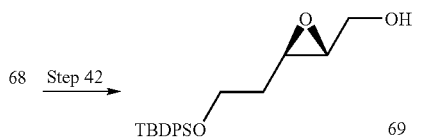

Compound 68 (6.0 g, 17.6 mmol) was dissolved in CH$_2$Cl$_2$ (150 ml) under N$_2$. Molecular sieves (7 g, 4 Å) were added, and cooled to –20° C. Titanium(IV) isopropoxide (5.2 ml, 17.6 mmol) was added, followed by diisopropyl D-tartrate (4.49 ml, 21.1 mmol), and the mixture was stirred at –20° C. for 40 min. tert-Butyl hydroperoxide (5.3 ml, 5.0-6.0 M in decane, 26.5-31.8 mmol) was added slowly, then stirred at –10° C. for 4 days. A freshly made solution of FeSO$_4$.7H$_2$O/citric acid (18 ml of 16.5 g/5.5 g in 50 ml of water) was added dropwise, and stirred at –10° C. for 1 h. The mixture was warmed to 23° C. and filtered through a pad of celite. The filtrate was washed with brine twice, dried (Na$_2$SO$_4$), filtered, and concentrated. Purification by silica gel chromatography (eluant: 10% EtOAc-hexane to 20% EtOAc-hexane) gave 1.49 g (4.18 mmol, pure) and 8.08 g (10.7 mmol, 47% mixture with diisopropyl D-tartrate) of the product 69 (combined yield 84%). MS (M+1): 357.

Step 43:

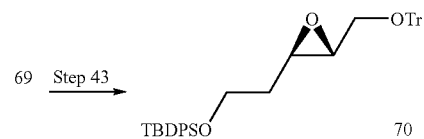

Compound 69 (6.62 g, 47%, 8.73 mmol) was dissolved in CH$_2$Cl$_2$ (300 ml). Et$_3$N (7.3 ml, 52.4 mmol) was added followed by triphenylmethyl chloride (7.3 g, 26.2 mmol), and DMAP (catalytic amount). The mixture was stirred at 23° C. for 16 h, then the solution was washed with water twice, then brine, dried (Na$_2$SO$_4$), filtered, and concentrated. Purification by silica gel chromatography (eluant: 3% EtOAc-hexane) gave 4.83 g (8.1 mmol, 92%) of the product 70. MS (M+1): 599.

Step 44:

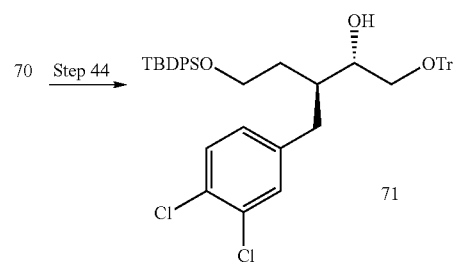

Mg (1.93 g, 79.4 mmol) was suspended in Et$_2$O (50 ml). A chip of I$_2$ was added, then heated to 45° C. 3,4-dichlorobenzylchloride (5.50 ml, 39.7 mmol) in Et$_2$O (50 ml) was added slowly and the mixture was stirred at 45° C. for 2 h, then cooled to 23° C. In a second flask, CuCN (71 mg, 0.79 mmol) was suspended in Et$_2$O (20 ml), then cooled to –30° C. under N$_2$. The Grignard reagent was cannulated into the second flask, then warmed to –15° C. Compound 70 (4.75 g, 7.94 mmol) in Et$_2$O (50 mL) was added dropwise. The mixture was stirred at –15° C. overnight, then warmed to 23° C. and stirred for 24 h. The reaction was quenched with 25% aqueous sodium citrate at 0° C. and the product extracted with EtOAc. The combined organic extracts were washed with brine, dried (Na$_2$SO$_4$), filtered, and concentrated. Purification by silica gel chromatography (eluant: 3% to 6% EtOAc:hexane) gave 3.73 g (4.9 mmol, 62%) of the product 71. MS (M+1): 759.

Step 45:

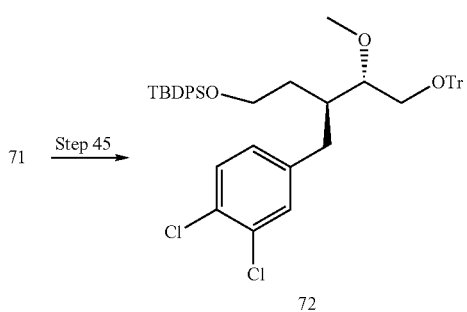

Compound 71 (1.5 g, 2.0 mmol) was dissolved in CH$_2$Cl$_2$ (5 ml) and cooled to 0° C. 2,6-di-tert-butyl pyridine (1.35 ml, 6 mmol) was added, followed by methyltriflate and the mixture was stirred at 23° C. for 16 h. The mixture was diluted with CH$_2$Cl$_2$, washed with water, brine, dried (Na$_2$SO$_4$), filtered, and concentrated. Purification by silica gel chromatography (eluant: 3% EtOAc-hexane) gave 1.35 g (87%) of the product 72. MS (M+23): 795.

Step 46:

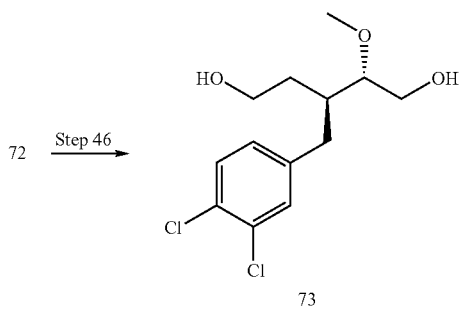

Compound 72 (1.35 g, 1.7 mmol) was dissolved in MeOH (10 ml) and CH$_2$Cl$_2$ (10 ml) and HCl in 1,4-dioxane (20 ml, 4 M) was added. The mixture was stirred at 23° C. for 30 min, then concentrated, redissolved in EtOAc, washed with aqueous NaHCO$_3$, brine, dried (Na$_2$SO$_4$), filtered, and concentrated. Purification by silica gel chromatography (eluant: 1:1 EtOAc-hexane, then 5% MeOH—CH$_2$Cl$_2$) gave 0.261 g (0.89 mmol, 52%) of the product 73. MS (M+1): 293.

Step 47:

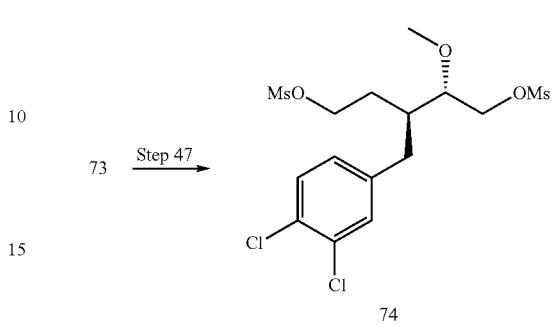

Compound 73 (0.261 g, 0.89 mmol) was dissolved in CH$_2$Cl$_2$ (10 ml), Et$_3$N (0.5 ml, 3.56 mmol) was added, and the mixture was cooled to 0° C. CH$_3$SO$_2$Cl (0.21 ml, 2.67 mmol) was added dropwise. The mixture was stirred at 0° C. for 1 h, then warmed to 23° C., diluted with CH$_2$Cl$_2$, washed with 1N HCl twice, brine, dried (Na$_2$SO$_4$), filtered, and concentrated to give 0.391 g (0.87 mmol, 98%) of the product 74. MS (M+23): 471.

Step 48:

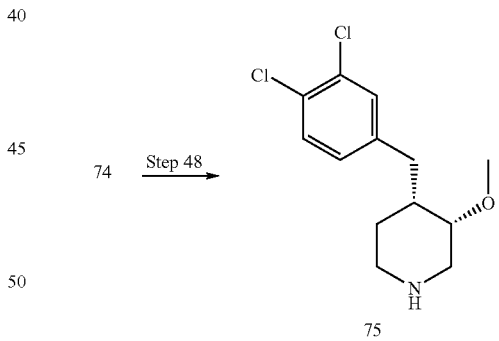

Compound 74 (0.391 g, 0.87 mmol) was dissolved in CH$_3$CN (15 ml) in a sealed tube. NH$_3$/H$_2$O (15 ml, 30%) was added. The tube was sealed and the mixture stirred at 23° C. for 3 days. CH$_3$CN was removed under vacuum, the resulting mixture was extracted with CH$_2$Cl$_2$, dried (Na$_2$SO$_4$), filtered, and concentrated. Purification by silica gel preparative TLC (eluant: 10% MeOH with NH$_3$—CH$_2$Cl$_2$) gave 76 mg (0.28 mmol, 32%) of the product 75. MS (M+1): 274.

Step 8:

75 →(Step 8)→

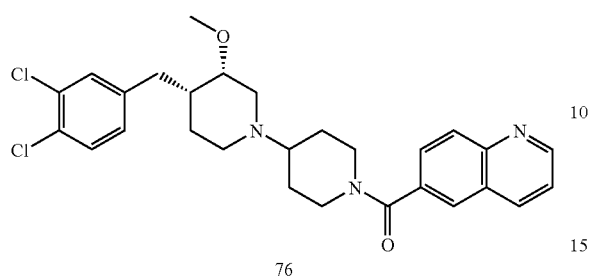

76

Using the same procedure as for Example 1, Step 8, compound 76 was prepared from compound 75. MS (M+1): m/e 513.

Example 11-A

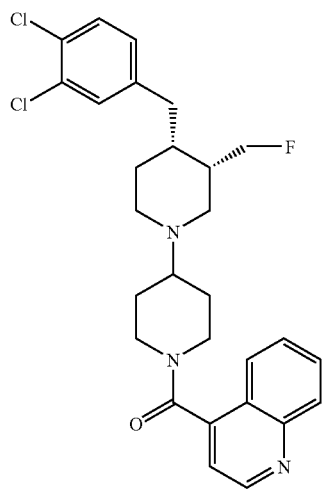

Step 49:

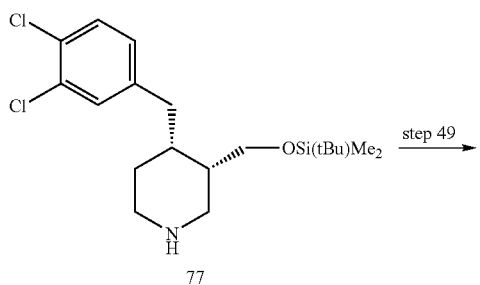

77

-continued

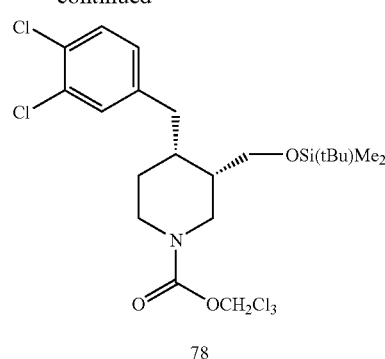

78

Et$_3$N (4 ml, 28.8 mmol) was added to a solution of compound 77 (4.0 g, 10.3 mmol) in CH$_2$Cl$_2$ (50 ml) at 23° C. Trichloroethyl chloroformate (4 ml, 29.1 mmol) was added, and the reaction stirred 23° C. for 16 h. Water (130 ml) and CH$_2$Cl$_2$ (200 ml) were added. The organic layer was separated, dried (MgSO$_4$), filtered, and concentrated. Purification by silica gel chromatography (eluant: 20% v/v acetone:CH$_2$Cl$_2$) gave 4.0 g (68%) of the product 78 as an oil. MS (FAB for M+1): m/e 564.

Step 50:

78 →(Step 50)→

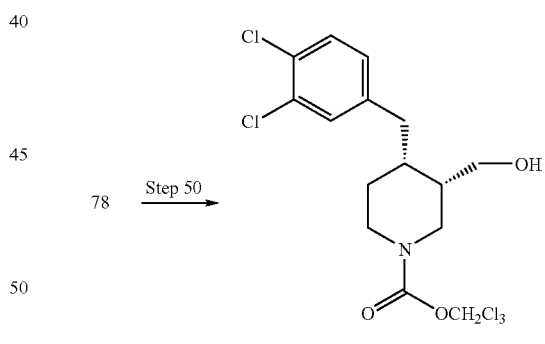

79

Tetrabutylammonium fluoride (1.0 M in THF, 15 ml, 15 mmol) was added to a solution of compound 78 (4.0 g, 7.10 mmol) in CH$_2$Cl$_2$ (20 ml) and stirred at 23° C. for 16 h. Water (100 ml) and CH$_2$Cl$_2$ (200 ml) were added. The organic layer was separated, dried (MgSO$_4$), filtered, and concentrated. Purification by silica gel chromatography (eluant: 20% v/v acetone:CH$_2$Cl$_2$) gave 2.5 g (94%) of the product 79 as an oil.

Step 51:

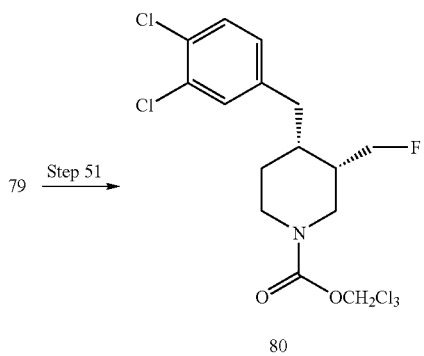

Bis-(2-methoxyethyl)amino-sulfur trifluoride (1.0 ml, 5.4 mmol) was added to a solution of compound 79 (1.0 g, 2.65 mmol) in CH$_2$Cl$_2$ (10 ml) at 0° C. and the mixture was then stirred at 23° C. for 16 h. Water (10 ml) and 10% Na$_2$CO$_3$ (10 ml) were added and the mixture was extracted with CH$_2$Cl$_2$ (100 ml). The organic layer was separated, dried (MgSO$_4$), filtered and concentrated. Purification by silica gel chromatography (eluant: 1:5:5 acetone:CH$_2$Cl$_2$:hexanes) gave 0.60 g (1.33 mmol, 50%) of the product 80 as an oil. MS (FAB for M+1): m/e 450.

Step 52:

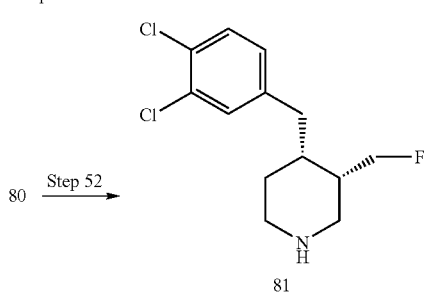

A suspension of compound 80 (300 mg, 0.668 mmol) and zinc metal (250 mg, 3.83 mmol) in glacial AcOH (5 ml) was stirred at 70° C. for 1 h. The reaction was cooled and concentrated. Water (50 ml) and 10% NaOH (5 ml) were added and the mixture was extracted with CH$_2$Cl$_2$ (100 ml). The organic layer was separated, dried (MgSO$_4$), filtered, and concentrated to give 150 mg (0.54 mmol, 81%) of the product 81. MS (FAB for M+1): m/e 276.

Step 8:

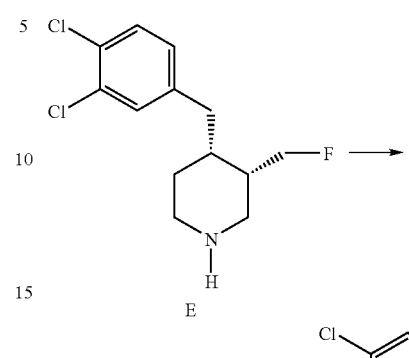

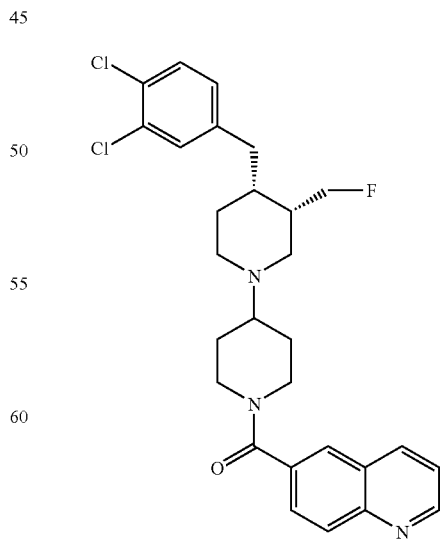

Using the same procedure as for Example 1, Step 8, the compound of Example 11-A was prepared. MS: m/e 514.

Using a similar procedure, the compound of Example 11-B was prepared:

Ex. 11-B. MS: m/e 514.

Example 12
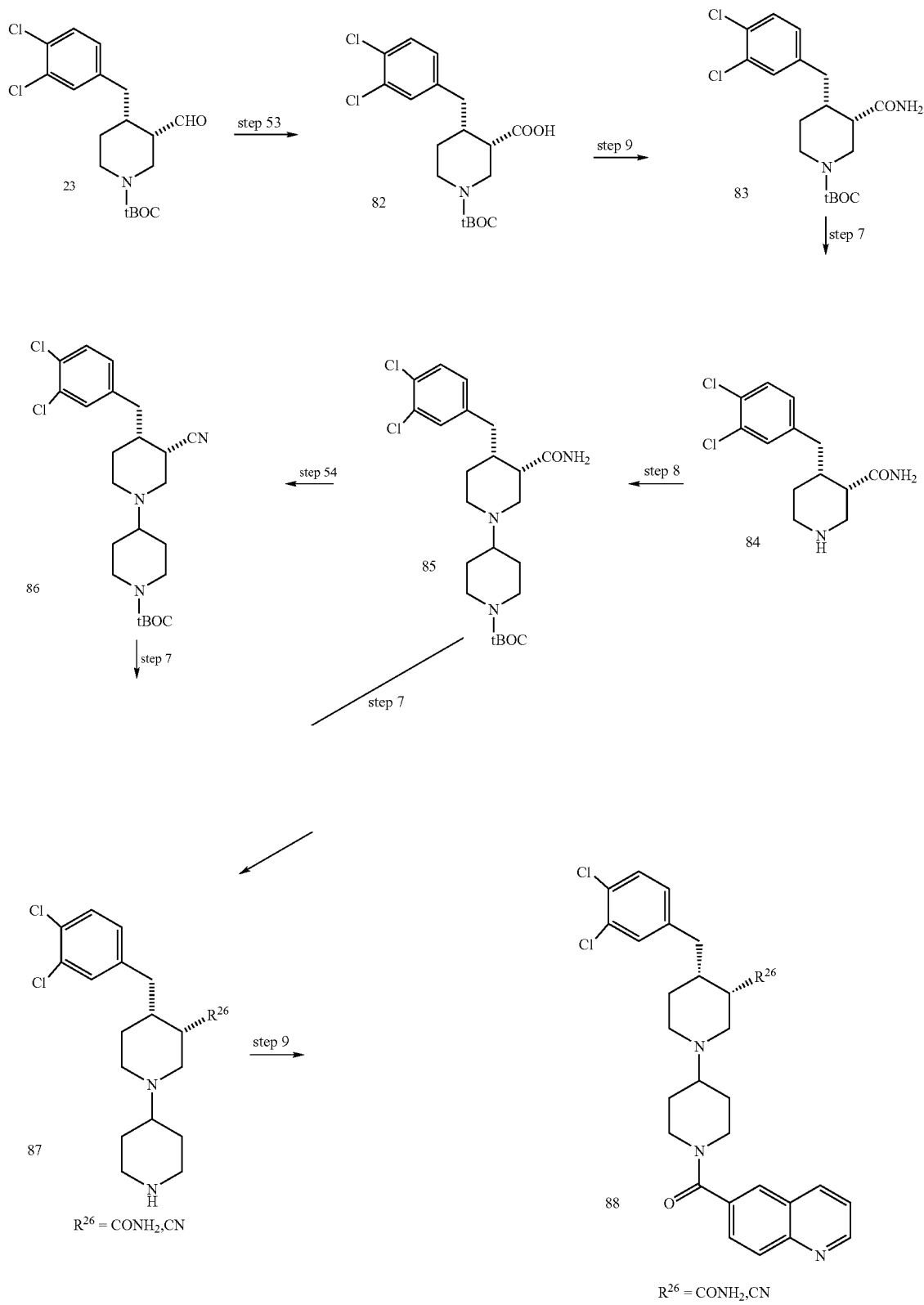

Step 53:

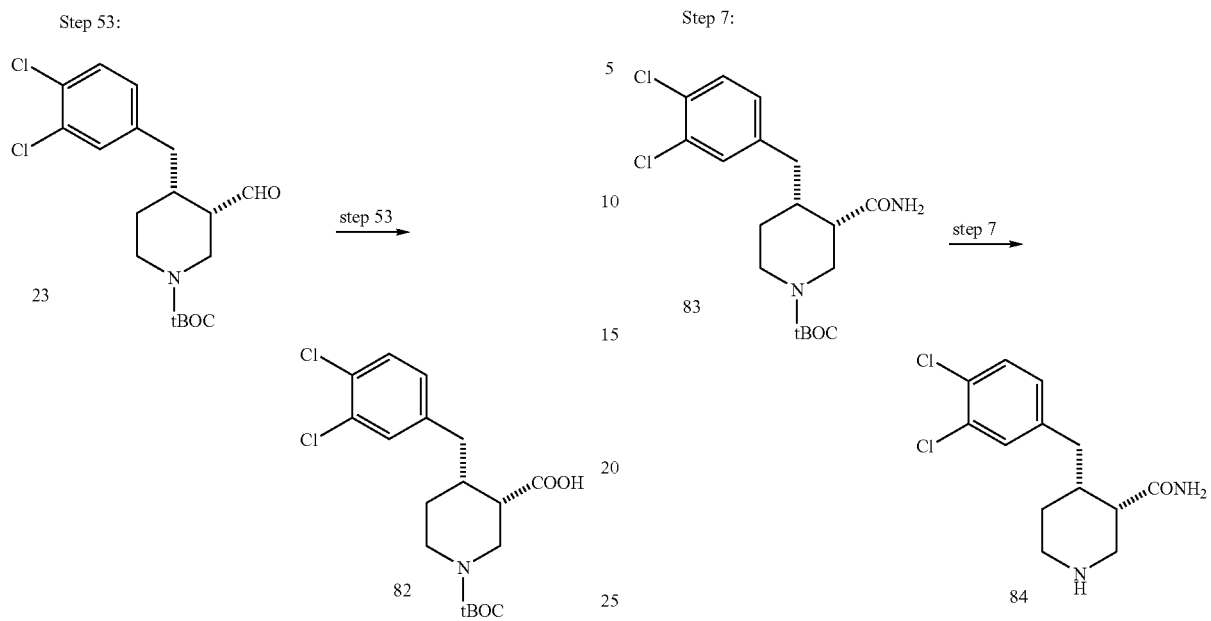

Compound 23 (5.00 g, 13.5 mmol) was dissolved in acetone (60 ml) and potassium permanganate (4.50 g, 28.5 mmol) in water (200 ml) was added. The reaction mixture was stirred at 23° C. for 3 h. Sodium bisulfate (50 g) was added until a colorless solution was obtained. The resultant mixture was filtered, the solid was washed with water, and the filtrate was extracted with $CH_2Cl_2$. The combined organic extracts were dried ($MgSO_4$), filtered, and concentrated to give 4.60 g (11.9 mmol, 88%) of the product 82 as a white solid. MS (ES for M+1): m/e 388.

Step 9:

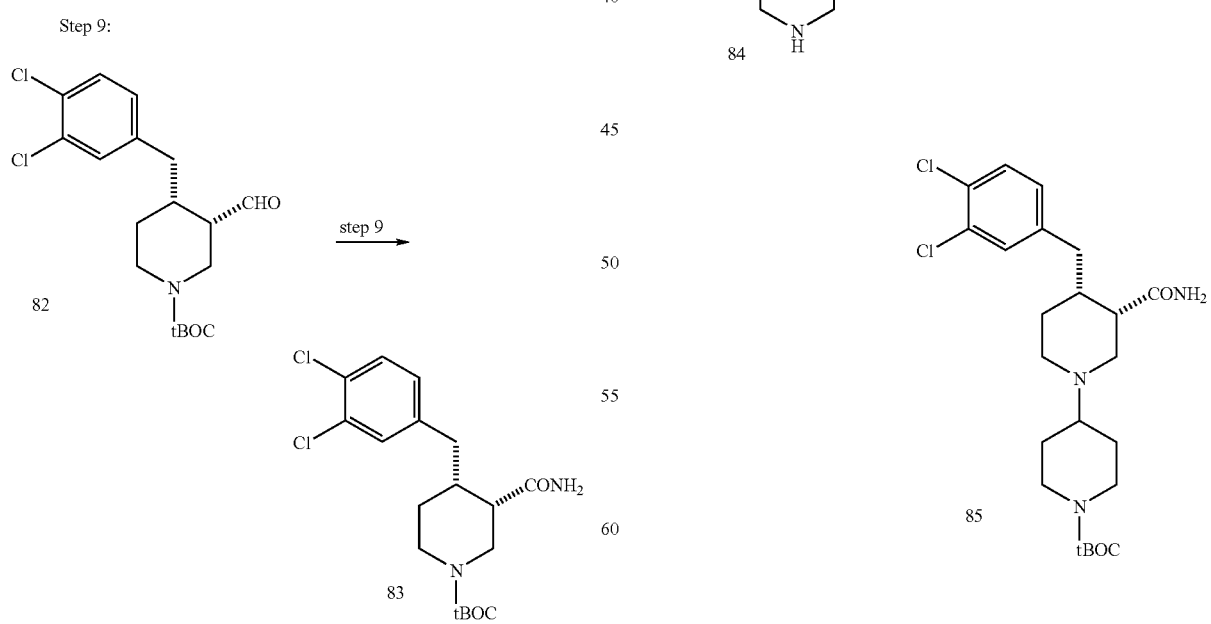

Using the same procedure as for Example 1, Step 9, compound 83 was prepared. MS (ES for M+1): m/e 387.

Using the same procedure as for Example 1, Step 7, compound 84 was prepared. MS (ES for M+1): m/e 287.

Using the same procedure as for Example 1, Step 8, compound 85 was prepared. MS (ES for M+1): m/e 470.

Step 54:

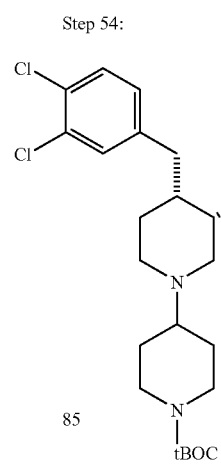

85

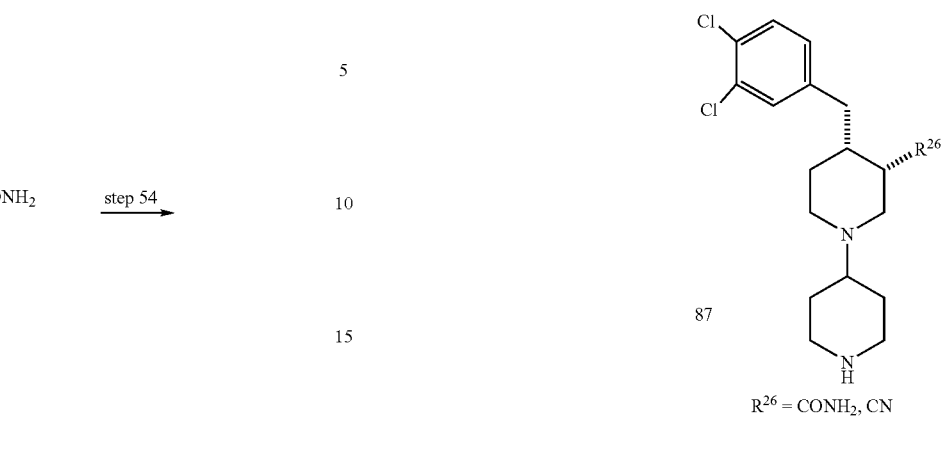

86

Compound 85 (1.00 g, 2.13 mmol) was dissolved in $CH_2Cl_2$ (10 ml) and Burgess reagent (1.78 g, 7.45 mmol) was added portionwise. The reaction mixture was stirred at 23° C. for 16 h. The solvent was evaporated, and the crude product was purified by silica gel chromatography (eluant: 3% MeOH—$CH_2Cl_2$) to give the product 86 as an oil. MS (M+1): m/e 452.

Step 7:

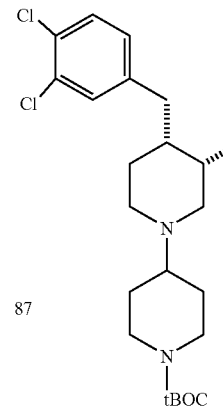

87

$R^{26} = CONH_2, CN$

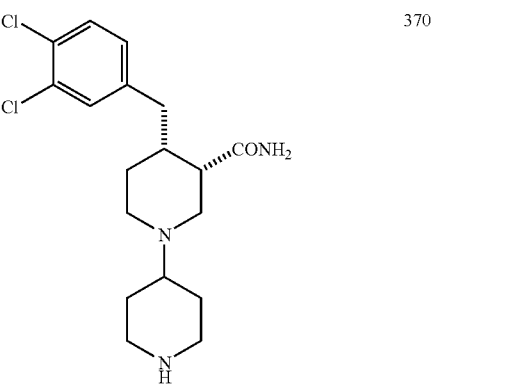

87

$R^{26} = CONH_2, CN$

Using the same procedure as for Example 1, Step 7, the following intermediates were prepared.

| Compound | MS (Cl, FAB, or ES) |
|---|---|
|  | 370 |
|  | 352 |

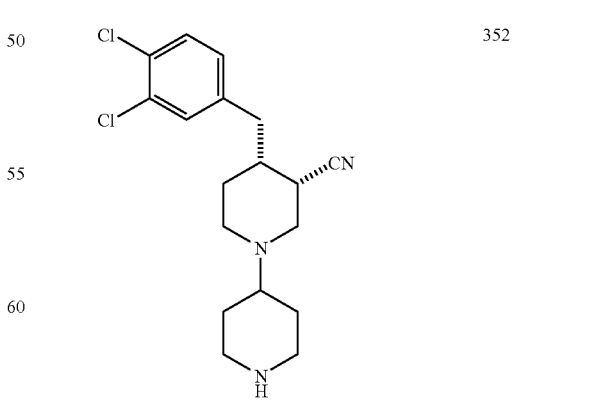

Step 9:
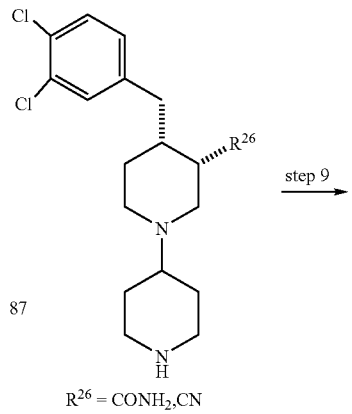
Using the same procedure as for Example 1, Step 9, the following compounds were prepared.
| Ex. | Compound | MS (Cl, FAB, or ES) |
|---|---|---|
| 12-A | | 525 |
| 12-B | | 525 |
| 12-C | | 525 |

| Ex. | Compound | MS (Cl, FAB, or ES) |
|---|---|---|
| 12-D | 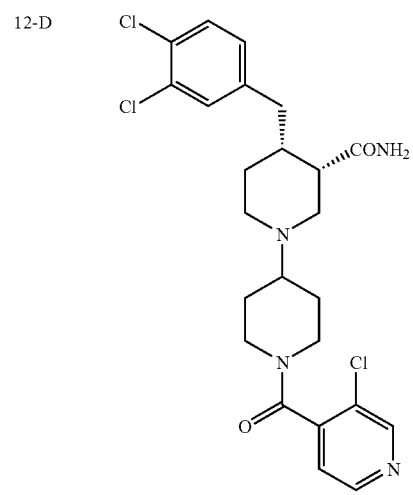 | 509 |
| 12-E | 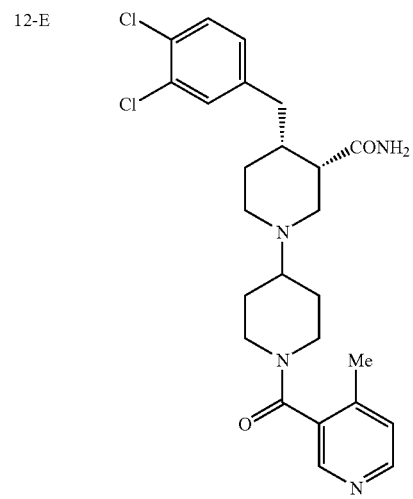 | 489 |
| 12-F | 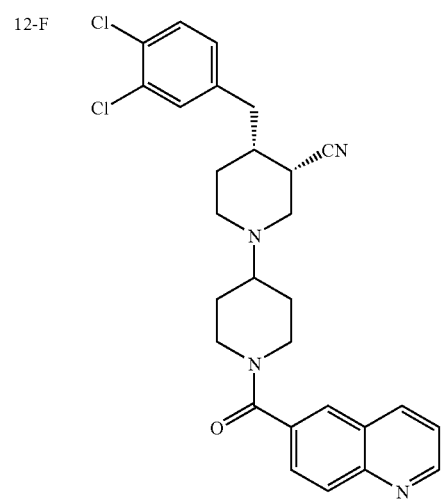 | 507 |
| Ex. | Compound | MS (Cl, FAB, or ES) |
|---|---|---|
| 12-G | 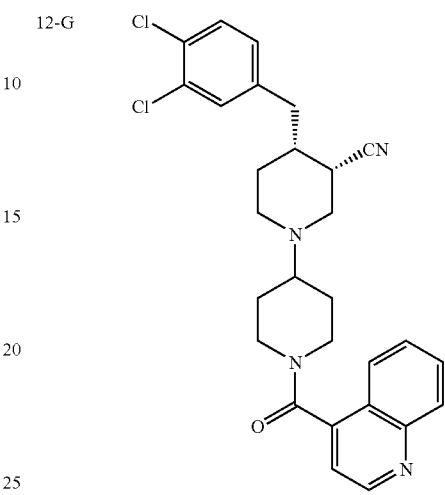 | 507 |
| 12-H | 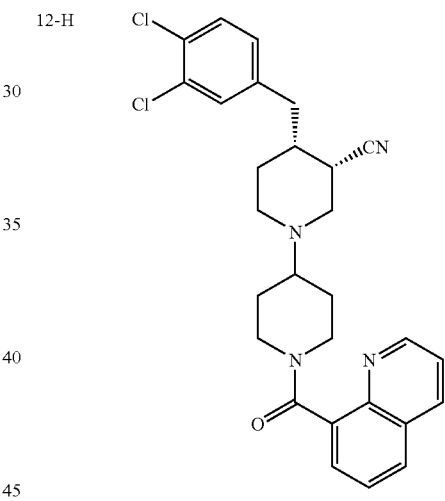 | 507 |
| 12-I | 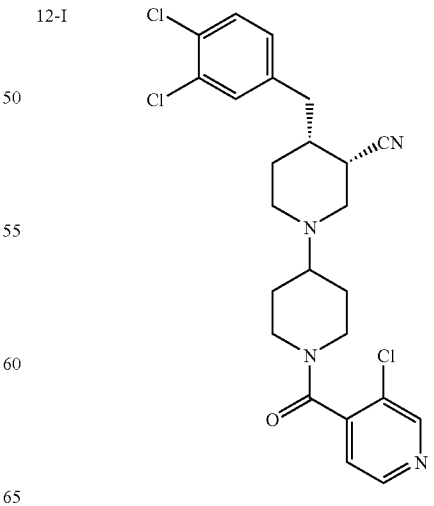 | 491 |

Example 13
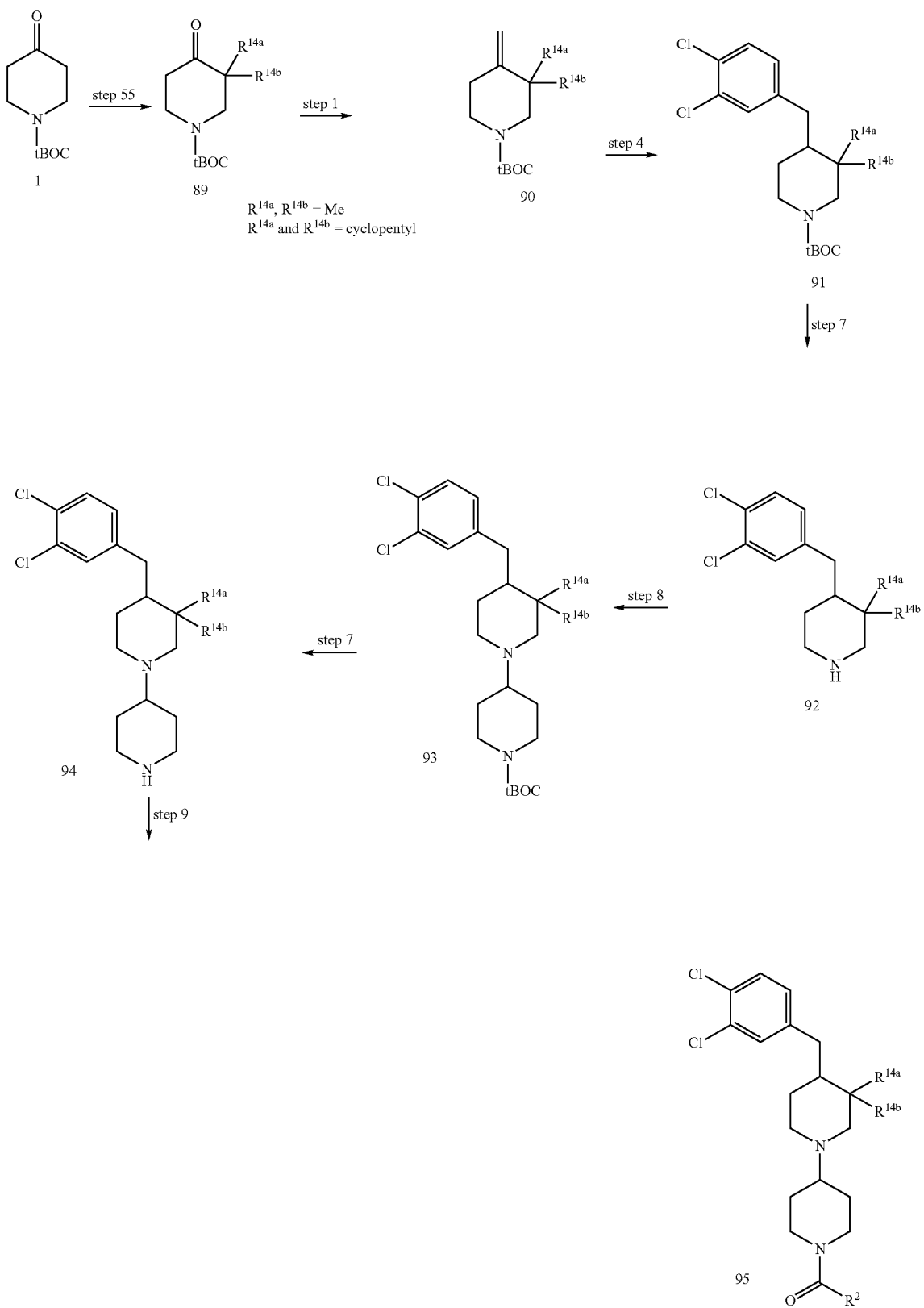

Step 55:

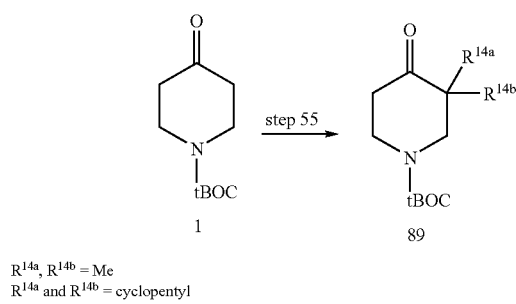

$R^{14a}$, $R^{14b}$ = Me
$R^{14a}$ and $R^{14b}$ = cyclopentyl

Compound 1 (15.95 g, 0.080 mol) was dissolved in THF (400 ml) under a $N_2$ atmosphere and cooled to 0° C. NaH (6.72 g, 60% in oil, 0.168 mol) was added portionwise, and the reaction mixture was stirred at 0° C. for 30 mins. $CH_3I$ (28.5 g, 12.5 ml, 0.201 mol) was added, and the reaction mixture was stirred at 23° C. for 48 h. The solvent was removed, water was added, and the resultant mixture was extracted with $Et_2O$. The combined organic extracts were dried ($MgSO_4$), filtered, and concentrated. The crude product was recrystallized twice from pentane to give 8.97 g (0.039 mol, 49%) of the product 89 as a white solid. Purification of the mother liquor by silica gel chromatography (eluant: 5% EtOAc-hexane to 20% EtOAc-hexane) gave an additional 5.00 g (0.022 mol, 27%) of the product 89 as a white solid. MS (M+1): m/e 228.

Using a similar procedure, the following intermediate was prepared:

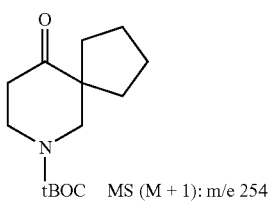 MS (M + 1): m/e 254

Step 1:

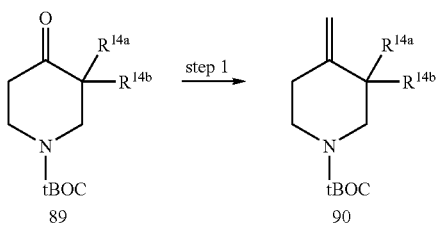

$R^{14a}$, $R^{14b}$ = Me
$R^{14a}$ and $R^{14b}$ = cyclopentyl

Using the same procedure as for Example 1, Step 1, the following intermediates were prepared.

| Compound | MS (Cl, FAB, or ES) |
|---|---|
| ![structure] | 226 |
| ![structure] | 252 |

Step 4:

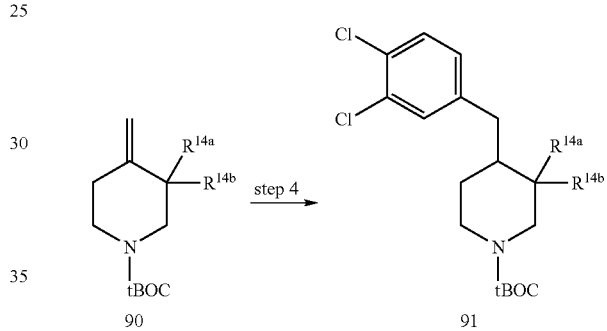

Using the same procedure as for Example 1, Step 4, the following intermediates were prepared:

| Compound | MS (Cl, FAB, or ES) |
|---|---|
| ![structure] | M + 2-tBu(57) = 316 |
| ![structure] | 398 |

-continued
| Compound | MS (Cl, FAB, or ES) |
|---|---|
Step 7:
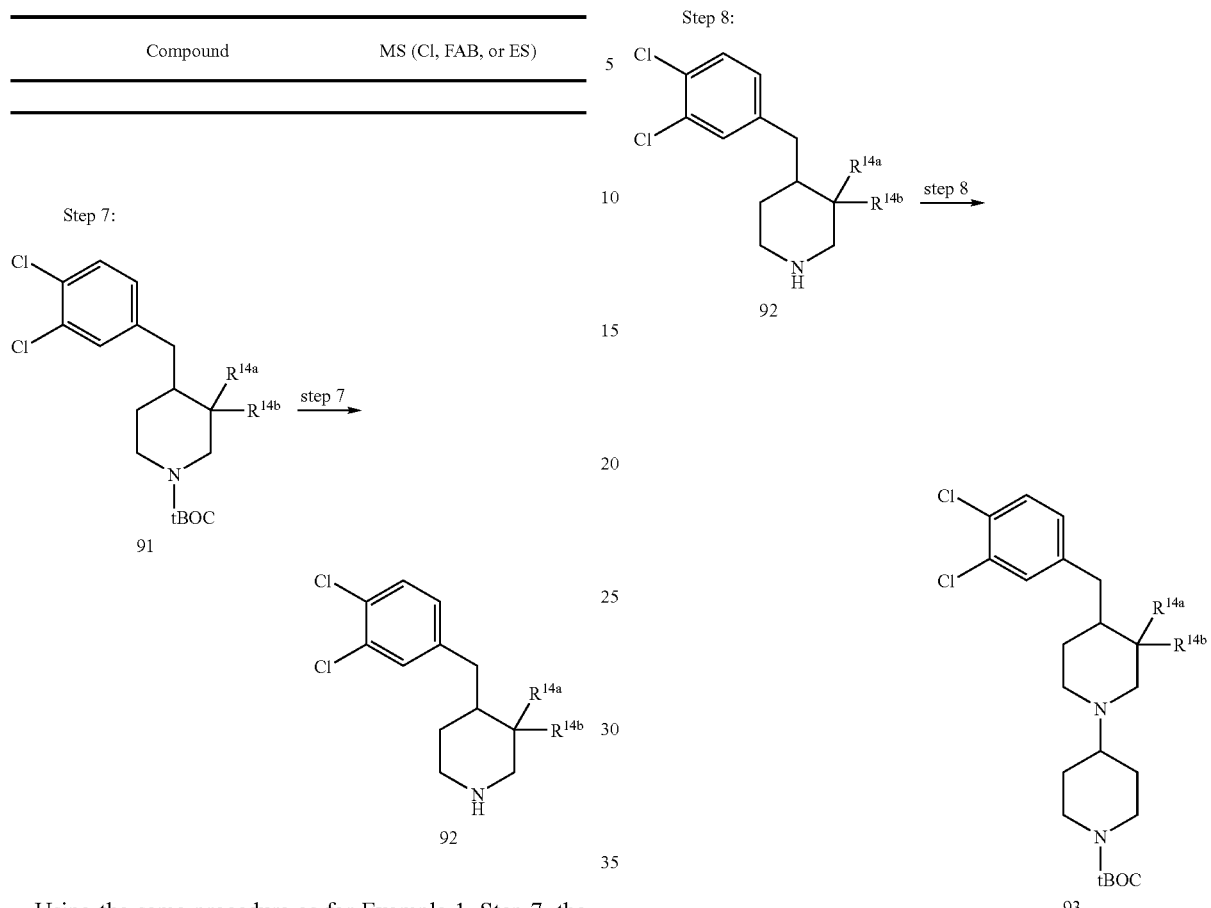
Using the same procedure as for Example 1, Step 7, the following intermediates were prepared.
| Compound | MS (Cl, FAB, or ES) |
|---|---|
| 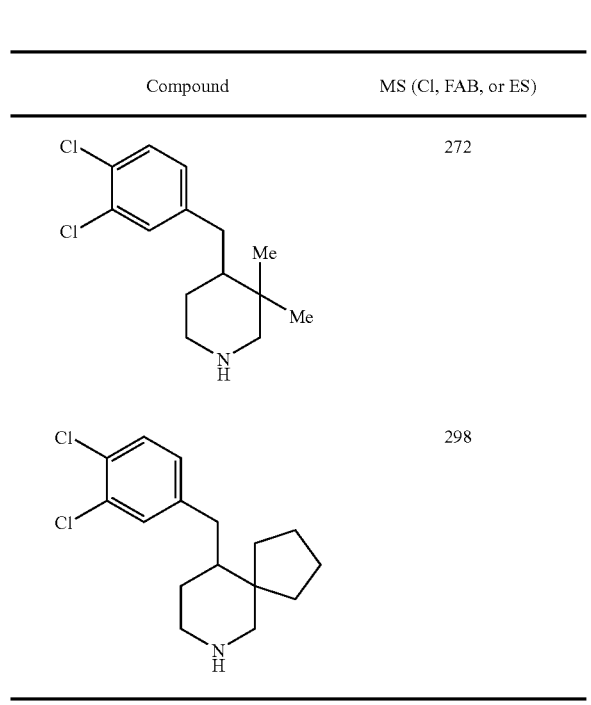 | 272 |
| | 298 |
Using the same procedure as for Example 1, Step 8, the following intermediates were prepared.
| Compound | MS (Cl, FAB, or ES) |
|---|---|
| 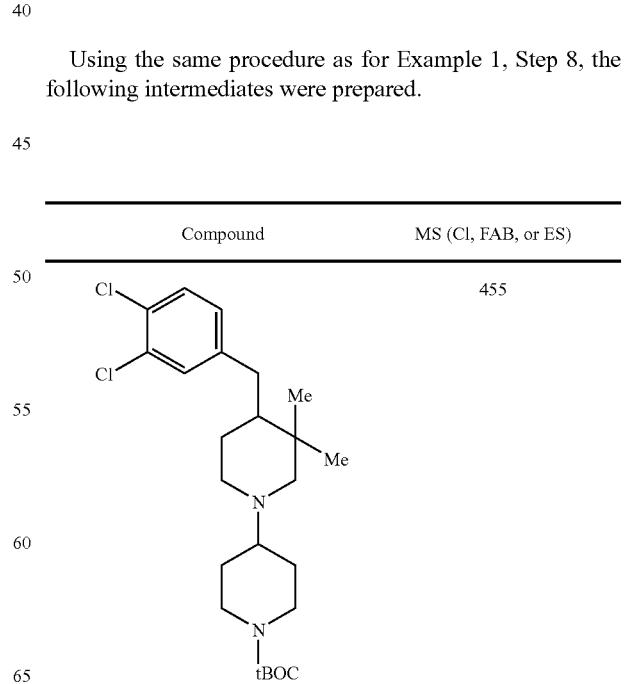 | 455 |

-continued
| Compound | MS (Cl, FAB, or ES) |
|---|---|
| 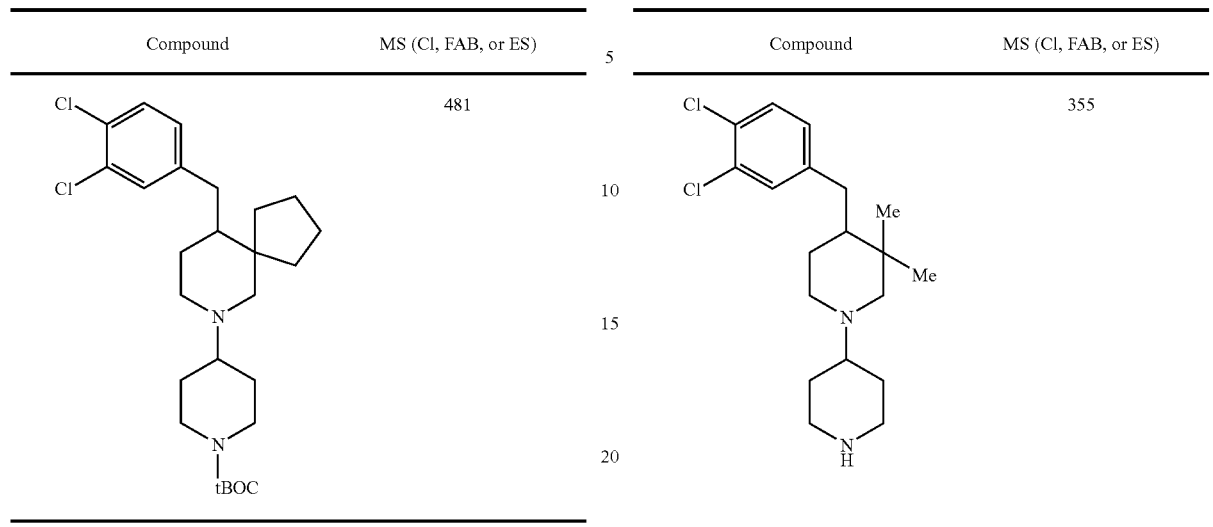 | 481 |
Step 7:
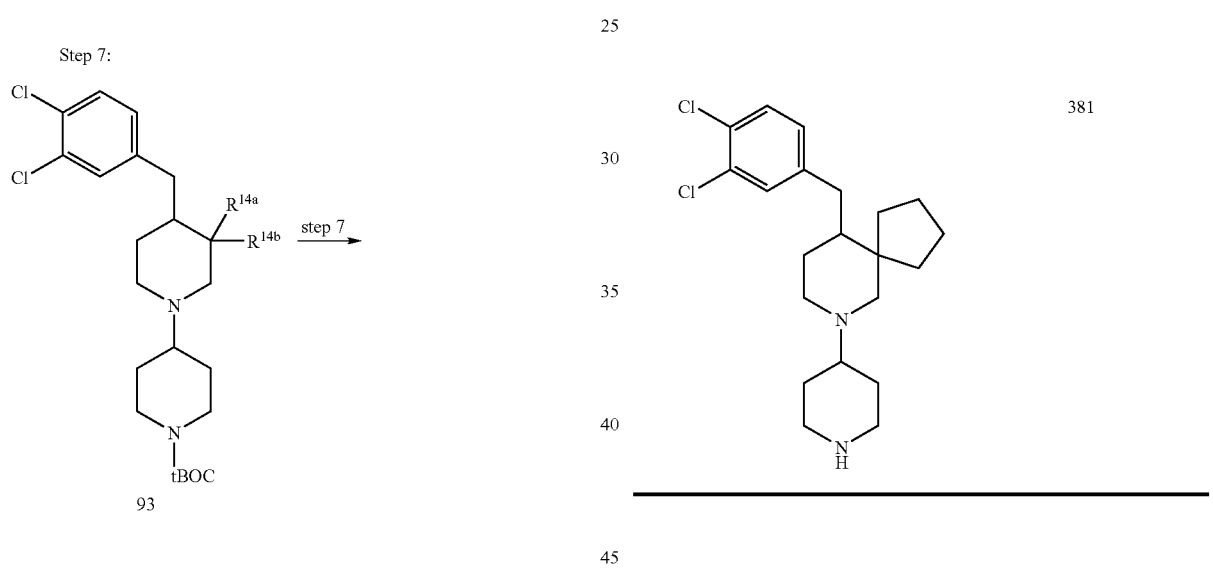
Using the same procedure as for Example 1, Step 7, the following intermediates were prepared.
| Compound | MS (Cl, FAB, or ES) |
|---|---|
| (compound with Me, Me substituents) | 355 |
| (spiro compound) | 381 |
Step 9:
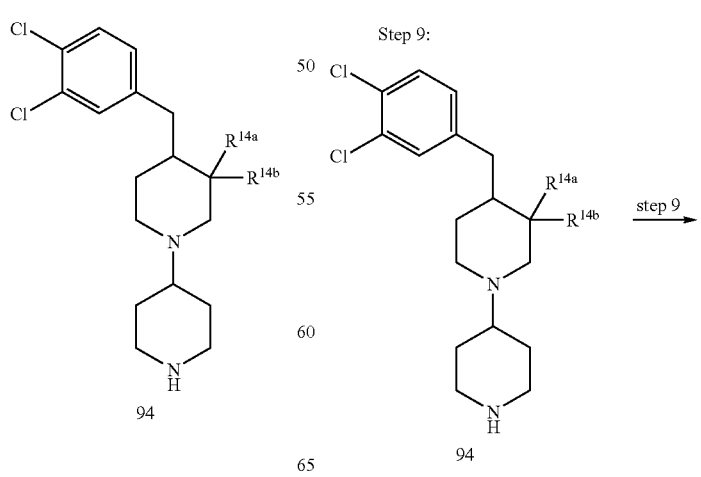

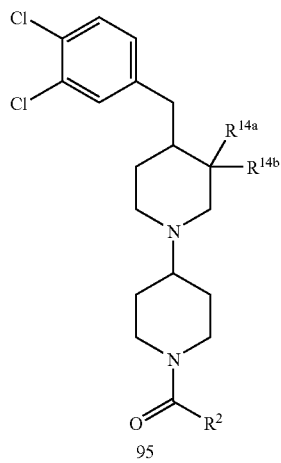
Using the same procedure as for Example 1, Step 9, the following compounds were prepared.
| Ex. | Compound | MS (Cl, FAB, or ES) |
|---|---|---|
| 13-A | 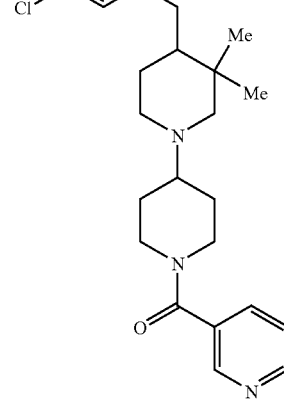 | 510 |
| 13-B | | 510 |
| 13-C | | 510 |
| 13-D | | 510 |
| 13-E | | 511 |

-continued
| Ex. | Compound | MS (Cl, FAB, or ES) |
|---|---|---|
| 13-F | 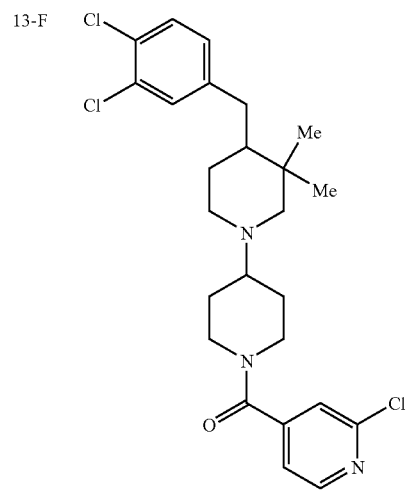 | 494 |
| 13-G | 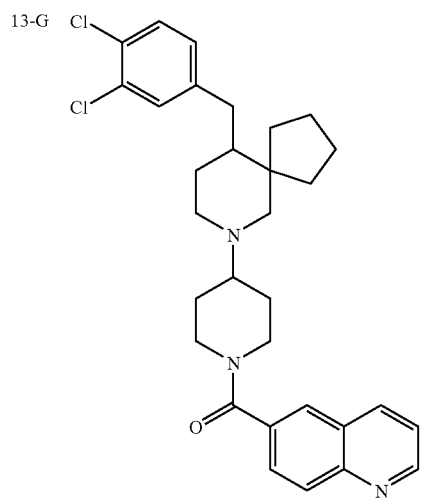 | 536 |
| 13-H | 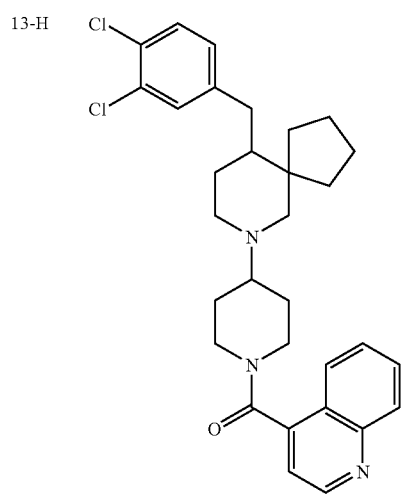 | 536 |
-continued
| Ex. | Compound | MS (Cl, FAB, or ES) |
|---|---|---|
| 13-I | 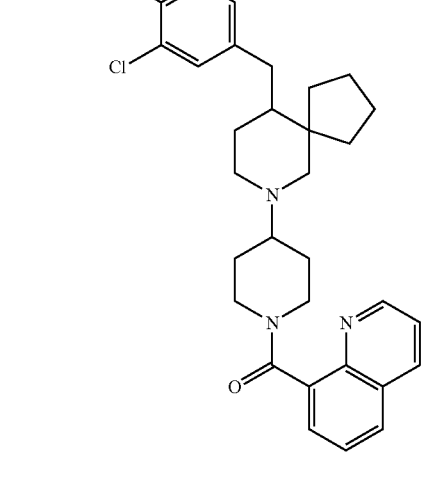 | 536 |
| 13-J | 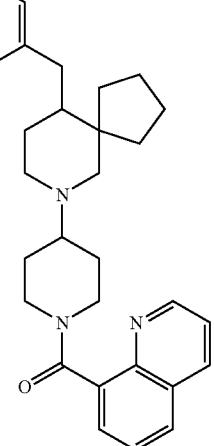 | 500 |

-continued
| Ex. | Compound | MS (Cl, FAB, or ES) |
|---|---|---|
| 13-K | 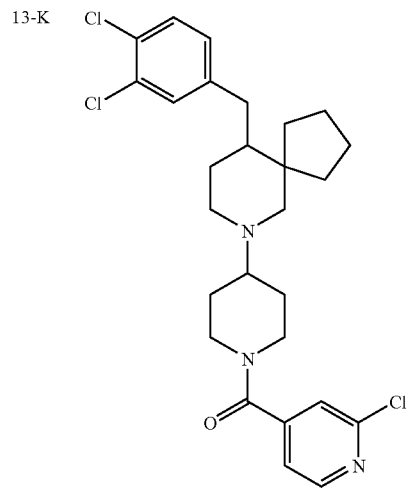 | 520 |
-continued
| Ex. | Compound | MS (Cl, FAB, or ES) |
|---|---|---|
| | 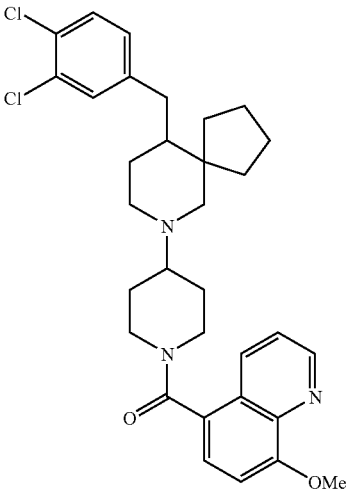 | 566 |
Example 14
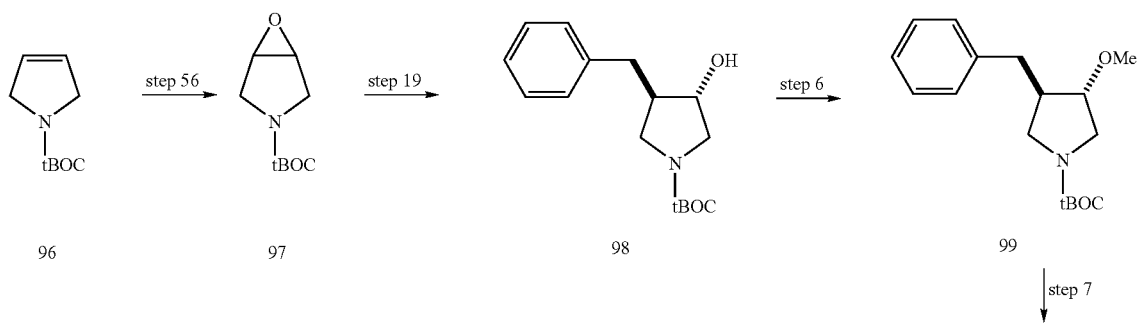
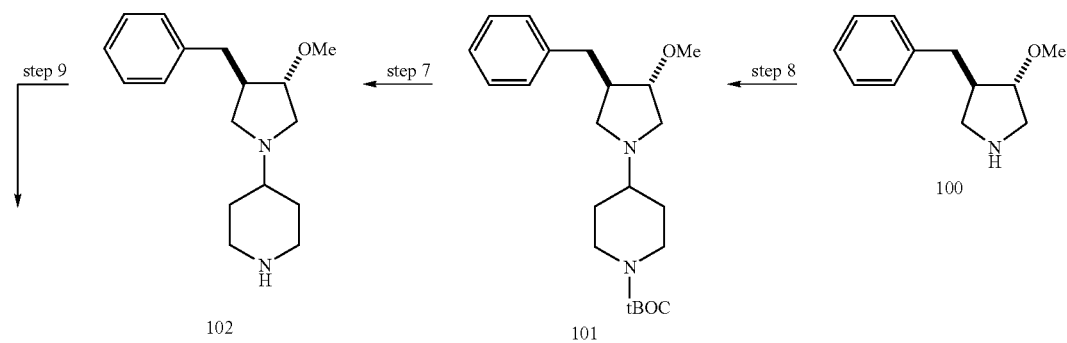

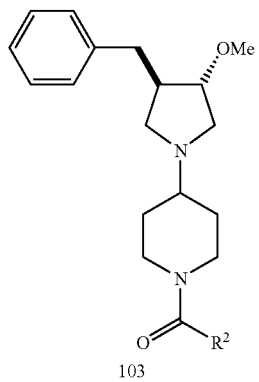

103

Step 56:

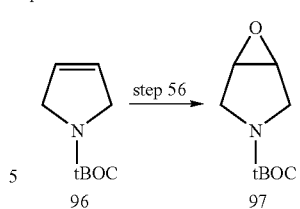

Compound 96 (7.28 g, 43.0 mmol) was dissolved in CH$_2$Cl$_2$ (170 ml) and cooled to 0° C. MCPBA (11.87 g of 75% MCPBA, 51.6 mmol) was added portionwise. The reaction mixture was stirred at 23° C. for 16 h. CH$_2$Cl$_2$ (150 ml) was added and the organic solution was washed three times with 1 N NaOH, once with water, and once with brine. The organic solution was dried (MgSO$_4$), filtered, and concentrated. Purification by silica gel chromatography (eluant: 1:5 EtOAc:PHCH$_3$) gave 3.89 g (20.4 mmol, 47%) of the product 97 as a colorless oil.

Step 19:

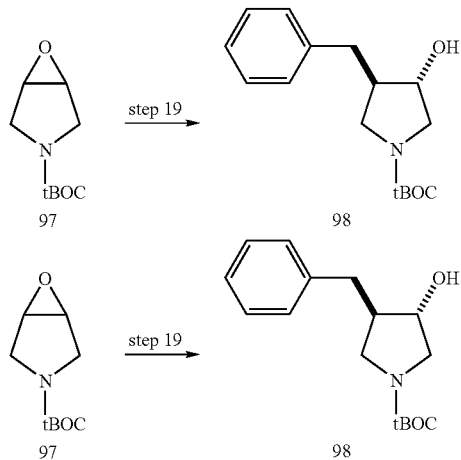

Using the same procedure as for Example 4-B, Step 19, the following intermediates were prepared.

| Compound | MS (Cl, FAB, or ES) |
|---|---|
| (benzyl-hydroxy-pyrrolidine-tBOC) | 278 |
| (dichlorobenzyl-hydroxy-pyrrolidine-tBOC) | 346 |

Step 6:

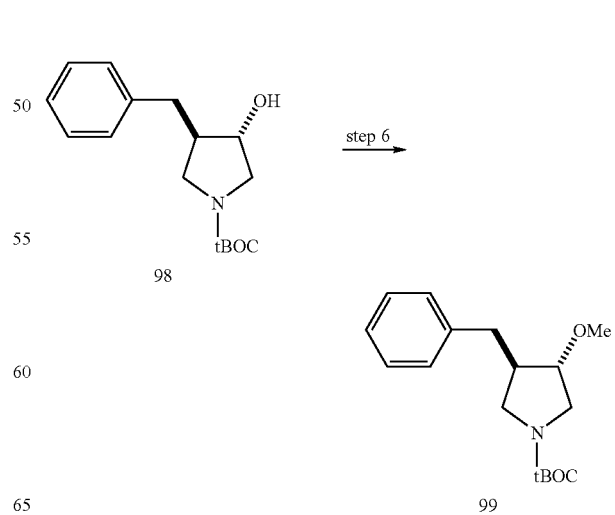

Using the same procedure as for Example 1, Step 6, the following intermediates were prepared.

| Compound | MS (Cl, FAB, or ES) |
|---|---|
| benzyl-OMe-pyrrolidine-tBOC | 292 |
| 3,4-dichlorobenzyl-OMe-pyrrolidine-tBOC | 360 |

Step 7:

benzyl-OMe-pyrrolidine-tBOC (99) →step 7→ benzyl-OMe-pyrrolidine-NH (100)

Using the same procedure as for Example 1, Step 7, the following intermediates were prepared.

| Compound | MS (Cl, FAB, or ES) |
|---|---|
| benzyl-OMe-pyrrolidine-NH | 192 |
| 3,4-dichlorobenzyl-OMe-pyrrolidine-NH | 260 |

Step 8:

benzyl-OMe-pyrrolidine-NH (100) →step 8→ benzyl-OMe-pyrrolidine-N-(piperidine-tBOC) (101)

Using the same procedure as for Example 1, Step 8, the following intermediates were prepared.

| Compound | MS (Cl, FAB, or ES) |
|---|---|
| benzyl-OMe-pyrrolidine-N-(piperidine-tBOC) | 375 |

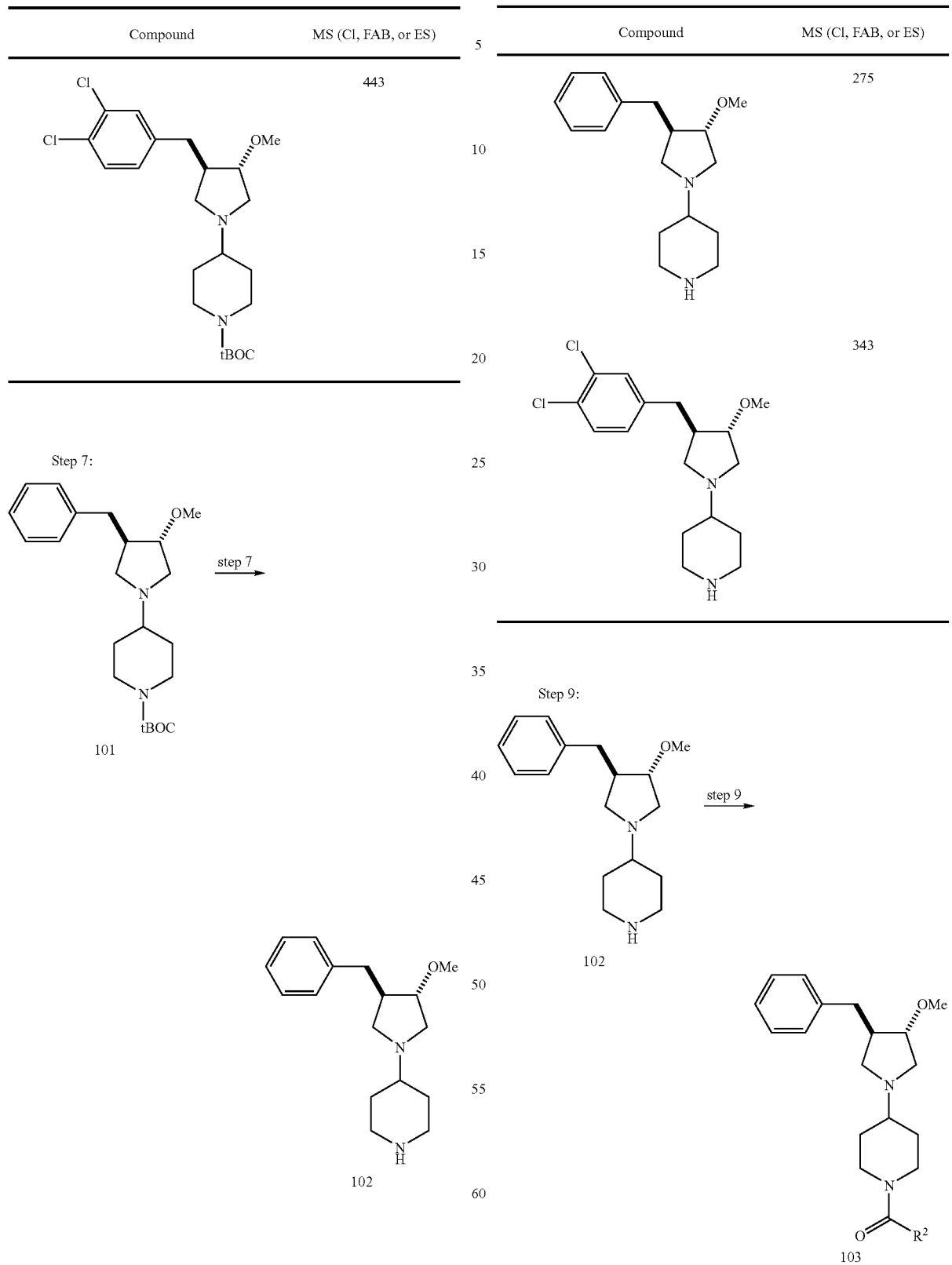
Using the same procedure as for Example 1, Step 7, the following intermediates were prepared.
Using the same procedure as for Example 1, Step 9, the following compounds were prepared:

| Ex. | Compound | MS (Cl, FAB, or ES) |
| --- | --- | --- |
| 14-A | 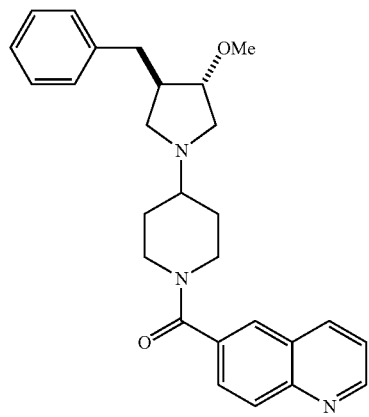 | 430 |
| 14-B | 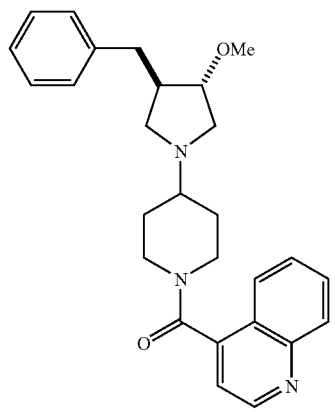 | 430 |
| 14-C | 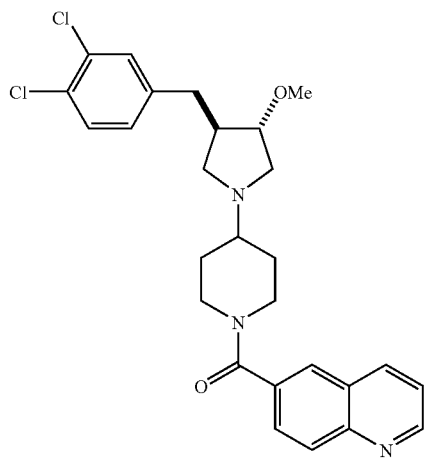 | 498 |

-continued

| Ex. | Compound | MS (Cl, FAB, or ES) |
|---|---|---|
| 14-D | 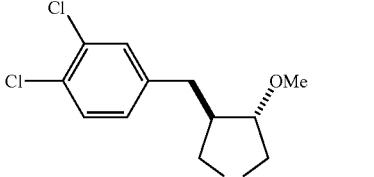 | 498 |

The following assays can be used to determine the CCR3 inhibitory and antagonistic activity of the compounds of the invention.

CCR3 SPA-Based Receptor Binding Assay:

The procedure used was disclosed in Dairaghi et al, *J. Biol. Chem.*, 272 (1997), pg. 28206-28289, and is described in detail below.

The source of the CCR3 receptors for this assay was purified membranes from a human CCR3 transfected Y3 cell line. Membranes were prepared by MDS Pharma Services (Bothell, Wash.) as follows. Cells were grown under selection (1 mg/ml G418) in 50-stack cube bioreactors with minimal media recirculation. Cells were harvested with trypsin and washed once with PBS. Cells were resuspended in 20 volumes of ice cold 2.5 mM Tris-HCl, pH 7.4 containing protease inhibitors (0.3 mM PMSF, 3 µg/ml aprotinin, 3 µg/ml luepeptin) and incubated on ice for 15 min. The swollen cells were lysed by vigorous vortexing and large debris was removed by centrifugation (1200 rpm, 5 min., 4° C.). The cleared lysate was subjected to ultra-centrifugation (100,000×g, 1 hr., 4° C.) to pellet the membrane fraction and the membrane fraction was resuspended in 25 mM HEPES, pH 7.6, 75 mM NaCl, 1 mM EDTA. Protease inhibitors were added as described above after a sample was removed for protein determination. The membrane preparation was brought to 6 to 10 mg/ml final concentration and BSA was added to 0.5%. Membranes were stored in 1 ml aliquots (−70° C.).

All compounds to be tested were dissolved in 100% DMSO to a concentration of 10 mM with sonication if necessary. Unlabelled eotaxin (R&D Systems, Minneapolis, Minn.) was used to generate standard curves. A primary stock (100 nM) was prepared in binding buffer (BB; 25 mM HEPES, pH 7.6, 75 mM NaCl, 1 mM CaCl$_2$, 5 mM MgCl$_2$, 0.5% BSA, adjusted to final pH 7.6) and stored in small aliquots (−70° C.). [$^{125}$I]-Eotaxin (NEN Life Science Products, Boston, Mass.) was resuspended in water (25 µCi/ml) and stored at −20° C.

PVT-wheat-germ agglutinin-SPA beads (PVT-WGA-SPA beads; Amersham Biosciences, Piscataway, N.J.) were resuspended in BB (20 mg/ml). PVT-WGA-SPA beads and membranes were combined in BB and slowly rotated at 4° C. for 1 hr. For 100 binding reactions, 1 mg of membranes was combined with 20 mg of PVT-WGA-SPA beads in 10 ml BB. For additional reactions, appropriate amounts of membranes and beads were combined in 10 ml BB. Membranes bound to beads were collected by centrifugation (1500 rpm, 10 min., 4° C.), resuspended in BB and combined with [$^{125}$I]-eotaxin. For 100 reactions, 5×10$^6$ cpm [$^{125}$I]-eotaxin was added to 1 mg membranes on 20 mg beads in a total of 18 ml of BB.

Competition binding reactions were initiated by adding to each well of a 96-well plate (Wallac Oy, Turku, Finland) 180 µl of [$^{125}$I]-eotaxin/membranes/beads. For compound tests, 20 µl was added to each of triplicate wells (100 µM to 10 pM final concentration). For standard curves, 20 µl of unlabelled eotaxin was added to each of triplicate wells (3 nM to 1 pM final concentration). Every well contained 0.05 nM [$^{125}$I]-eotaxin, 10 µg membranes and 200 µg PVT-WGA-SPA beads in a total volume of 200 µl. Plates were shaken briefly and incubated at room temperature for 5 hrs before counting on a scintillation counter.

An IC$_{50}$ value was interpolated from the dilution series for each compound and used to calculate a K$_i$ value using the following equation:

$$K_i = IC_{50}/(1+[\text{ligand}]/K_d)$$

Intracellular Calcium Assay:

Cell Culture:

CREM3 cells, in which the human CCR3 receptor is stably expressed in the rat Y3 cell line, were cultured in DMEM high glucose containing 10% FBS, 50 U/ml penicillin, 50 µg/ml streptomycin, 2 mM L-glutamine, 1 mg/ml G418 (Gemini Bioproducts). Cells were cultured in fresh medium every 2 days.

Assay Procedure:

Intracellular calcium levels were measured using a fluorometric imaging plate reader (FLIPR), (Molecular Devices, Sunnyvale Calif.) as described by the manufacturer. CREM3 cells were cultured overnight at 20,000 cells/well in 96 well black-wall clear bottom plates (Packard), precoated with 100 µg/ml poly D-lysine hydrobromide (Sigma). Adherent CREM3 cells were loaded with 4 µM Fluo-3 AM (Molecular Probes, Eugene, Oreg.), in pH 7.4 HBSS without phenol red, containing 20 mM HEPES, 0.5% FBS, 2.5 mM probenecid (Sigma), 0.04% pluronic acid (Molecular Probes) for 1 h at 37° C. Adherent cells were washed with wash buffer/diluent (pH 7.4 HBSS without phenol red, containing 20 mM HEPES, 0.5% BSA, 2.5 mM probenecid) by an automated Denley CellWasher (Labsystemes Oy, Helsinki, Finland); after the final wash, fluid was aspirated to a level of 100 µl. Chemokines were diluted in wash buffer/diluent at 4-fold the final concentration and added in a volume of 50 µl/well. Compounds were resuspended in dimethyl sulfoxide (DMSO) and diluted in wash buffer/diluent to 3-fold the final concentration. Each compound was titrated in half-log dilutions over 3.5 logs. DMSO control groups, which contained solvent concentrations equivalent to that in the highest concentration of compounds, were included. Cells and chemokines were maintained at 37° C. throughout all calcium measurements. Fluid additions were made according to the FLIPR recommendations for adherent (CREM3) cells. Fluorescence data was collected at 1 s interval for 60 s, followed by collection at 2 s intervals for 60 s. Background fluorescence was quantitated in wells containing cells but no chemokines and was subtracted from all experimental samples. All conditions were done in quadruplicate. Nonlinear regression analysis using GraphPad Prism (Graphpad Software Inc., San Diego, Calif.) was used to calculate $EC_{50}$ values for chemokines or $IC_{50}$ values for compounds.

In the assay to determine CCR3 receptor binding, compounds of the invention range in activity from a Ki of about 1 to about 500 nM, with preferred compounds having a range of activity from about 1 to about 100 nM, more preferably about 1 to about 50 nM. In the Calcium flux assay, preferred isomers of the invention range in activity from an $IC_{50}$ of about 3 nM to about 500 nM, with preferred compounds having a range of activity from about 3 to about 100 nM, more preferably about 3 to about 50 nM. Example 2-EE has a Ki of 2.8 nM and an $IC_{50}$ of 3.6 nM.

Compared to the CCR3 antagonists disclosed in WO 01/77101, compounds of the present invention exhibit lower Ki values in the binding assay, and lower $IC_{50}$ values in the Calcium flux assay.

For preparing pharmaceutical compositions from the CCR3 antagonist compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 10 mg to about 500 mg, preferably from about 25 mg to about 300 mg, more preferably from about 50 mg to about 250 mg, and most preferably from about 55 mg to about 200 mg, according to the particular application.

The actual dosage of CCR3 compound employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the CCR3 compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 100 mg/day to about 300 mg/day, preferably 150 mg/day to 250 mg/day, more preferably about 200 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the structural formula II

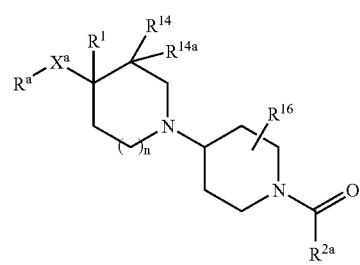

or a pharmaceutically acceptable salt thereof, wherein
n is 1;
$X^a$ is —$C(R^{13})_2$—;
$R^a$ is $R^{6a}$-phenyl;
$R^1$ is hydrogen, halogen, —OH, alkyl, hydroxyalkyl, alkoxy or alkoxyalkyl;

$R^{2a}$ is

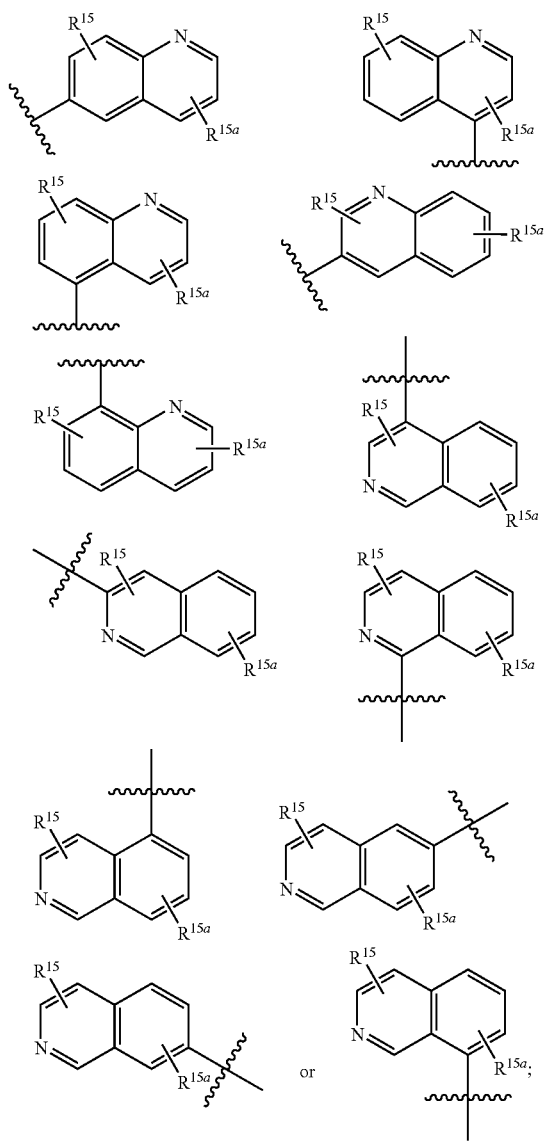

$R^{6a}$ is 1 to 3 substituents independently selected from the group consisting of hydrogen, halogen, —CF$_3$, CF$_3$O—, —CN, —NHCOCF$_3$, 5-membered heteroaryl and

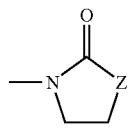

wherein Z is —O—, —NH— or —N(CH$_3$)—;

$R^{13}$ and $R^{16}$ are independently selected from the group consisting of hydrogen and alkyl;

$R^{14}$ is alkyl, alkenyl, haloalkyl, hydroxy, hydroxyalkyl, —CN, —(CR$^{20}$R$^{21}$)$_q$—O-alkyl, —(CR$^{20}$R$^{21}$)$_q$—NR$^{20}$R$^{24}$, —(CR$^{20}$R$^{21}$)$_q$—N$_3$, —(CR$^{20}$R$^{21}$)$_q$—C(O)-alkyl, —(CR$^{20}$R$^{21}$)$_q$—C(O)-phenyl, —(CR$^{20}$R$^{21}$)$_q$—COOR$^{20}$, —(CR$^{20}$R$^{21}$)$_q$—C(O)NR$^{20}$R$^{24}$, —(CR$^{20}$R$^{21}$)$_q$—S(O)$_{0-2}$—R$^{23}$, —(CR$^{20}$R$^{21}$)$_q$—N(R$^{20}$)—C(O)NR$^{20}$R$^{24}$, —(CR$^{20}$R$^{21}$)$_q$—N(R$^{20}$)—C(O)OR$^{23}$ or —(CR$^{20}$R$^{21}$)$_q$—O—C(O)R$^{23}$;

$R^{14a}$ is hydrogen or alkyl;

q is 0, 1, 2 or 3;

$R^{15}$ and $R^{15a}$ are each 1 or 2 substituents independently selected from the group consisting of H, halogen, OH, alkyl, alkoxy, —CF$_3$, —OCF$_3$, —CN, —C(O)R$^{25}$, —COOR$^{25}$, —S(O)$_{0-2}$R$^{25}$, —S(O)$_{0-2}$CF$_3$, —NR$^{20}$R$^{24}$, phenyl;

$R^{20}$ and $R^{21}$ are independently selected from the group consisting of H and alkyl;

$R^{23}$ is alkyl or phenyl; and $R^{24}$ is H, alkyl or R$^{12}$-phenyl; provided that when $R^{14}$ is —(CR$^{20}$R$^{21}$)$_q$—NR$^{20}$R$^{24}$ and $R^{24}$ is H, $R^{20}$ is alkyl.

2. A compound of claim 1 wherein n is 1 and $R^{16}$ is hydrogen.

3. A compound of claim 1 wherein $R^a$ is $R^{6a}$-phenyl, wherein $R^{6a}$ is one or two halogen substituents.

4. A compound of claim 1 wherein $R^1$ is hydrogen.

5. A compound of claim 1 wherein $R^{14}$ is alkyl, haloalkyl, hydroxy, hydroxyalkyl, alkoxy or alkoxyalkyl and $R^{14a}$ is hydrogen.

6. A compound of claim 1 wherein $R^{2a}$ is

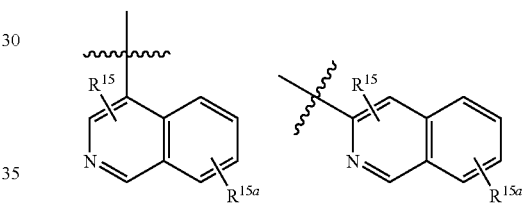

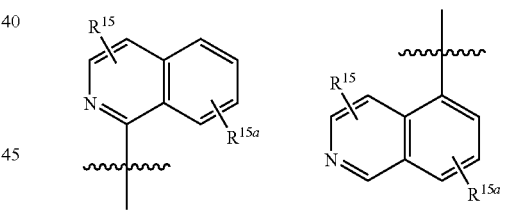

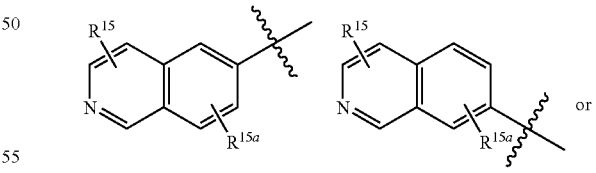

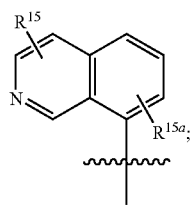

7. A compound of claim 6 wherein $R^{2a}$ is selected from the group consisting of

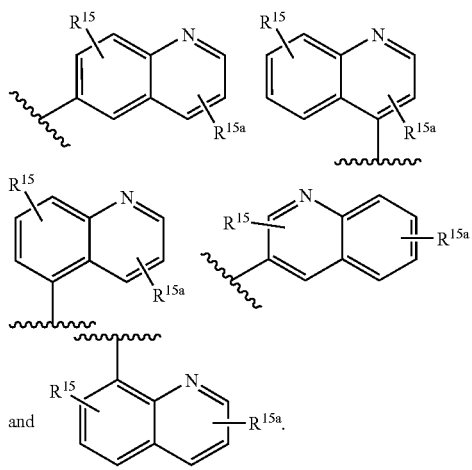

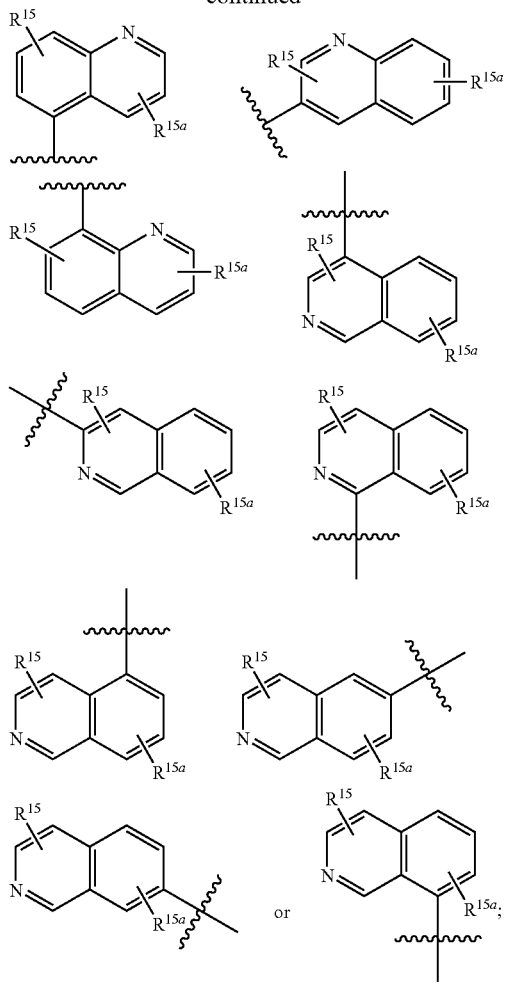

8. A compound of claim 7 wherein $R^{15}$ and $R^{15a}$ are single substituents independently selected from the group consisting of hydrogen, halogen, methyl, methoxy and $CF_3$.

9. A pharmaceutical composition comprising an effective amount of a CCR3 antagonist of claim 1 in combination with a pharmaceutically acceptable carrier.

10. A method of treating asthma comprising administering to a human in need of such treatment a therapeutically effective amount of a CCR3 antagonist of claim 1.

11. A method of treating asthma comprising administering to a human in need of such treatment a therapeutically effective amount of a CCR3 antagonist of the formula II

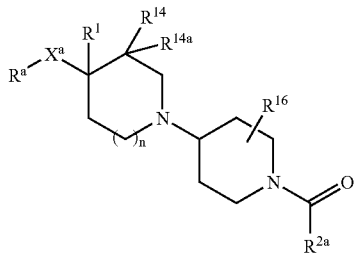

or a pharmaceutically acceptable salt thereof, wherein
n is 1;
$X^a$ is —$C(R^{13})_2$—;
$R^a$ is $R^{6a}$-phenyl;
$R^1$ is hydrogen, halogen, —OH, alkyl, hydroxyalkyl, alkoxy or alkoxyalkyl;
$R^{2a}$ is

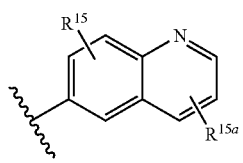 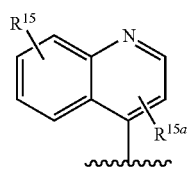

$R^{6a}$ is 1 to 3 substituents independently selected from the group consisting of hydrogen, halogen, —$CF_3$, $CF_3O$—, —CN, —$NHCOCF_3$, 5-membered heteroaryl and

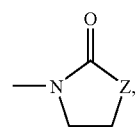

wherein Z is —O—, —NH— or —$N(CH_3)$—;
$R^{13}$ and $R^{16}$ are independently selected from the group consisting of hydrogen and alkyl;
$R^{14}$ is alkyl, alkenyl, haloalkyl, hydroxy, hydroxyalkyl, —CN, —$(CR^{20}R^{21})_q$—O-alkyl, —$CR^{20}R^{21})_q$—$NR^{20}R^{24}$, —$(CR^{20}R^{21})_q$—$N_3$, —$(CR^{20}R^{21})_q$—C(O)-alkyl, —$(CR^{20}R^{21})_q$—C(O)-phenyl, —$(CR^{20}R^{21})_q$—$COOR^{20}$, —$(CR^{20}R^{21})_q$—C(O)$NR^{20}R^{24}$, —$(CR^{20}R^{21})_q$—S(O)$_{0-2}$—$R^{23}$, —$(CR^{20}R^{21})_q$—N(R^{20})—C(O)NR^{20}R^{24}$, —$(CR^{20}R^{21})_q$—N(R^{20})—C(O)OR^{23}$ or —$(CR^{20}R^{21})_q$—O—C(O)R^{23}$;
$R^{14a}$ is hydrogen or alkyl;
q is 0, 1, 2 or 3;

$R^{15}$ and $R^{15a}$ are each 1 or 2 substituents independently selected from the group consisting of H, halogen, OH, alkyl, alkoxy, —$CF_3$, —$OCF_3$, —CN, —C(O)$R^{25}$, —COO$R^{25}$, —S(O)$_{0-2}R^{25}$, —S(O)$_{0-2}CF_3$, —N$R^{20}R^{24}$, phenyl;

$R^{20}$ and $R^{21}$ are independently selected from the group consisting of H and alkyl;

$R^{23}$ is alkyl or phenyl; and $R^{24}$ is H, alkyl or $R^{12}$-phenyl; provided that when $R^{14}$ is —(C$R^{20}R^{21}$)$_q$—N$R^{20}R^{24}$ and $R^{24}$ is H, $R^{20}$ is alkyl.

12. A method of claim 11 wherein n is 1 and $R^{16}$ is hydrogen.

13. A method of claim 11 wherein R is $R^6$-phenyl, wherein $R^6$ is one or two halogen substituents.

14. A method of claim 11 wherein $R^1$ is hydrogen.

15. A method of claim 11 wherein $R^{14}$ is alkyl, haloalkyl, hydroxy, hydroxyalkyl, alkoxy or alkoxyalkyl and $R^{14a}$ is hydrogen.

16. A method of claim 11 wherein $R^{2a}$ is

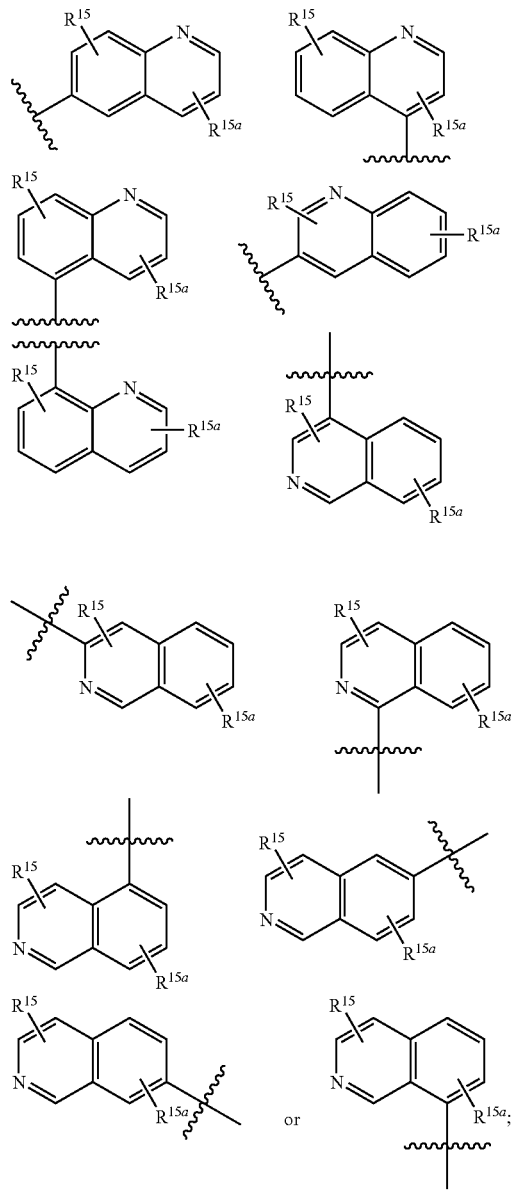

17. A method of claim 16 wherein $R^2$ is selected from the group consisting of

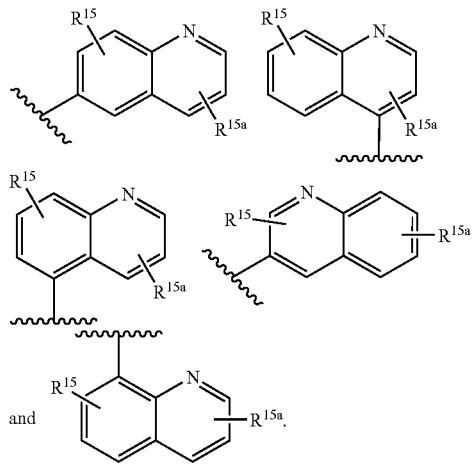

18. A method of claim 17 wherein $R^{15}$ and $R^{15a}$ are single substituents independently selected from the group consisting of hydrogen, halogen, methyl, methoxy and $CF_3$.

19. A compound selected from the group consisting of

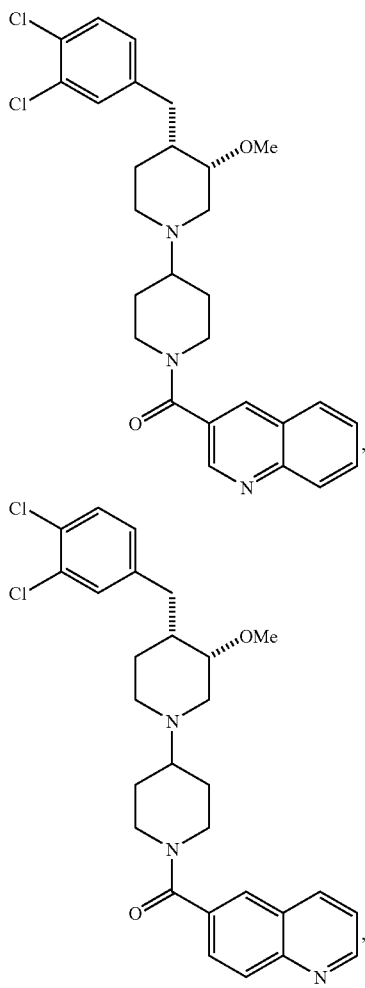

151
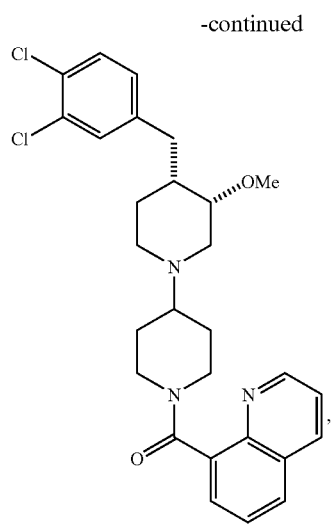
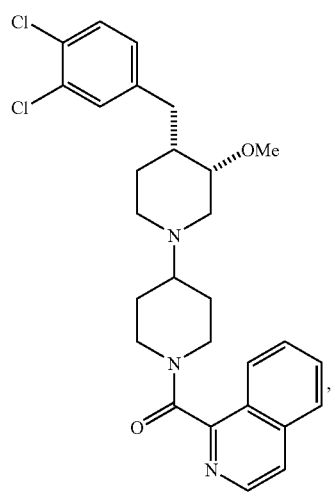
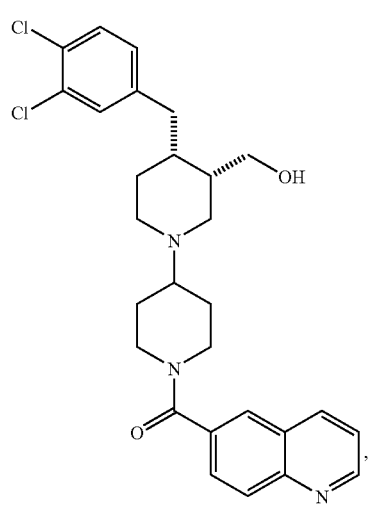
152
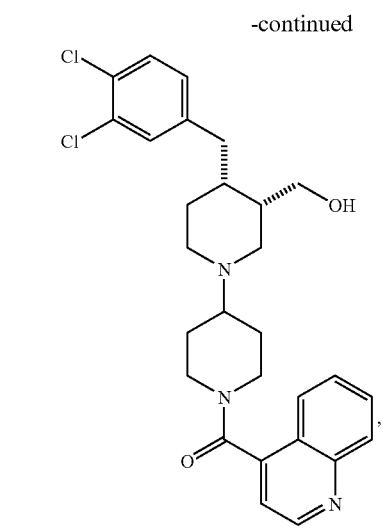
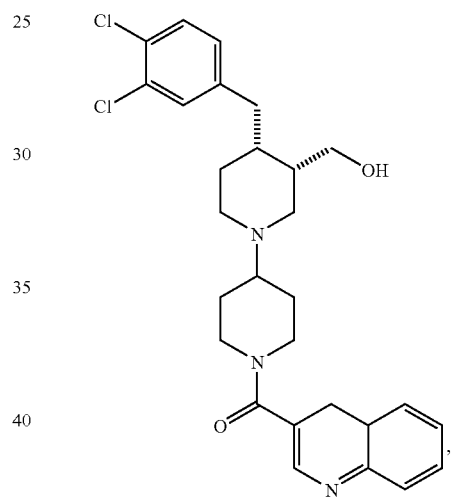
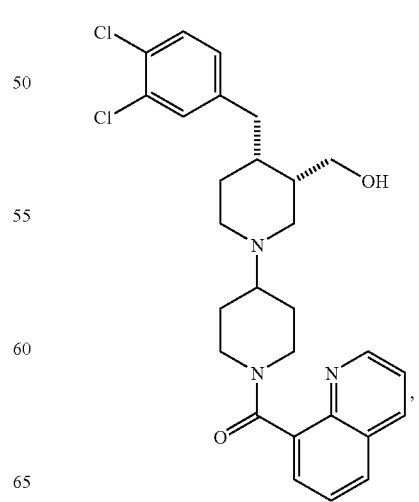

-continued
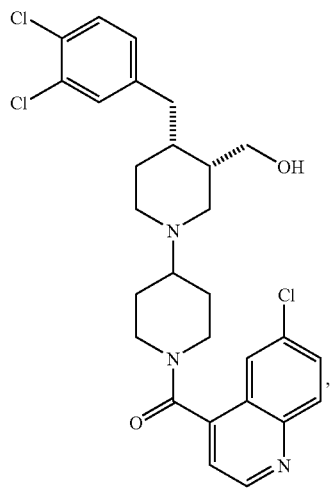
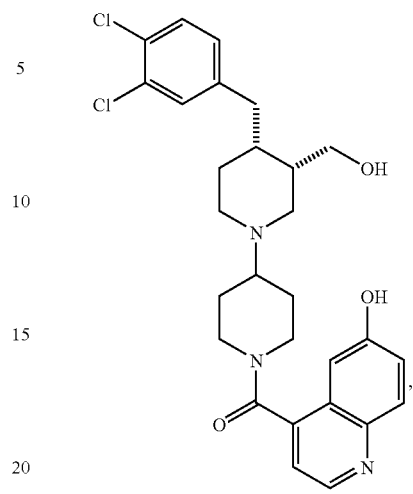
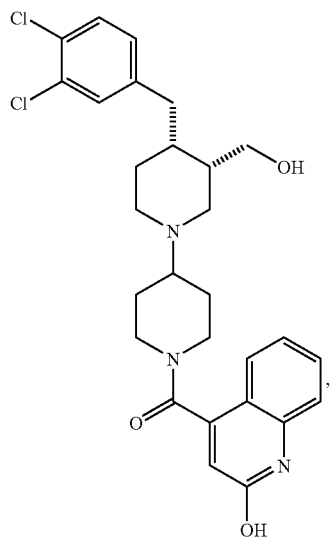
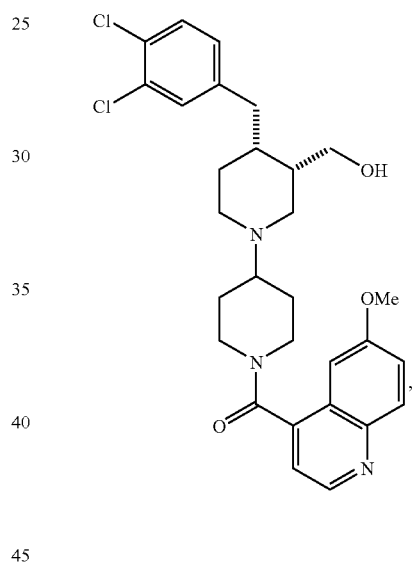
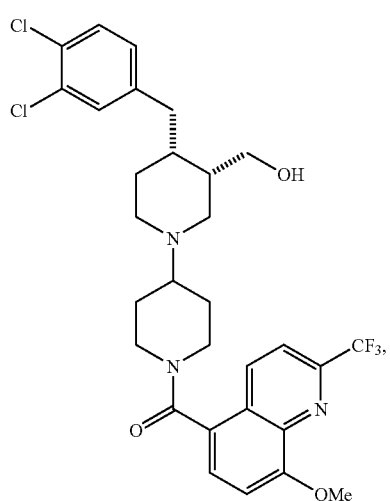
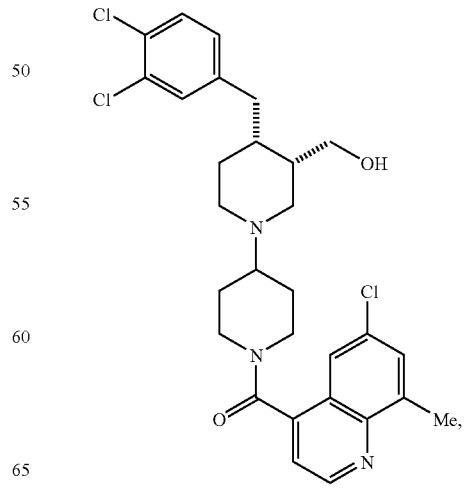

155
-continued
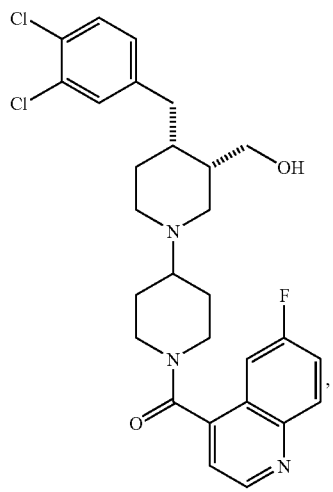
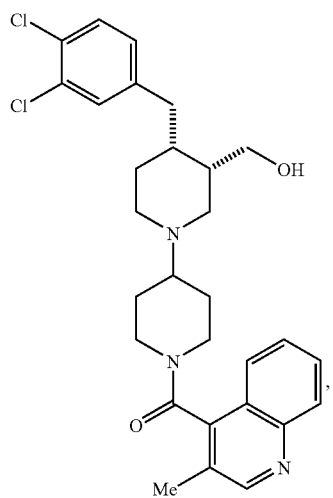
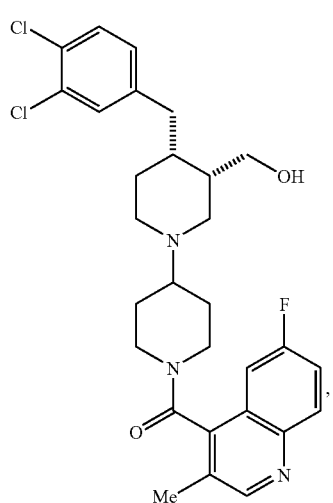
156
-continued
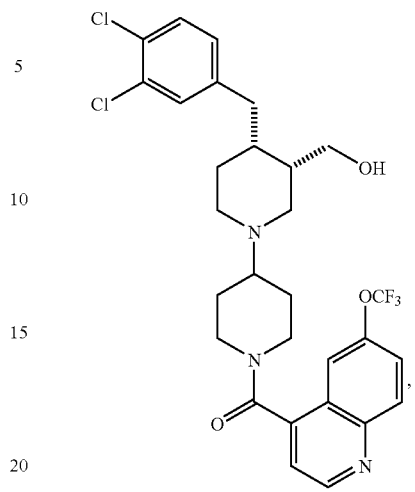
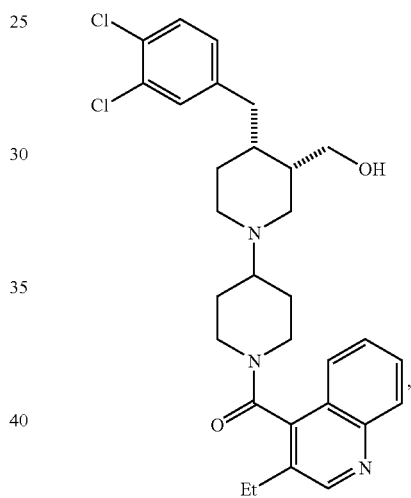
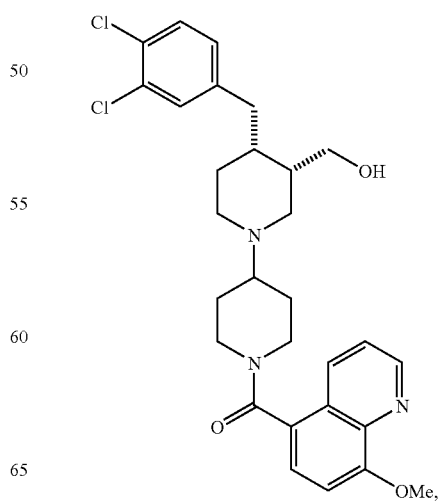

157
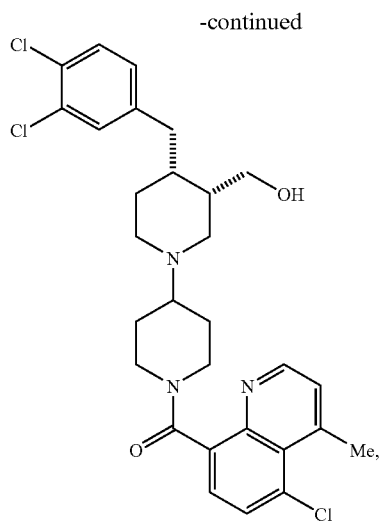
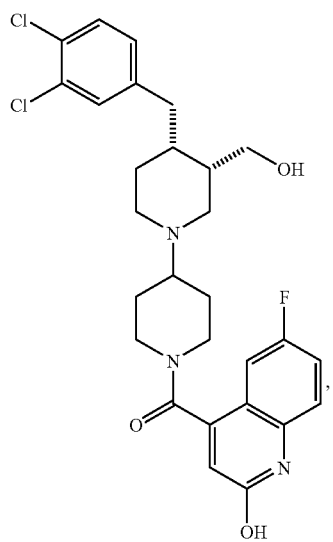
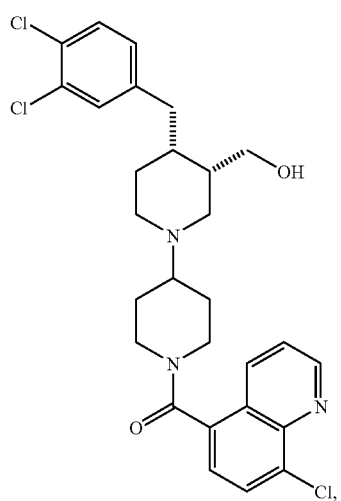
158
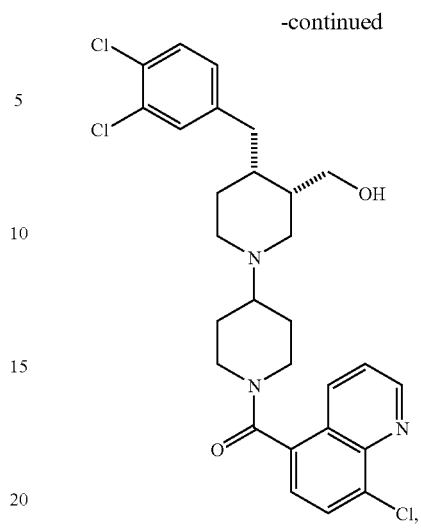
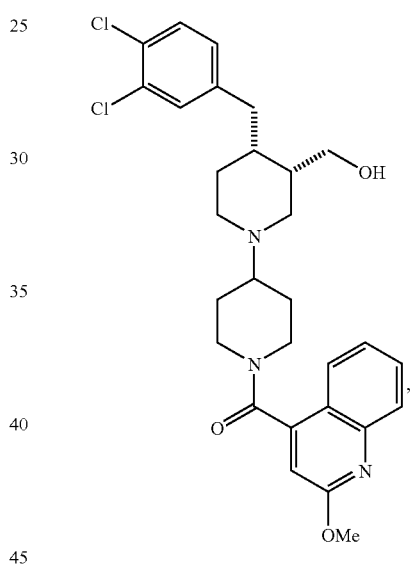
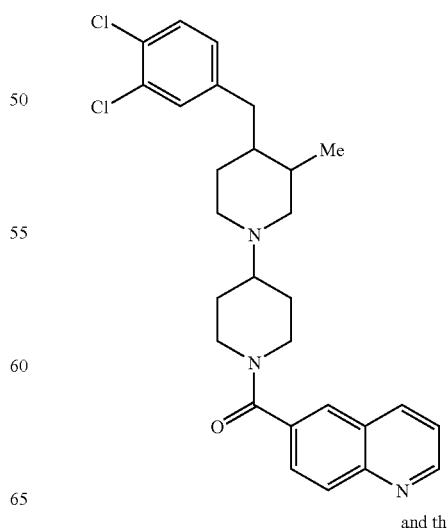
and the cis enantiomer B,

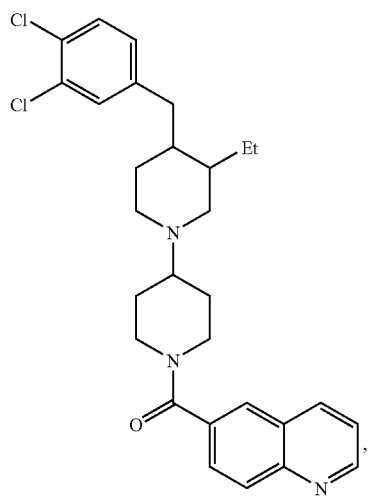
,
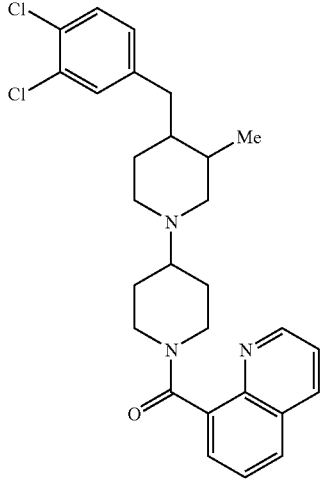
cis enantiomer B, and
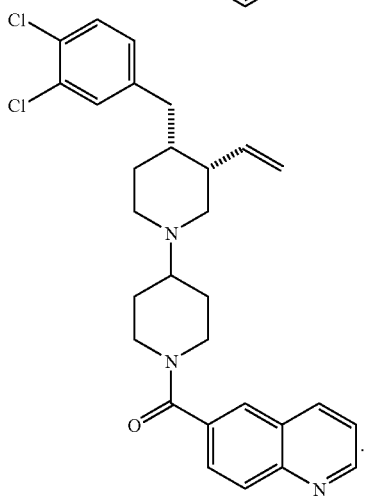
.
and the cis enantiomer B,
* * * * *